United States Patent
Heffner et al.

(10) Patent No.: US 10,907,177 B2
(45) Date of Patent: *Feb. 2, 2021

(54) COMPOUNDS FOR IMPROVED VIRAL TRANSDUCTION

(71) Applicant: bluebird bio, Inc., Cambridge, MA (US)

(72) Inventors: Garrett Collins Heffner, San Francisco, CA (US); Abraham Isaac Bassan, Palo Alto, CA (US)

(73) Assignee: bluebird bio, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/665,892

(22) Filed: Oct. 28, 2019

(65) Prior Publication Data

US 2020/0048657 A1 Feb. 13, 2020

Related U.S. Application Data

(63) Continuation of application No. 15/997,643, filed on Jun. 4, 2018, now Pat. No. 10,501,759, which is a continuation of application No. 14/348,572, filed as application No. PCT/US2012/057987 on Sep. 28, 2012, now Pat. No. 9,988,644.

(60) Provisional application No. 61/541,736, filed on Sep. 30, 2011.

(51) Int. Cl.
| | |
|---|---|
| *C12N 15/86* | (2006.01) |
| *C12N 5/0789* | (2010.01) |
| *A61K 38/46* | (2006.01) |
| *C12N 15/867* | (2006.01) |
| *A61K 35/12* | (2015.01) |

(52) U.S. Cl.
CPC .............. *C12N 15/86* (2013.01); *A61K 38/46* (2013.01); *C12N 5/0647* (2013.01); *A61K 2035/124* (2013.01); *C12N 15/867* (2013.01); *C12N 2501/02* (2013.01); *C12N 2510/00* (2013.01); *C12N 2740/16043* (2013.01); *C12N 2810/6081* (2013.01)

(58) Field of Classification Search
CPC ..................................................... C12N 15/86
See application file for complete search history.

(56) References Cited

U.S. PATENT DOCUMENTS

| | | |
|---|---|---|
| 6,610,719 B2 | 8/2003 | Paralkar et al. |
| 6,747,037 B1 | 6/2004 | Old et al. |
| 6,822,112 B1 | 11/2004 | Sato et al. |
| 8,029,780 B2 | 10/2011 | Kollet et al. |
| 8,241,903 B2 | 8/2012 | Lapidot et al. |
| 8,367,057 B2 | 2/2013 | Lapidot et al. |
| 9,107,909 B2 | 8/2015 | Pelus et al. |
| 9,675,641 B2 | 6/2017 | Pelus et al. |
| 9,988,644 B2 | 6/2018 | Heffner et al. |
| 2003/0215452 A1 | 11/2003 | Carroll et al. |
| 2005/0079616 A1 | 4/2005 | Reubinoff et al. |
| 2005/0163760 A1 | 7/2005 | Cartier-Lacave et al. |
| 2006/0247214 A1 | 11/2006 | DeLong et al. |
| 2007/0087988 A1 | 4/2007 | Sawasdikosol et al. |
| 2008/0021078 A1 | 1/2008 | Tidmarsh et al. |
| 2008/0207584 A1 | 8/2008 | Habashita et al. |
| 2008/0261922 A1 | 10/2008 | Carley et al. |
| 2009/0092589 A1 | 4/2009 | Williams |
| 2014/0234278 A1 | 8/2014 | Heffner et al. |
| 2018/0363004 A1 | 12/2018 | Heffner |

FOREIGN PATENT DOCUMENTS

| | | |
|---|---|---|
| WO | WO 1992/11355 A1 | 7/1992 |
| WO | WO98/00541 | 1/1998 |
| WO | WO2000/023567 | 4/2000 |
| WO | WO-2000/038663 | 7/2000 |
| WO | WO-2001/12596 | 2/2001 |
| WO | WO 2004/098531 | 11/2004 |
| WO | WO-2007/071456 | 6/2007 |
| WO | WO 2007/112084 A2 | 10/2007 |
| WO | WO 2008/070310 A2 | 6/2008 |
| WO | WO 2008/073748 | 6/2008 |
| WO | WO 2010/054271 | 5/2010 |
| WO | WO-2010/054271 | 5/2010 |
| WO | WO 2010/108028 A2 | 9/2010 |
| WO | WO-2013/049615 | 4/2013 |

OTHER PUBLICATIONS

The European Agency for the Evaluation of Medicinal Products (Feb. 1997, Committee for Proprietary Medicinal Products, pp. 1-6) . (Year: 1997).*
Mostoslaysky, et al., "Efficiency of Transduction of Highly Purified Murine Hematopoietic Stem Cells by Lentiviral and Oncoretoviral Vectors Under Conditions of Minimal in Vitro Manipulation", *Molecular Therapy*, 11(6): 932-940 (2005).
Cartier, Nathalie, et al. "Hematopoietic stem cell gene therapy with a lentiviral vector in X-linked adrenoleukodystrophy." *Science* 326.5954 (2009): 818-823.
Puthenveetil, Geetha, et al. "Successful correction of the human β-thalassemia major phenotype using a lentiviral vector." *Blood* 104.12 (2004): 3445-3453.

(Continued)

*Primary Examiner* — Thaian N. Ton
*Assistant Examiner* — David A. Montanari
(74) *Attorney, Agent, or Firm* — Morse, Barnes-Brown & Pendleton, P.C.; Lisa M. Warren, Esq.

(57) ABSTRACT

The present invention provides methods and compositions for improving efficacy of viral transduction of cells. More particularly, the present invention provides methods and materials useful for safely and reliably improving the efficiency of methods and materials useful for safely and reliably improving the efficiency of methods for transducing cells, such as human hematopoietic stem cells (HSC), with viruses and/or viral vectors. The compositions and methods are useful for therapeutic indications amenable to treatment with hematopoietic stem cell gene therapies.

28 Claims, 1 Drawing Sheet
Specification includes a Sequence Listing.

(56) References Cited

OTHER PUBLICATIONS

Pawliuk, Robert, et al. "Correction of sickle cell disease in transgenic mouse models by gene therapy." *Science* 294.5550 (2001): 2368-2371.
Chen, Wen Yong, et al. "Reactivation of silenced, virally transduced genes by inhibitors of histone deacetylase." *Proceedings of the National Academy of Sciences* 94.11 (1997): 5798-5803.
Tobias, Chris A., Duckhyun Kim, and Itzhak Fischer. "Improved recombinant retroviral titers utilizing trichostatin A." *Biotechniques* 29:4 (2000): 884-891.
Experimental Medicine, 2009, vol. 27, No. 13, pp. 2047-2052.
Virus, 2002, vol. 52, No. 2, pp. 225-231.
Denning, et al., "Optimization of the transductional efficiency of lentiviral vectors: effect of sera and polycations." *Molecular Biotechnology* 53.3 (2013): 308-314.
Abeyta, Michael J., et al. "Unique gene expression signatures of independently-derived human embryonic stem cell lines." *Human Molecular Genetics* 13.6 (2004): 601-608.
Alenzi, Faris Q.B., and Ali H. Bahkali. "Stem cells: Biology and clinical potential." *African Journal of Biotechnology* 10.86 (2011): 19929-19940.
Allegrucci et al., "Differences between human embryonic stem cell lines," *Human Reproduction Update*, vol. Advance Access published on Aug. 26, 2006, p. 1-18.
Bank, Arthur. "Hematopoietic stem cell gene therapy: selecting only the best." *Journal of Clinical Investigation* 112.10 (2003): 1478-1480.
Chattopadhyay, Anasuya, Tamal Raha, and M. S. Shaila. "Effect of single amino acid mutations in the conserved GDNQ motif of L protein of Rinderpest virus on RNA synthesis in vitro and in vivo." *Virus Research* 99.2 (2004): 139-145.
Dupuis, Fabienne, et al. "Prostaglandin E 2 Stimulates the Growth of Human Blood CD34 Progenitors." *Prostaglandins & Other Lipid Mediators* 55.2 (1998): 179-186.
Feher, I., and Julia Gidáli. "Prostaglandin E2 as stimulator of haemopoietic stem cell proliferation." *Nature* 247.5442 (1974): 550-551, Abstract.
Gao, L. et al., "Changes of T Cell Subsets in the Peripheral Blood of Mice after Mobilization of Hematopoietic Stem Cells by G-CSF and GM-CSF," *Acta Academiae Medicine Xuzhou*, Jul. 2007, pp. 1-2, vol. 27, No. 7.
Goichberg, Polina, et al. "cAMP-induced PKC activation increases functional CXCR4 expression on human CD34+ hematopoietic progenitors." *Blood* 107.3 (2006): 870-879.
Hoggatt, Jonathan, et al. "Prostaglandin $E_2$ enhances hematopoietic stem cell homing, survival, and proliferation." *Blood* 113.22 (2009): 5444-5455.
Horn, Peter A., et al. "Stem cell gene transfer—efficacy and safety in large animal studies." *Molecular Therapy* 10.3 (2004): 417-431.
Kolf, Catherine M., Elizabeth Cho, and Rocky S. Tuan. "Mesenchymal stromal cells: biology of adult mesenchymal stem cells: regulation of niche, self-renewal and differentiation." Arthritis Research & Therapy vol. 9.1 (2007): p. 204, 10 pages.
Levesque, Jean-Pierre, and Ingrid G. Winkler. "Mobilization of hematopoietic stem cells: state of the art." *Current opinion in organ transplantation* 13.1 (2008): 53-58.
Li, Shengqiao, Mark Waer, and An D. Billiau. "Xenotransplantation: role of natural immunity." *Transplant Immunology* 21.2 (2009): 70-74.
Lord, Allegra M., Trista E. North, and Leonard I. Zon. "Prostaglandin E2: making more of your marrow." *Cell Cycle* 6.24 (2007): 3054-3057.
McGiff, John C. "Prostaglandins, prostacyclins, and thromboxanes." *Annual Review of Pharmacology and Toxicology* 21.1 (1981): 479-509.
North, Trista E., et al. "Prostaglandin E2 regulates vertebrate haematopoietic stem cell homeostasis." *Nature* 447.7147 (2007): 1007-1012.
Sato, Noboru, et al. "Molecular signature of human embryonic stem cells and its comparison with the mouse." *Developmental Biology* 260.2 (2003): 404-413.
Skolnick, Jeffrey, and Jacquelyn S. Fetrow. "From genes to protein structure and function: novel applications of computational approaches in the genomic era." *Trends in Biotechnology* 18.1 (2000): 34-39.
Smallwood, Sherin, et al. "Different substitutions at conserved amino acids in domains II and III in the Sendai L RNA polymerase protein inactivate viral RNA synthesis." *Virology* 304.1 (2002): 135-145.
Sprangers, Ben, Waer, Mark, and Billiau, A. D.. "Xenotransplantation: where are we in 2008?." *Kidney International* 74.1 (2008): 14-21.
Taha, Masoumeh F. "Cell based-gene delivery approaches for the treatment of spinal cord injury and neurodegenerative disorders." *Current Stem Cell Research & Therapy* 5.1 (2010): 23-36.
Tomasinsig, L., and M. Zanetti. "The cathelicidins—structure, function and evolution." *Current Protein and Peptide Science* 6.1 (2005): 23-34.
Whitehurst, Christopher B., et al. "Single and multiple deletions in the transmembrane domain of the Sindbis virus E2 glycoprotein identify a region critical for normal virus growth." *Virology* 347.1 (2006): 199-207.
Zhao, Wenxiu, et al. "Embryonic stem cell markers." *Molecules* 17.6 (2012): 6196-6236.
Evers, Raymond, et al. "Transport of glutathione prostaglandin A conjugates by the multidrug resistance protein 1." *FEBS letters* 419.1 (1997): 112-116.
Paumi, Christian M., et al. "Multidrug resistance protein (MRP) 1 and MRP3 attenuate cytotoxic and transactivating effects of the cyclopentenone prostaglandin, 15-deoxy-Δ12, 14prostaglandin J2 in MCF7 breast cancer cells." *Biochemistry* 42.18 (2003): 5429-5437.
Sutton, Richard E., et al. "Transduction of human progenitor hematopoietic stem cells by human immunodeficiency virus type 1-based vectors is cell cycle dependent." *Journal of Virology* 73.5 (1999): 3649-3660.
Sugimoto, Yukihiko, and Shuh Narumiya. "Prostaglandin E receptors." *Journal of Biological Chemistry* 282.16 (2007): 11613-11617.
Buczynski, M. W., D. S. Dumlao, and E. A. Dennis. "An integrated omics analysis of eicosanoid biology " *Journal of Lipid Research* 50.7 (2009): 1015-1038.
Follenzi, Antonia, et al. "Gene transfer by lentiviral vectors is limited by nuclear translocation and rescued by HIV-1 pol sequences." *Nature Genetics* 25.2 (2000): 217-222.
Demaison, Christophe, et al. "High-level transduction and gene expression in hematopoietic repopulating cells using a human imunodeficiency virus type 1-based lentiviral vector containing an internal spleen focus forming virus promoter." *Human Gene Therapy* 13.7 (2002): 803-813.
Goessling, et al., "Prostaglandin E2 Enhances Human Cord Blood Stem Cell Xenotransplants and Shows Long-Term Safety in Preclinical Nonhuman Primate Tansplant Models," *Cell Stem Cell* 8:445-458 (Apr. 8, 2011).
Pelus, et al., "Pleiotropic Effects of Prostaglandin E2 in Hematopoiesis: Prostaglandin E2 and Other Eicosandoids Regulate Hematopoietic Stem and Progenitor Cell Functions," *Prostaglandins & Other Lipid Mediators* 96:3-9 (Jun. 21, 2011).
Blömer, Ulrike, et al. "Highly efficient and sustained gene transfer in adult neurons with a lentivirus vector." *Journal of Virology* 71.9 (1997): 6641-6649.
Ikeda, Y., et al. "Gene transduction efficiency in cells of different species by HIV and EIAV vectors." *Gene Therapy* 9.14 (2002): 932-938.
Hematti, Peiman, et al. "Retroviral transduction efficiency of G-CSF+ SCF-mobilized peripheral blood CD34+ cells is superior to G-CSF or G-CSF+ Flt3-L-mobilized cells in nonhuman primates." *Blood* 101.6 (2003): 2199-2205.
Akkina, Ramesh K., et al. "High-efficiency gene transfer into CD34+ cells with a human immunodeficiency virus type 1-based retroviral vector pseudotyped with vesicular stomatitis virus envelope glycoprotein G." *Journal of Virology* 70.4 (1996): 2581-2585.

(56) References Cited

OTHER PUBLICATIONS

Paszkiet, BJ, et al., "Histone Deacetylation Inhibitors Enhance Lentiviral Vector Production and Infectivity," *Molecular Therapy*, vol. 5, special issue 5, 5308, May 1, 2002.
Kotterman, Melissa A., and David V. Schaffer. "Engineering adeno-associated viruses for clinical gene therapy." *Nature Reviews Genetics* 15.7 (2014): 445-451.
Kaur, Tranum, Roderick A. Slavcev, and Shawn D. Wettig, "Addressing the challenge: current and future directions in ovarian cancer therapy." *Current Gene Therapy* 9.6 (2009): 434-458.
Lenzi, et al., 2014, NCBI Bookshelf, A Service of the National Library of Medicine, National Institute of Health, Oversight and Review of Clinical Gene Transfer Protocols: Assessing the Role of the Recombinant DNA Advisory Committee. Washington (DC): National Academies Press (US) pp. 1-16.
Supplementary European Patent Search Report for European Patent Application No. EP 12836507, dated Jan. 23, 2015.
International Preliminary Report on Patentability and Written Opinion of the International Searching Authority issued by the Korean Intellectual Property Office for corresponding International Application No. PCT/US2012/057987, dated Apr. 1, 2014, six pages.
International Search Report issued by the Korean Intellectual Property Office for corresponding International Application No. PCT/US2012/057987, dated Dec. 14, 2012, five pages.
Non-Final Office Action issued in U.S. Appl. No. 14/348,572, dated Nov. 6, 2015.
Final Office Action issued in U.S. Appl. No. 14/348,572, dated Apr. 26, 2016.
Non-Final Office Action issued in U.S. Appl. No. 14/348,572, dated Mar. 28, 2017.
Notice of Allowance and Fees Due issued in U.S. Appl. No. 14/348,572, dated Aug. 15, 2017.
Notice of Allowance and Fees Due issued in U.S. Appl. No. 14/348,572, dated Feb. 5, 2018.
Non-Final Office Action issued in U.S. Appl. No. 15/997,643, dated May 9, 2019.
Notice of Allowance and Fees Due issued in U.S. Appl. No. 15/997,643, dated Sep. 24, 2019.
Notice of opposition to a European Patent in Patent No. EP2760994, on behalf of Muller Fottner Steinecke, dated Feb. 27, 2018.
Notice of opposition to a European Patent in Patent No. EP2760994, on behalf of Sagittarius Intellectual Property LLP, dated Feb. 28, 2018.
Uchida, Naoya, et al. "Development of a human immunodeficiency virus type 1-based lentiviral vector that allows efficient transduction of both human and rhesus blood cells." *Journal of virology* 83.19 (2009): 9854-9862.
Ueno, Ryuji, Sachiko Kuno, and Osamu Hayashi. "Possible pathogenesis of acquired immune deficiency syndrome in homosexual males: an unexpected action of seminal prostaglandin E2 on AIDS-vrus infection." *Advances in prostaglandin, thromboxane and leukotriene research* 17 (1987): 151-154.
De Waart, Dirk R., et al. "Multidrug resistance associated protein 2 mediates transport of prostaglandin E2." *Liver International* 26.3 (2006): 362-368.
Nguyen, Tuan Huy, et al. "Highly efficient lentiviral vector-mediated transduction of nondividing, fully reimplantable primary hepatocytes." *Molecular therapy* 6.2 (2002): 199-209.

Robertson, Rose Marie, et al. "Thromboxane A2 in vasotonic angina pectoris: evidence from direct measurements and inhibitor trials." *New England Journal of Medicine* 304.17 (1981): 998-1003.
Case, Scott S., et al. "Stable transduction of quiescent CD34+ CD38—human hematopoietic cells by HIV-1-based lentiviral vectors." *Proceedings of the National Academy of Sciences* 96.6 (1999): 2988-2993.
Uchida, N., et al. "Optimal conditions for lentiviral transduction of engrafting human CD34+ cells." *Gene therapy* 18.11 (2011): 1078-1086.
Heffner, et al., "Prostaglandin E2 Increases Lentiviral Vector Transduction Efficiency of Adult Human Hematopoietic Stem and Progenitor Cells." *Mol Ther*, (2018) 89926, 1: 320-328.
PubChem entry for Thromboxane B2 (from https://pubchem.ncbi.nlm.nih.gov/compound/thromboxande_B2).
Structural Similarity of Prostaglandins.
Technical Resource document detailing formulation of Gibco TM—IMDM (Catalogue No. 12440—TherrnoFisher Scientific) / https://www.thermofisher.com/uk/en/home/technical-resources/media-formulation.76.html.
Hoggart, Jonathan G., Doctor of Philosophy thesis—"Eicosanoid Regulation of Hematopoietic Stem and Progenitor Cell Function" Permanent Link: http://hdl.handle.net/1805/2206 date: Jul. 21, 2010.
Liu, Y., et al., "Identification of parameters required for efficient lentiviral vector transduction and engraftment of human cord blood CD34+ NOD/SCID-repopulating cells." Exp. Hematol. 36:947-956, 2008.
Piacibello, et al., "Lentiviral gene transfer and ex vivo expansion of human primitive stem cells capable of primary, secondary, and tertiary multilineage repopulation in NOD/SCID mice." Blood 100:4391-4400, 2002.
Tesio, et al., "Sustained Long-Term Engraftment and Transgene Expression of Peripheral Blood CD34+ Cells Transduced with Third-Generation Lentiviral Vectors." Stem Cells 26:1620-1627, 2008.
Hayakawa, et al., "Transient In Vivo β-Globin Production After Lentiviral Gene Transfer to Hematopoietic Stem Cells in the Non-human Primate." Hum Gene Ther. 20(6):563-72, Jun. 2009.
Li, et al., "Optimal promoter usage for lentiviral vector-mediated transduction of cultured central nervous system cells." J. Neurosc Methods. 189(1):56-64, May 30, 2010.
Giry-Laterriere, et al., Chapter 8 pp. 183-209; Lentiviral Vectors. In: Merten OW., Al-Rubeai M. (eds) Viral Vectors for Gene Therapy. Methods in Molecular Biology (Methods and Protocols), vol. 737, Humana Press; ISBN: 978-1-61779-094-2.
Notice of opposition to a European Patent in Patent No. EP 3269802, on behalf of HGF Limited, dated Jul. 21, 2020.
Notice of opposition to a European Patent in Patent No. EP 3269802, on behalf of Script IP Limited, dated Jul. 23, 2020.
Decision of opposition to a European Patent in Patent No. EP 2760994, dated Nov. 8, 2019.
Notice of appeal of opposition decision of Patent No. EP 2760994, dated Jan. 16, 2020.
Reddy, et al., "Histone Deacetylase Inhibitor Suberoylanilide Hydroxamic Acid Reduces Acute Graft-Versus-Host Disease and Preserves Graft-Versus-Leukemia Effect," Proc Natl Acad Sci USA, vol. 101, No. 11, pp. 3921-3926.
Xinhua Bao, (X-Linked Adrenoleukodystrophy), Chinese Journal of Practical Pediatrics, vol. 24, No. 7, pp. 504-507, 2009 (with English translation of relevant portion).

\* cited by examiner

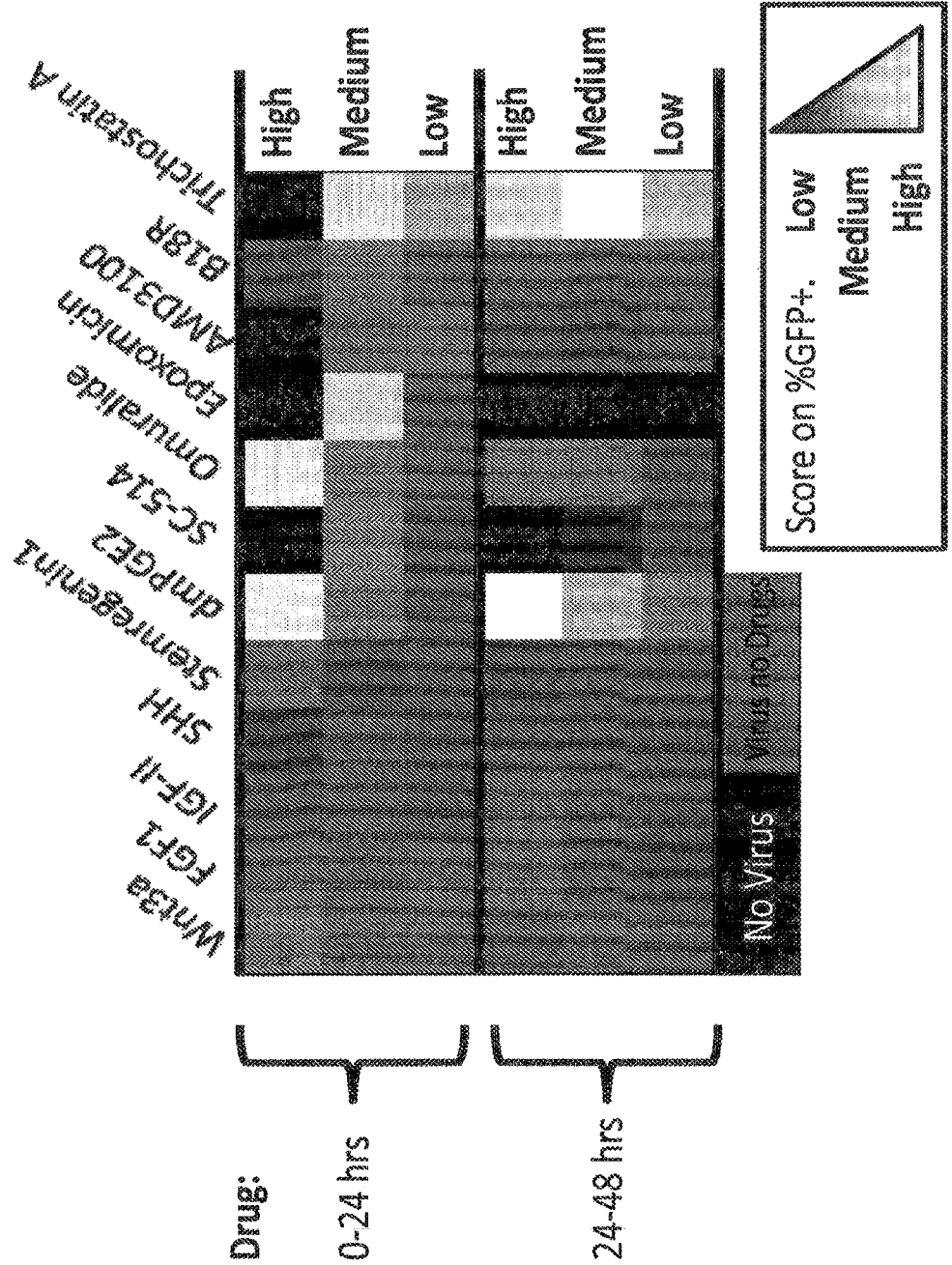

COMPOUNDS FOR IMPROVED VIRAL TRANSDUCTION

CROSS REFERENCE TO RELATED APPLICATIONS

This application is a continuation of U.S. application Ser. No. 15/997,643, filed Jun. 4, 2018, which is a continuation of U.S. application Ser. No. 14/348,572 (U.S. Pat. No. 9,988,644), filed Mar. 28, 2014, which is a national stage filing under 35 U.S.C. § 371 of International Application No. PCT/US2012/057987, filed Sep. 28, 2012, which claims the benefit of U.S. Provisional Application No. 61/541,736, filed Sep. 30, 2011, the entire teachings of which are herein incorporated by reference.

BACKGROUND

Technical Field

The present invention generally relates to improving the efficacy of methods of viral transduction of cells. More particularly, the present invention provides methods and materials useful for improving the efficiency of transducing cells, such as human hematopoietic stem cells (HSC), with viruses and/or viral vectors that may be useful for therapeutic indications.

Description of the Related Art

The Food and Drug Administration (FDA) has not yet approved any human gene therapy product for sale. Current gene therapy is experimental and has not proven very successful in clinical trials. Little progress has been made since the first gene therapy clinical trial began in 1990. In 1999, gene therapy suffered a major setback with the death of 18-year-old Jesse Gelsinger. Jesse was participating in a gene therapy trial for ornithine transcarboxylase deficiency (OTCD). He died from multiple organ failures 4 days after starting the treatment. His death is believed to have been triggered by a severe immune response to the adenovirus carrier.

Another major blow came in January 2003, when the FDA placed a temporary halt on all gene therapy trials using retroviral vectors in blood stem cells. FDA took this action after it learned that a second child treated in a French gene therapy trial had developed a leukemia-like condition. Both this child and another who had developed a similar condition in August 2002 had been successfully treated by gene therapy for X-linked severe combined immunodeficiency disease (X-SCID), also known as "bubble baby syndrome." FDA's Biological Response Modifiers Advisory Committee (BRMAC) met at the end of February 2003 to discuss possible measures that could allow a number of retroviral gene therapy trials for treatment of life-threatening diseases to proceed with appropriate safeguards. In April of 2003, the FDA eased the ban on gene therapy trials using retroviral vectors in blood stem cells.

Recently, however, several groups have led moderately successful gene therapy trials in combating several diseases. In, 2008, UK researchers from the UCL Institute of Ophthalmology and Moorfields Eye Hospital NIHR Biomedical Research Centre announced a successful gene therapy clinical trial for treatment of Leber's congenital amaurosis, a type of inherited blindness. The results showed that the experimental treatment is safe and can improve sight (Maguire et al., *N Engl J Med.* 358(21):2240 (2008)).

In 2011, Neurologix, Inc. announced positive results in a Phase 2 trial of its investigational gene therapy for advanced Parkinson's disease (PD), NLX-P101. Study participants who received NLX-P101 experienced statistically significant and clinically meaningful improvements in off-medication motor scores compared to control subjects who received sham surgery. In the trial, this benefit was seen at one month and continued virtually unchanged throughout the six month blinded study period. The results also demonstrated a positive safety profile for NLX-P101, with no serious adverse events related to the gene therapy or surgical procedure reported. Patients enrolled in the trial had moderate to advanced PD and were not adequately responsive to current therapies.

In 2009, a French group of scientists reported using hematopoietic stem cell mediated gene therapy to successfully treat X-linked adrenoleukodystrophy (ALD). Autologous stem cells were removed from the patients, genetically corrected ex vivo and then re-infused into the patients after they had received myeloablative treatment. Over a span of 24 to 30 months of follow-up, polyclonal reconstitution, with 9 to 14% of granulocytes, monocytes, and T and B lymphocytes expressing the ALD protein was detected. These results strongly suggest that hematopoietic stem cells were transduced in the patients. Beginning 14 to 16 months after infusion of the genetically corrected cells, progressive cerebral demyelination in the two patients stopped.

Recent progress in the field of gene therapy has raised the hope that patients afflicted with hemoglobinopathies such as β-thalassemia and sickle cell anemia will benefit from novel therapeutic approaches. Transplantation of hematopoietic cells (HCs) modified with lentiviral vectors carrying the β-globin gene has resulted in long-term correction of several mouse models of hemoglobin disorders Imren et al, *Proc Natl Acad Sci USA.* 2002; 99(22):14380-14385; Malik et al., *Ann NYAcadSci.* 2005; 1054:238-249; May et al, *Nature.* 2000; 406(6791):82-86; Pawliuk et al, *Science.* 2001; 294 (5550): 2368-2371), but in contrast, has led to transfusion independence in only one β-thalassemic patient (Cavazzana-Calvo et al, *Nature.* 2010; 467(7313):3 18-322).

Although the main advantages of infusing genetically modified autologous cells are to avoid the risks of GVHD and immunosuppressive pretransplant conditioning as well as to address the lack of compatible donors, current therapy faces at least three substantive caveats: the requirement for toxic myeloablation (Dunbar et al., *Hum Gene Ther.* 1998; 9(17):2629-2640); current gene transfer methods are unable to transduce more than a fraction of hematopoietic stem cells (HSCs) (Santoni de Sio and Naldini, *Methods Mol Biol.* 2009; 506:59-70); and various in vivo selection strategies available suffer from suboptimal efficacy and safety (Beard et al., *J Clin Invest.* 2010; 120(7):2345-2354; Cornetta et al, *Cancer Gene Ther.* 2006; 13(9):886-895; Milsom et al, *Cancer Res.* 2008; 68(15): 6171-6180). For example, in disorders amenable to hematopoietic stem cell therapy, e.g., sickle cell disease, β-thalassemia, adrenoleukodystrophy, and adrenomyeloneuropathy, limitations include, but are not limited to, inefficient transduction of hematopoietic stem or progenitor cells, the requirement for toxic myelosuppressive or myeloablative therapy, and a lack of optimal methods for in vivo selection of transduced cells.

Accordingly, there is a need in the art for improved methods of gene therapy and, in particular, for the treatment or prevention of hematopoietic disorders. The present invention offers solutions to these and other problems that plague the art.

BRIEF SUMMARY

The present invention generally provides methods and compositions comprising a compound that increases prostaglandin EP receptor signaling for improving viral transduction efficiency. The inventive compositions and methods further provide safer and more reliable methods for transducing cells, such as human hematopoietic stem cells (HSC), with viruses and/or viral vectors. The compositions and methods are useful for therapeutic indications amenable to treatment with hematopoietic stem cell gene therapies.

In various embodiments, the present invention contemplates, in part, a method for increasing the transduction efficiency of cells cultured with a retrovirus that comprises culturing the cells and the retrovirus in a culture medium that comprises one or more compounds that increase prostaglandin EP receptor signaling. In one embodiment, the compound is a small molecule.

In one embodiment, the cells are stem or progenitor cells.

In a particular embodiment, the stem or progenitor cells are selected from the group consisting of: embryonic stem cells and induced pluripotent stem cells.

In a further embodiment, the stem or progenitor cell are selected from the group consisting of: mesenchymal stem cells, hematopoietic stem cells, neuronal stem cells, retinal stem cells, cardiac muscle stem cells, skeletal muscle stem cells, adipose tissue derived stem cells, chondrogenic stem cells, liver stem cells, kidney stem cells, and pancreatic stem cells.

In a certain embodiment, the stem or progenitor cells are hematopoietic stem or progenitor cells.

In an additional embodiment, the cells are selected from the group consisting of: osteoblasts, chondrocytes, adipocytes, skeletal muscle, cardiac muscle, neurons, astrocytes, oligodendrocytes, Schwann cells, retinal cells, corneal cells, skin cells, monocytes, macrophages, neutrophils, basophils, eosinophils, erythrocytes, megakaryocytes, dendritic cells, T-lymphocytes, B-lymphocytes, NK-cells, gastric cells, intestinal cells, smooth muscle cells, vascular cells, bladder cells, pancreatic alpha cells, pancreatic beta cells, pancreatic delta cells, hepatocytes, renal cells, adrenal cells, and lung cells.

In a further particular embodiment, the cells are hematopoietic stem or hematopoietic progenitor cells.

In one embodiment, at least about 50% of the hematopoietic stem or progenitor cells are transduced.

In another embodiment, at least about 75% of the hematopoietic stem or progenitor cells are transduced.

In yet another embodiment, at least about 90% of the hematopoietic stem or progenitor cells are transduced.

In particular embodiments, any of the compositions or methods disclosed herein, comprise one or more compounds that increases prostaglandin EP receptor signaling selected from the group consisting of: $PGA_2$; $PGB_2$; $PGD_2$; PGEi; $PGE_2$; $PGF_2$; $PGI_2$; $PGH_2$; $PGD_2$; and precursors, metabolites, derivatives and analogues thereof.

In certain embodiments, any of the compositions or methods disclosed herein, comprise one or more compounds that increases prostaglandin EP receptor signaling selected from the group consisting of: 15d-$PGD_2$; delta12-$PGJ_2$; 2-hydroxyheptadecatrienoic acid (HHT); Thromboxane A2; Thromboxane B2; Iloprost; Treprostinil; Travoprost; Carboprost tromethamine; Tafluprost; Latanoprost; Bimatoprost; Unoprostone isopropyl; Cloprostenol; Oestrophan; Superphan; Misoprostol; Butaprost; Linoleic Acid; 13(s)-HODE; LY171883; Mead Acid; Eicosatrienoic Acid; Epoxyeicosatrienoic Acid; ONO-259; Cay 1039; a $PGE_2$ receptor agonist; 16,16-dimethyl $PGE_2$; 19(R)-hydroxy $PGE_2$; 16,16-dimethyl $PGE_2$ p-(p-acetamidobenzamido) phenyl ester; 11-deoxy-16,16-dimethyl $PGE_2$; 9-deoxy-9-methylene-16,16-dimethyl $PGE_2$; 9-deoxy-9-methylene $PGE_2$; Sulprostone; $PGE_2$ serinol amide; $PGE_2$ methyl ester; 16-phenyl tetranor $PGE_2$; 15(S)-15-methyl $PGE_2$; 15(R)-15-methyl $PGE_2$; Corey alcohol-A; Corey alcohol-B; Corey diol; BIO; 8-bromo-cAMP; Forskolin; Bapta-AM; Fendiline; Nicardipine; Nifedipine; Pimozide; Strophanthidin; Lanatoside; L-Arg; Sodium Nitroprusside; Sodium Vanadate; Bradykinin; Mebeverine; Flurandrenolide; Atenolol; Pindolol; Gaboxadol; Kynurenic Acid; Hydralazine; Thiabendazole; Bicuclline; Vesamicol; Peruvoside; Imipramine; Chlorpropamide; 1,5-Pentamethylenetetrazole; 4-Aminopyridine; Diazoxide; Benfotiamine; 12-Methoxydodecenoic acid; N-Formyl-Met-Leu-Phe; Gallamine; IAA 94; and Chlorotrianisene.

In some embodiments, any of the compositions or methods disclosed herein comprise one or more compounds that increase prostaglandin EP receptor signaling selected from the group consisting of: prostaglandin E2($PGE_2$), or 16,16-dimethyl $PGE_2$.

In additional embodiments, any of the methods disclosed herein further comprise culturing the cells and retrovirus in the presence of a histone deacetylase (HDAC) inhibitor.

In one embodiment, the HDAC inhibitor is selected from the group consisting of: Trichostatin A (TSA), valproic acid (VPA), sodium butyrate, suberoylanilide hydroxamic acid (SAHA), sodium phenylbutyrate, depsipeptide, trapoxin (TPX), cyclic hydroxamic acid-containing peptide 1 (CHAP1), MS-275, LBH589, and PXD-101.

In various embodiments, any of the compositions or methods disclosed herein comprise a retrovirus that is a lentivirus.

In particular embodiments, any of the compositions or methods disclosed herein comprise a retrovirus that is a Human immunodeficiency virus (HIV) virus.

In certain embodiments, any of the compositions or methods disclosed herein comprise a retrovirus pseudotyped with a vesicular stomatitis virus G-protein (VSV-G) envelope protein.

In additional embodiments, any of the methods disclosed herein comprise culturing the cells in the presence of the compound that increases prostaglandin EP receptor signaling prior to transduction.

In particular embodiments, the cells are cultured with the compound that increases prostaglandin EP receptor signaling for at least about 2 hours.

In further embodiments, the cells are cultured with the compound that increases prostaglandin EP receptor signaling for at least about 4 hours.

In certain embodiments, the cells are cultured in the presence of the compound that increases prostaglandin EP receptor signaling during transduction.

In further embodiments, the cells are cultured in the presence of the compound that increases prostaglandin EP receptor signaling for at least about twenty-four hours.

In additional embodiments, the cells are cultured in the presence of the compound that increases prostaglandin EP receptor signaling during the first twenty-four hours of transduction.

In some embodiments, the cells are cultured in the presence of the compound that increases prostaglandin EP receptor signaling during the first forty-eight hours of transduction.

In particular embodiments, any of the compositions or methods disclosed herein comprise a retrovirus that comprises a vector comprising: a left (5') retroviral LTR; an expression control sequence operably linked to a gene of interest; and a right (3') retroviral LTR.

In certain embodiments, any of the compositions or methods disclosed herein comprise a retrovirus that comprises a vector comprising: a left (5') HIV-1 LTR; a Psi packaging sequence (Ψ+); an HIV-1 central polypurine tract/DNA flap (cPPT/FLAP); a rev response element (RRE); a β-globin promoter and a β-globin locus control region (LCR) operably linked to a gene of interest; and a right (3') retroviral LTR that comprises: one or more insulator elements, or a rabbit β-globin polyA sequence (rPgpA). In various embodiments, the hematopoietic stem or progenitor cells are administered to a patient suffering from a hemoglobinopathy.

In various particular embodiments, the hemoglobinopathy is β-thalassemia or sickle cell disease.

In certain embodiments, any of the compositions or methods disclosed herein comprise a vector comprising: a left (5') HIV-1 LTR; a Psi (Ψ) packaging signal; a cPPT/FLAP; an RRE; a MND promoter, operably linked to a polynucleotide encoding a human ABCD1 polypeptide; a right (3') HIV-1 LTR; and a rabbit β-globin polyadenylation sequence. In various certain embodiments, the hematopoietic stem or progenitor cells are administered to a patient suffering from an adrenoleukodystrophy or an adrenomyeloneuropathy.

In various embodiments, the retrovirus is replication defective.

BRIEF DESCRIPTION OF THE SEVERAL VIEWS OF THE DRAWINGS

FIG. 1 shows the results of a screen for compounds that promote viral transduction of CD34+ cells. CD34+ cells were thawed and pre-stimulated with SCF, TPO, FltL, and IL3, then transduced with GFP+ lentivirus. Cells were additionally exposed to soluble factors at high, medium, or low concentrations (See Table 1) either during the pre-stimulation period (0-24 hours) or during transduction period (24-48 hours). Cells were then washed and analyzed by flow cytometry after approximately 1 week in culture. The percentage of cells that were GFP+ was determined and illustrated as a heat map. Grey represents approximately 45% cells transduced, and the dynamic range was 0% (black) to ~92% (white).

BRIEF DESCRIPTION OF THE SEQUENCE IDENTIFIERS

SEQ ID NO: 1 sets forth a polynucleotide sequence of a human alpha globin cDNA.
SEQ ID NO: 2 sets forth an amino acid sequence of a human alpha globin polypeptide.
SEQ ID NO: 3 sets forth an amino acid sequence of a mouse alpha globin polypeptide.
SEQ ID NO: 4 sets forth an amino acid sequence of a rat alpha globin polypeptide.
SEQ ID NO: 5 sets forth a polynucleotide sequence of a human beta globin cDNA.
SEQ ID NO: 6 sets forth an amino acid sequence of a human beta globin polypeptide.
SEQ ID NO: 7 sets forth an amino acid sequence of a mutant human beta globin polypeptide.
SEQ ID NO: 8 sets forth an amino acid sequence of a mouse beta globin polypeptide.
SEQ ID NO: 9 sets forth an amino acid sequence of a rat beta globin polypeptide.
SEQ ID NO: 10 sets forth a polynucleotide sequence of a human gamma globin cDNA.
SEQ ID NO: 11 sets forth an amino acid sequence of a human gamma globin polypeptide.
SEQ ID NO: 12 sets forth an amino acid sequence of a mouse gamma globin polypeptide.
SEQ ID NO: 13 sets forth an amino acid sequence of a rat gamma globin polypeptide.
SEQ ID NO: 14 sets forth a polynucleotide sequence of a human delta globin cDNA.
SEQ ID NO: 15 sets forth an amino acid sequence of a human delta globin polypeptide.
SEQ ID NO: 16 sets forth a cDNA sequence encoding an ACBD1 polynucleotide.
SEQ ID NO: 17 sets forth a cDNA sequence encoding an ACBD1 polynucleotide.
SEQ ID NO: 18 sets forth an amino acid sequence of an ACBD1 polypeptide.

DETAILED DESCRIPTION

A. Overview

The present invention generally relates to improved gene therapy compositions and methods of using the same to treat, prevent, or ameliorate genetic disorders. One significant challenge for gene therapy is to increase the transduction efficiency of cell comprising the therapeutic gene that will be delivered to a subject, where the corrected cells do not have an intrinsic selective advantage over nontransduced cells.

The present invention is based, in part, on the unexpected discovery that the novel cellular transduction methods of the invention can be used to expand or increase the numbers of therapeutic cells, i.e., corrected cells, in vitro, ex vivo, or in vivo to further increase the efficacy of gene therapy. Without wishing to be bound to any particular theory, the present invention contemplates, in part, that by increasing the transduction efficiency of cells, more corrected cells are generated per transduction and thus, gene therapy methods of the present invention require administration of fewer numbers of cells to provide therapeutic, preventive, or ameliorative endpoints for the subjects receiving the gene therapy. Moreover, because a higher number of transduced cells are delivered to the patient, myelosuppressive or myeloablative therapy is not necessarily required to achieve therapeutic, preventive, or ameliorative endpoints.

Accordingly, the present invention addresses an unmet clinical need for improving the efficiency of gene therapy in the treatment of genetic diseases, whereby a greater number of therapeutic cells within a transduced cell population can be administered to a subject to provide a therapeutic, preventive, or ameliorative effect. The invention specifically relates to surprisingly efficient cellular transduction methods, vectors, and genetically engineered cells to facilitate the desired clinical outcomes for gene therapy.

The practice of the present invention will employ, unless indicated specifically to the contrary, conventional methods of molecular biology and recombinant DNA techniques within the skill of the art, many of which are described below for the purpose of illustration. Such techniques are explained fully in the literature. See, e.g., Sambrook, et al., Molecular Cloning: A Laboratory Manual (2nd Edition, 1989); Maniatis et al, Molecular Cloning: A Laboratory Manual (1982); DNA Cloning: A Practical Approach, vol. I & II (D. Glover, ed.); Oligonucleotide Synthesis (N. Gait, ed., 1984); Nucleic Acid Hybridization (B. Hames & S. Higgins, eds., 1985); Transcription and Translation (B. Hames & S. Higgins, eds., 1984); Animal Cell Culture (R. Freshney, ed., 1986); A Practical Guide to Molecular Cloning (B. Perbal, ed., 1984).

All publications, patents and patent applications cited herein are hereby incorporated by reference in their entirety.

B. Definitions

Unless defined otherwise, all technical and scientific terms used herein have the same meaning as commonly understood by those of ordinary skill in the art to which the invention belongs. For the purposes of the present invention, the following terms are defined below.

As used herein, the term "retrovirus" refers an RNA virus that reverse transcribes its genomic RNA into a linear double-stranded DNA copy and subsequently covalently integrates its genomic DNA into a host genome. Retroviruses are a common tool for gene delivery (Miller, 2000, *Nature*. 357: 455-460). Once the virus is integrated into the host genome, it is referred to as a "provirus." The provirus serves as a template for RNA polymerase II and directs the expression of RNA molecules which encode the structural proteins and enzymes needed to produce new viral particles.

Illustrative retroviruses include, but are not limited to: Moloney murine leukemia virus (M-MuLV), Moloney murine sarcoma virus (MoMSV), Harvey murine sarcoma virus (HaMuSV), murine mammary tumor virus (MuMTV), gibbon ape leukemia virus (GaLV), feline leukemia virus (FLV), Spumavirus, Friend murine leukemia virus, Murine Stem Cell Virus (MSCV) and Rous Sarcoma Virus (RSV)) and lentivirus.

As used herein, the term "lentivirus" refers to a group (or genus) of complex retroviruses. Illustrative lentiviruses include, but are not limited to: HIV (human immunodeficiency virus; including HIV type 1, and HIV type 2); visna-maedi virus (VMV) virus; the caprine arthritis-encephalitis virus (CAEV); equine infectious anemia virus (EIAV); feline immunodeficiency virus (FIV); bovine immune deficiency virus (BIV); and simian immunodeficiency virus (SIV). In one embodiment, HIV based vector backbones (i.e., HIV cis-acting sequence elements) are preferred.

Retroviral vectors and more particularly lentiviral vectors may be used in practicing the present invention. Accordingly, the term "retrovirus" or "retroviral vector," as used herein is meant to include "lentivirus" and "lentiviral vectors" respectively.

The term "vector" is used herein to refer to a nucleic acid molecule capable transferring or transporting another nucleic acid molecule. The transferred nucleic acid is generally linked to, e.g., inserted into, the vector nucleic acid molecule. A vector may include sequences that direct autonomous replication in a cell, or may include sequences sufficient to allow integration into host cell DNA. Useful vectors include, for example, plasmids (e.g., DNA plasmids or RNA plasmids), transposons, cosmids, bacterial artificial chromosomes, and viral vectors. Useful viral vectors include, e.g., replication defective retroviruses and lentiviruses.

As will be evident to one of skill in the art, the term "viral vector" is widely used to refer either to a nucleic acid molecule/e.g., a transfer plasmid) that includes virus-derived nucleic acid elements that typically facilitate transfer of the nucleic acid molecule or integration into the genome of a cell or to a viral particle that mediates nucleic acid transfer. Viral particles will typically include various viral components and sometimes also host cell components in addition to nucleic acid(s).

The term viral vector may refer either to a virus or viral particle capable of transferring a nucleic acid into a cell or to the transferred nucleic acid itself. Viral vectors and transfer plasmids contain structural and/or functional genetic elements that are primarily derived from a virus. The term "retroviral vector" refers to a viral vector or plasmid containing structural and functional genetic elements, or portions thereof, that are primarily derived from a retrovirus. The term "lentiviral vector" refers to a viral vector or plasmid containing structural and functional genetic elements, or portions thereof, including LTRs that are primarily derived from a lentivirus. The term "hybrid" refers to a vector, LTR or other nucleic acid containing both retroviral, e.g., lentiviral, sequences and non-lentiviral viral sequences. In one embodiment, a hybrid vector refers to a vector or transfer plasmid comprising retroviral e.g., lentiviral, sequences for reverse transcription, replication, integration and/or packaging.

In particular embodiments, the terms "lentiviral vector," "lentiviral expression vector" may be used to refer to lentiviral transfer plasmids and/or infectious lentiviral particles. Where reference is made herein to elements such as cloning sites, promoters, regulatory elements, heterologous nucleic acids, etc., it is to be understood that the sequences of these elements are present in RNA form in the lentiviral particles of the invention and are present in DNA form in the DNA plasmids of the invention.

At each end of the provirus are structures called "long terminal repeats" or "LTRs." The term "long terminal repeat (LTR)" refers to domains of base pairs located at the ends of retroviral DNAs which, in their natural sequence context, are direct repeats and contain U3, R and U5 regions. LTRs generally provide functions fundamental to the expression of retroviral genes (e.g., promotion, initiation and polyadenylation of gene transcripts) and to viral replication. The LTR contains numerous regulatory signals including transcriptional control elements, polyadenylation signals and sequences needed for replication and integration of the viral genome. The viral LTR is divided into three regions called U3, R and U5. The U3 region contains the enhancer and promoter elements. The U5 region is the sequence between the primer binding site and the R region and contains the polyadenylation sequence. The R (repeat) region is flanked by the U3 and U5 regions. The LTR composed of U3, R and U5 regions and appears at both the 5' and 3' ends of the viral genome. Adjacent to the 5' LTR are sequences necessary for reverse transcription of the genome (the tRNA primer binding site) and for efficient packaging of viral RNA into particles (the Psi site).

As used herein, the term "packaging signal" or "packaging sequence" refers to sequences located within the retroviral genome which are required for insertion of the viral RNA into the viral capsid or particle, see e.g., Clever et al, 1995. *J. of Virology*, Vol. 69, No. 4; pp. 2101-2109. Several retroviral vectors use the minimal packaging signal (also referred to as the psi [Ψ] or [Ψ+] sequence) needed for encapsidation of the viral genome. Thus, as used herein, the terms "packaging sequence," "packaging signal," "psi" and the symbol "Ψ," are used in reference to the non-coding sequence required for encapsidation of retroviral RNA strands during viral particle formation.

In various embodiments, vectors comprise modified 5' LTR and/or 3' LTRs. Modifications of the 3' LTR are often made to improve the safety of lentiviral or retroviral systems by rendering viruses replication-defective. As used herein, the term "replication-defective" refers to virus that is not capable of complete, effective replication such that infective virions are not produced (e.g., replication-defective lentiviral progeny). The term "replication-competent" refers to wild-type virus or mutant virus that is capable of replication, such that viral replication of the virus is capable of producing infective virions (e.g., replication-competent lentiviral progeny).

"Self-inactivating" (SIN) vectors refers to replication-defective vectors, e.g., retroviral or lentiviral vectors, in which the right (3') LTR enhancer-promoter region, known as the U3 region, has been modified (e.g., by deletion and/or substitution) to prevent viral transcription beyond the first round of viral replication. This is because the right (3') LTR U3 region is used as a template for the left (5') LTR U3 region during viral replication and, thus, the viral transcript cannot be made without the U3 enhancer-promoter. In a further embodiment of the invention, the 3' LTR is modified such that the U5 region is replaced, for example, with a heterologous or synthetic poly(A) sequence, one or more insulator elements, and/or an inducible promoter. It should be noted that modifications to the LTRs such as modifications to the 3' LTR, the 5' LTR, or both 3' and 5' LTRs, are also included in the invention.

An additional safety enhancement is provided by replacing the U3 region of the 5' LTR with a heterologous promoter to drive transcription of the viral genome during production of viral particles. Examples of heterologous promoters which can be used include, for example, viral simian virus 40 (SV40) (e.g., early or late), cytomegalovirus (CMV) (e.g., immediate early), Moloney murine leukemia virus (MoMLV), Rous sarcoma virus (RSV), and herpes simplex virus (HSV) (thymidine kinase) promoters. Typical promoters are able to drive high levels of transcription in a Tat-independent manner. This replacement reduces the possibility of recombination to generate replication-competent virus because there is no complete U3 sequence in the virus production system. In certain embodiments, the heterologous promoter may be inducible, such that transcription of all or part of the viral genome will occur only when one or more induction factors are present. Induction factors include, but are not limited to, one or more chemical compounds or physiological conditions, e.g., temperature or pH, in which the host cells are cultured.

In some embodiments, viral vectors comprise a TAR element. The term "TAR" refers to the "trans-activation response" genetic element located in the R region of lentiviral (e.g., HIV) LTRs. This element interacts with the lentiviral trans-activator (tat) genetic element to enhance viral replication. However, this element is not required in embodiments wherein the U3 region of the 5' LTR is replaced by a heterologous promoter.

The "R region" refers to the region within retroviral LTRs beginning at the start of the capping group (i.e., the start of transcription) and ending immediately prior to the start of the poly A tract. The R region is also defined as being flanked by the U3 and U5 regions. The R region plays a role during reverse transcription in permitting the transfer of nascent DNA from one end of the genome to the other.

As used herein, the term "FLAP element" refers to a nucleic acid whose sequence includes the central polypurine tract and central termination sequences (cPPT and CTS) of a retrovirus, e.g., HIV-1 or HIV-2. Suitable FLAP elements are described in U.S. Pat. No. 6,682,907 and in Zennou, et al., 2000, Cell, 101:173. During HIV-1 reverse transcription, central initiation of the plus-strand DNA at the central polypurine tract (cPPT) and central termination at the central termination sequence (CTS) lead to the formation of a three-stranded DNA structure: the HIV-1 central DNA flap. While not wishing to be bound by any theory, the DNA flap may act as a cis-active determinant of lentiviral genome nuclear import and/or may increase the titer of the virus. In particular embodiments, the retroviral or lentiviral vector backbones comprise one or more FLAP elements upstream or downstream of the heterologous genes of interest in the vectors. For example, in particular embodiments a transfer plasmid includes a FLAP element. In one embodiment, a vector of the invention comprises a FLAP element isolated from HIV-1.

In one embodiment, retroviral or lentiviral transfer vectors comprise one or more export elements. The term "export element" refers to a cis-acting post-transcriptional regulatory element which regulates the transport of an RNA transcript from the nucleus to the cytoplasm of a cell. Examples of RNA export elements include, but are not limited to, the human immunodeficiency virus (HIV) rev response element (RRE) (see e.g., Cullen et al., 1991. J. Virol. 65: 1053; and Cullen et al., 1991. Cell 58: 423), and the hepatitis B virus post-transcriptional regulatory element (HPRE). Generally, the RNA export element is placed within the 3' UTR of a gene, and can be inserted as one or multiple copies.

In particular embodiments, expression of heterologous sequences in viral vectors is increased by incorporating posttranscriptional regulatory elements, efficient polyadenylation sites, and optionally, transcription termination signals into the vectors. A variety of posttranscriptional regulatory elements can increase expression of a heterologous nucleic acid at the protein, e.g., woodchuck hepatitis virus posttranscriptional regulatory element (WPRE; Zufferey et al., 1999, J. Virol., 73:2886); the posttranscriptional regulatory element present in hepatitis B virus (HPRE) (Huang and Yen, 1995, Mol. Cell. Biol, 5:3864); and the like (Liu et al, 1995, Genes Dev., 9:1766). In particular embodiments, vectors of the invention lack or do not comprise a posttranscriptional regulatory element such as a WPRE or HPRE because in some instances these elements increase the risk of cellular transformation and/or do not substantially or significantly increase the amount of mRNA transcript or increase mRNA stability. Therefore, in some embodiments, vectors of the invention lack or do not comprise a WPRE or HPRE as an added safety measure.

Elements directing the efficient termination and polyadenylation of the heterologous nucleic acid transcripts increases heterologous gene expression. Transcription termination signals are generally found downstream of the polyadenylation signal. The term "polyA site" or "polyA sequence" as used herein denotes a DNA sequence which directs both the termination and polyadenylation of the nascent RNA transcript by RNA polymerase II. Efficient polyadenylation of the recombinant transcript is desirable as transcripts lacking a poly A tail are unstable and are rapidly degraded. Illustrative examples of polyA signals that can be used in a vector of the invention, include an ideal polyA sequence (e.g., AATAAA, ATTAAA AGTAAA), a bovine growth hormone polyA sequence (BGHpA), a rabbit β-globin polyA sequence (rPgpA), or another suitable heterologous or endogenous polyA sequence known in the art.

In certain embodiments, a retroviral or lentiviral vector further comprises one or more insulator elements. Insulators elements may contribute to protecting lentivirus-expressed sequences, e.g., therapeutic polypeptides, from integration site effects, which may be mediated by cis-acting elements present in genomic DNA and lead to deregulated expression of transferred sequences (i.e., position effect; see, e.g., Burgess-Beusse et al, 2002, Proc. Natl. Acad. Sci., USA, 99:16433; and Zhan et al, 2001, Hum. Genet., 109:471). In some embodiments, transfer vectors comprise one or more insulator element the 3' LTR and upon integration of the provirus into the host genome, the provirus comprises the one or more insulators at both the 5' LTR or 3' LTR, by virtue of duplicating the 3' LTR. Suitable insulators for use in the invention include, but are not limited to, the chicken β-globin insulator (see Chung et al, 1993. Cell 74:505; Chung et al, 1997. PNAS 94:575; and Bell et al, 1999. Cell 98:387, incorporated by reference herein). Examples of insulator elements include, but are not limited to, an insulator from an β-globin locus, such as chicken HS4.

According to certain specific embodiments of the invention, most or all of the viral vector backbone sequences are derived from a lentivirus, e.g., HIV-1. However, it is to be understood that many different sources of lentiviral sequences can be used, and numerous substitutions and alterations in certain of the lentiviral sequences may be accommodated without impairing the ability of a transfer vector to perform the functions described herein. Moreover, a variety of lentiviral vectors are known in the art, see Naldini et al, (1996a, 1996b, and 1998); Zufferey et al, (1997); Dull et al, 1998, U.S. Pat. Nos. 6,013,516; and 5,994,136, many of which may be adapted to produce a viral vector or transfer plasmid of the present invention.

As used herein, the term "compound" encompasses small organic molecule, prostaglandins, cAMP enhancers, Wnt pathway agonists, cAMP/PI3K/AKT pathway agonists, $Ca^{2+}$ second messenger pathway agonists, nitric oxide (NO)/angiotensin signaling agonists and inorganic chemicals, including without limitation, all analogs and derivatives thereof.

A "small molecule," "small organic molecule," or "small molecule compound" refers to a low molecular weight compound that has a molecular weight of less than about 5 kD, less than about 4 kD, less than about 3 kD, less than about 2 kD, less than about 1 kD, or less than about 0.5 kD. In particular embodiments, small molecules can include, nucleic acids, peptides, peptidomimetics, peptoids, other small organic compounds or drugs, and the like. Libraries of chemical and/or biological mixtures, such as fungal, bacterial, or algal extracts, are known in the art and can be screened with any of the assays of the invention. Examples of methods for the synthesis of molecular libraries can be found in: (Carell et al, 1994a; Carell et al, 1994b; Cho et al, 1993; DeWitt et al, 1993; Gallop et al, 1994; Zuckermann et al, 1994).

Libraries of compounds may be presented in solution (Houghten et al, 1992) or on beads (Lam et al, 1991), on chips (Fodor et al, 1993), bacteria, spores (Ladner et al., U.S. Pat. No. 5,223,409, 1993), plasmids (Cull et al, 1992) or on phage (Cwirla et al, 1990; Devlin et al, 1990; Felici et al, 1991; Ladner et al, U.S. Pat. No. 5,223,409, 1993; Scott and Smith, 1990). The invention disclosed herein encompasses the use of different libraries for the identification of small molecules that increase prostaglandin EP receptor signaling at any point in the cell signaling pathway. Libraries useful for the purposes of the invention include, but are not limited to, (1) chemical libraries, (2) natural product libraries, and (3) combinatorial libraries comprised of random peptides, oligonucleotides and/or organic molecules.

Chemical libraries consist of structural analogs and derivatives of known compounds or compounds that are identified as "hits" or "leads" via natural product screening. Natural product libraries are derived from collections of microorganisms, animals, plants, or marine organisms which are used to create mixtures for screening by: (1) fermentation and extraction of broths from soil, plant or marine microorganisms or (2) extraction of plants or marine organisms. Natural product libraries include polyketides, non-ribosomal peptides, and variants (non-naturally occurring) thereof. For a review, see, Cane, D. E., et al., (1998) Science 282:63-68. Combinatorial libraries are composed of large numbers of peptides, oligonucleotides or organic compounds as a mixture. They are relatively easy to prepare by traditional automated synthesis methods, PCR, cloning or proprietary synthetic methods. Of particular interest are peptide and oligonucleotide combinatorial libraries.

More specifically, a combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

For a review of combinatorial chemistry and libraries created therefrom, see Hue, I. and Nguyen, R. (2001) *Comb. Chem. High Throughput Screen* 4:53-74; Lepre, C A. (2001) *Drug Discov. Today* 6:133-140; Peng, S. X. (2000) *Biomed. Chromatogr.* 14:430-441; Bohm, H. J. and Stahl, M. (2000) *Curr. Opin. Chem. Biol.* 4:283-286; Barnes, C and Balasubramanian, S. (2000) *Curr. Opin. Chem. Biol.* 4:346-350; Lepre, Enjalbal, C, et al, (2000) *Mass Septrom Rev.* 19:139-161; Hall, D. G., (2000) *Nat. Biotechnol.* 18:262-262; Lazo, J. S., and Wipf, P. (2000) *J. Pharmacol. Exp. Ther.* 293:705-709; Houghten, R. A., (2000) *Ann. Rev. Pharmacol. Toxicol.* 40:273-282; Kobayashi, S. (2000) *Curr. Opin. Chem. Biol.* (2000) 4:338-345; Kopylov, A. M. and Spiridonova, V. A. (2000) *Mol. Biol.* (Mock) 34:1097-1 113; Weber, L. (2000) *Curr. Opin. Chem. Biol.* 4:295-302; Dolle, R. E. (2000) *J. Comb. Chem.* 2:383-433; Floyd, C D., et al, (1999) *Prog. Med. Chem.* 36:91-168; Kundu, B., et al, (\999) *Prog. Drug Res.* 53:89-156; Cabilly, S. (1999) *Mol. Biotechnol.* 12:143-148; Lowe, G. (1999) *Nat. Prod. Rep.* 16:641-651; Dolle, R. E. and Nelson, K. H. (1999) *J. Comb. Chem.* 1:235-282; Czarnick, A. W. and Keene, J. D. (1998) *Curr. Biol.* 8:R705-R707; Dolle, R. E. (1998) *Mol. Divers.* 4:233-256; Myers, P. L., (1997) *Curr. Opin. Biotechnol.* 8:701-707; and Pluckthun, A. and Cortese, R. (1997) *Biol. Chem.* 378:443.

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd., Moscow, RU, 3D Pharmaceuticals, Exton, Pa., Martek Biosciences, Columbia, Md., etc.).

As used herein, the term "metabolic precursor" refers to a form of a compound that metabolizes into a desired compound.

As used herein, the term "metabolite" refers to a resultant form of a compound that has been metabolized.

In reference to chemicals, such as organic chemicals, "analog" or "derivative" relates to a chemical molecule that is similar to another chemical substance in structure and function, often differing structurally by a single element or group, but may differ by differ by modification of more than one group (e.g., 2, 3, or 4 groups) if it retains the same function as the parental chemical. Such modifications are routine to persons skilled in the art, and include, for example, additional or substituted chemical moieties, such as esters or amides of an acid, protecting groups such as a benzyl group for an alcohol or thiol, and tert-butoxycarbonyl groups for an amine. Also included are modifications to alkyl side chains, such as alkyl substitutions (e.g., methyl, dimethyl, ethyl, etc.), modifications to the level of saturation or unsaturation of side chains, and the addition of modified groups such as substituted phenyl and phenoxy. Derivatives may also include conjugates, such as biotin or avidin moieties, enzymes such as horseradish peroxidase and the like, and including radio-labeled, bioluminescent, chemoluminescent, or fluorescent moieties. Also, moieties may be added to the agents described herein to alter their pharmacokinetic properties, such as to increase half-life in vivo or ex vivo, or to increase their cell penetration properties, among other desirable properties. Also included are prodrugs, which are known to enhance numerous desirable qualities of pharmaceuticals (e.g., solubility, bioavailability, manufacturing, etc.) (see, e.g., WO/2006/047476 for exemplary EP agonist prodrugs, which is incorporated by reference for its disclosure of such agonists).

As used herein, the terms "polynucleotide" or "nucleic acid" refers to messenger RNA (mRNA), RNA, genomic RNA (gRNA), plus strand RNA (RNA(+)), minus strand RNA (RNA(-)), genomic DNA (gDNA), complementary DNA (cDNA) or DNA. Polynucleotides include single and double stranded polynucleotides. Preferably, polynucleotides of the invention include polynucleotides or variants having at least about 50%, 55%, 60%, 65%, 70%, 75%, 80%, 85%, 90%, 95%, 96%, 97%, 98%, 99% or 100% sequence identity to any of the reference sequences described herein (see, e.g., Sequence Listing), typically where the variant maintains at least one biological activity of the reference sequence. In various illustrative embodiments, the present invention contemplates, in part, viral vector and transfer plasmid polynucleotide sequences and compositions comprising the same. In particular embodiments, the invention provides polynucleotides encoding one or more therapeutic polypeptides and/or other genes of interest. In particular embodiments, the present invention provides polynucleotides encoding a globin polypeptide or an ATP-binding cassette, sub-family D (ALD), member 1 (ABCD1) polypeptide, as discussed elsewhere herein.

As used herein, the terms "polynucleotide variant" and "variant" and the like refer to polynucleotides displaying substantial sequence identity with a reference polynucleotide sequence or polynucleotides that hybridize with a reference sequence under stringent conditions that are defined hereinafter. These terms include polynucleotides in which one or more nucleotides have been added or deleted, or replaced with different nucleotides compared to a reference polynucleotide. In this regard, it is well understood in the art that certain alterations inclusive of mutations, additions, deletions and substitutions can be made to a reference polynucleotide whereby the altered polynucleotide retains the biological function or activity of the reference polynucleotide.

As used herein, the term "isolated" means material, e.g., a polynucleotide, a polypeptide, a cell, that is substantially or essentially free from components that normally accompany it in its native state. In particular embodiments, the term "obtained" or "derived" is used synonymously with isolated. For example, an "isolated polynucleotide," as used herein, refers to a polynucleotide that has been purified from the sequences which flank it in a naturally-occurring state, e.g., a DNA fragment that has been removed from the sequences that are normally adjacent to the fragment.

Terms that describe the orientation of polynucleotides include: 5' (normally the end of the polynucleotide having a free phosphate group) and 3' (normally the end of the polynucleotide having a free hydroxyl (OH) group). Polynucleotide sequences can be annotated in the 5' to 3' orientation or the 3' to 5' orientation.

The terms "complementary" and "complementarity" refer to polynucleotides (i.e., a sequence of nucleotides) related by the base-pairing rules. For example, the complementary strand of the DNA sequence 5A G T C A T G 3' is 3' T C A G T A C 5'. The latter sequence is often written as the reverse complement with the 5' end on the left and the 3' end on the right, 5' C A T G A C T 3'. A sequence that is equal to its reverse complement is said to be a palindromic sequence. Complementarity can be "partial," in which only some of the nucleic acids' bases are matched according to the base pairing rules. Or, there can be "complete" or "total" complementarity between the nucleic acids.

The term "nucleic acid cassette" as used herein refers to genetic sequences within the vector which can express an RNA, and subsequently a polypeptide. In one embodiment, the nucleic acid cassette contains a gene(s)-of-interest, e.g., a polynucleotide(s)-of-interest. In another embodiment, the nucleic acid cassette contains one or more expression control sequences and a gene(s)-of-interest, e.g., a polynucleotide(s)-of-interest. Vectors may comprise one, two, three, four, five or more nucleic acid cassettes. The nucleic acid cassette is positionally and sequentially oriented within the vector such that the nucleic acid in the cassette can be transcribed into RNA, and when necessary, translated into a protein or a polypeptide, undergo appropriate post-translational modifications required for activity in the transformed cell, and be translocated to the appropriate compartment for biological activity by targeting to appropriate intracellular compartments or secretion into extracellular compartments. Preferably, the cassette has its 3' and 5' ends adapted for ready insertion into a vector, e.g., it has restriction endonuclease sites at each end. In a preferred embodiment of the invention, the nucleic acid cassette contains the sequence of a therapeutic gene used to treat, prevent, or ameliorate a genetic disorder, such as a hematopoietic disorder. The cassette can be removed and inserted into a plasmid or viral vector as a single unit.

Polynucleotides include a polynucleotide(s)-of-interest. As used herein, the term "polynucleotide(s)-of-interest" refers to one or more polynucleotides, e.g., a polynucleotide encoding a polypeptide (i.e., a polypeptide-of-interest), inserted into an expression vector that is desired to be expressed. In preferred embodiments, vectors and/or plasmids of the present invention comprise one or more polynucleotides-of-interest, e.g., a globin gene or ABCD1 gene. In certain embodiments, a polynucleotide-of-interest encodes a polypeptide that provides a therapeutic effect in the treatment, prevention, or amelioration of a hematopoietic disease or disorder, which may be referred to as a "therapeutic polypeptide," e.g., a globin gene. See, for example U.S. Pat. Nos. 6,051,402 and 7,901,671, the full disclosure and claims of which are specifically incorporated herein by reference. See e.g., SEQ ID NOs: 1, 5, 10, and 14.

In certain other embodiments, a polynucleotide-of-interest encodes a polypeptide that provides a therapeutic effect in the treatment, prevention, or amelioration of an adrenoleukodystrophy or adrenomyeloneuropathy, which may be referred to as a "therapeutic polypeptide," e.g., an ABCD1 gene. See, e.g., SEQ ID NOs: 16-17. See, for example, U.S. Pat. Nos. 5,869,039; and 6,013,769, the full disclosure and claims of which are specifically incorporated herein by reference.

The term "globin" as used herein, means all proteins or protein subunits that are capable of covalently or noncovalently binding a heme moiety, and can therefore transport or store oxygen. Subunits of vertebrate and invertebrate hemoglobins, vertebrate and invertebrate myoglobins or mutants thereof are included by the term globin. Examples of globins include a-globin or variant thereof, β-globin or variant thereof, a γ-globin or a variant thereof, and δ-globin or a variant thereof.

In one embodiment, the polynucleotide-of-interest is a gene that encodes a polypeptide that provides a therapeutic function for the treatment of a hemoglobinopathy, e.g., a-globin, β-globin or P-globinA-T87Q. Polynucleotides-of-interest, and polypeptides encoded therefrom, include both polynucleotides that encode wild-type polypeptides, as well as functional variants and fragments thereof. In particular embodiments, a functional variant has at least 80%, at least 90%, at least 95%), or at least 99% identity to a corresponding wild-type reference polynucleotide or polypeptide sequence. In certain embodiments, a functional variant or fragment has at least 50%, at least 60%, at least 70%, at least 80%, at least 90%, at least a 100%, or at least 110% or more of a biological activity of a corresponding wild-type polypeptide. Representative polynucleotides sequences suitable for use in the present invention include, but are not limited to, polynucleotides encoding a-globin, β-globin, and P-globinA-T87Q.

The polynucleotides of the present invention, regardless of the length of the coding sequence itself, may be combined with other DNA sequences, such as promoters and/or enhancers, untranslated regions (UTRs), Kozak sequences, polyadenylation signals, additional restriction enzyme sites, multiple cloning sites, internal ribosomal entry sites (IRES), recombinase recognition sites (e.g., LoxP, FRT, and Att sites), termination codons, transcriptional termination signals, and polynucleotides encoding self-cleaving polypeptides, epitope tags, as disclosed elsewhere herein or as known in the art, such that their overall length may vary considerably. It is therefore contemplated that a polynucleotide fragment of almost any length may be employed, with the total length preferably being limited by the ease of preparation and use in the intended recombinant DNA protocol.

The term "expression control sequence" refers to a polynucleotide sequence that comprises one or more promoters, enhancers, or other transcriptional control elements or combinations thereof that are capable of directing, increasing, regulating, or controlling the transcription or expression of an operatively linked polynucleotide. In particular embodiments, vectors of the invention comprise one or more expression control sequences that are specific to particular cells, cell types, or cell lineages e.g., target cells; that is, expression of polynucleotides operatively linked to an expression control sequence specific to particular cells, cell types, or cell lineages is expressed in target cells and not in other non-target cells. Each one of the one or more expression control sequences in a vector that are cell specific may express in the same or different cell types depending on the therapy desired. In preferred embodiments, vectors comprise one or more expression control sequences specific to hematopoietic cells, e.g., hematopoietic stem or progenitor cells. In other preferred embodiments, vectors comprise one or more expression control sequences specific to erythroid cells.

The term "promoter" as used herein refers to a recognition site of a polynucleotide (DNA or RNA) to which an RNA polymerase binds. The term "enhancer" refers to a segment of DNA which contains sequences capable of providing enhanced transcription and in some instances can function independent of their orientation relative to another control sequence. An enhancer can function cooperatively or additively with promoters and/or other enhancer elements. The term "promoter/enhancer" refers to a segment of DNA which contains sequences capable of providing both promoter and enhancer functions.

In particular embodiments, a vector of the invention comprises exogenous, endogenous, or heterologous control sequences such as promoters and/or enhancers. An "endogenous" control sequence is one which is naturally linked to a given gene in the genome. An "exogenous" control sequence is one which is placed in juxtaposition to a gene by means of genetic manipulation (i.e., molecular biological techniques) such that transcription of that gene is directed by the linked enhancer/promoter. A "heterologous" control sequence is an exogenous sequence that is from a different species than the cell being genetically manipulated. A "synthetic" control sequence may comprise elements of one more endogenous and/or exogenous sequences, and/or sequences determined in vitro or in silico that provide optimal promoter and/or enhancer activity for the particular gene therapy.

The term "operably linked", refers to a juxtaposition wherein the components described are in a relationship permitting them to function in their intended manner. In one embodiment, the term refers to a functional linkage between a nucleic acid expression control sequence (such as a promoter, and/or enhancer or other expression control sequence) and a second polynucleotide sequence, e.g., a polynucleotide-of-interest, wherein the expression control sequence directs transcription of the nucleic acid corresponding to the second sequence.

As used herein, the term "constitutive expression control sequence" refers to a promoter, enhancer, or promoter/enhancer that continually or continuously allows for transcription of an operably linked sequence. A constitutive expression control sequence may be a "ubiquitous" promoter, enhancer, or promoter/enhancer that allows expression in a wide variety of cell and tissue types or a "cell specific," "cell type specific," "cell lineage specific," or "tissue specific" promoter, enhancer, or promoter/enhancer that allows expression in a restricted variety of cell and tissue types, respectively. Illustrative ubiquitous expression control sequences include, but are not limited to, a cytomegalovirus (CMV) immediate early promoter, a viral simian virus 40 (SV40) (e.g., early or late), a Moloney murine leukemia virus (MoMLV) LTR promoter, a Rous sarcoma virus (RSV) LTR, a herpes simplex virus (HSV) (thymidine kinase) promoter, H5, P7.5, and PI 1 promoters from vaccinia virus, an elongation factor 1-alpha (EF1a) promoter, early growth response 1 (EGR1), ferritin H (FerH), ferritin L (FerL), Glyceraldehyde 3-phosphate dehydrogenase (GAPDH), eukaryotic translation initiation factor 4A1 (EIF4A1), heat shock 70 kDa protein 5 (HSPAS), heat shock protein 90 kDa beta, member 1 (HSP90B1), heat shock protein 70 kDa (HSP70), β-kinesin (β-KIN), the human ROSA 26 locus (Irions et al, (2007) *Nature Biotechnology* 25, 1477-1482), a Ubiquitin C promoter (UBC), a phosphoglycerate kinase-1 (PGK) promoter, a cytomegalovirus enhancer/chicken β-actin (CAG) promoter, and a β-actin promoter.

In a particular embodiment, it may be desirable to use a cell, cell type, cell lineage or tissue specific expression control sequence to achieve cell type specific, lineage specific, or tissue specific expression of a desired polynucleotide sequence (e.g., to express a particular nucleic acid encoding a polypeptide in only a subset of cell types, cell lineages, or tissues or during specific stages of development).

Illustrative examples of tissue specific promoters include, but are not limited to: an B29 promoter (B cell expression), a runt transcription factor (CBFa2) promoter (stem cell specific expression), an CD 14 promoter (monocytic cell expression), an CD43 promoter (leukocyte and platelet expression), an CD45 promoter (hematopoietic cell expression), an CD68 promoter (macrophage expression), a CYP450 3A4 promoter (hepatocyte expression), an desmin promoter (muscle expression), an elastase 1 promoter (pancreatic acinar cell expression, an endoglin promoter (endothelial cell expression), a fibroblast specific protein 1 promoter (FSP1) promoter (fibroblast cell expression), a fibronectin promoter (fibroblast cell expression), a fms-related tyrosine kinase 1 (FLT1) promoter (endothelial cell expression), a glial fibrillary acidic protein (GFAP) promoter (astrocyte expression), an insulin promoter (pancreatic beta cell expression), an integrin, alpha 2b (ITGA2B) promoter (megakaryocytes), an intracellular adhesion molecule 2 (ICAM-2) promoter (endothelial cells), an interferon beta (IFN-β) promoter (hematopoietic cells), a keratin 5 promoter (keratinocyte expression), a myoglobin (MB) promoter (muscle expression), a myogenic differentiation 1 (MYOD1) promoter (muscle expression), a nephrin promoter (podocyte expression), a bone gamma-carboxyglutamate protein 2 (OG-2) promoter (osteoblast expression), an 3-oxoacid CoA transferase 2B (Oxct2B) promoter, (haploid-spermatid expression), a surfactant protein B (SP-B) promoter (lung expression), a synapsin promoter (neuron expression), a Wiskott-Aldrich syndrome protein (WASP) promoter (hematopoietic cell expression).

In one embodiment, a vector of the present invention comprises one or more hematopoietic cell or tissue specific promoters and/or enhancers selected from the group consisting of: a human β-globin promoter; a human β-globin LCR; and a human a-globin HS40 enhancer and an ankyrin-1 promoter, operably linked to a polynucleotide encoding a globin polypeptide.

In another embodiment, a vector of the present invention comprises a promoter active in a microglial cell, operably linked to a polynucleotide encoding an ATP-binding cassette, sub-family D, member 1 (ABCD1) polypeptide. In certain embodiments, the promoter comprises a myeloproliferative sarcoma virus enhancer, negative control region deleted, d1587rev primer-binding site substituted (MND) promoter or transcriptionally active fragment thereof.

As used herein, "conditional expression" may refer to any type of conditional expression including, but not limited to, inducible expression; repressible expression; expression in cells or tissues having a particular physiological, biological, or disease state, etc. This definition is not intended to exclude cell type or tissue specific expression. Certain embodiments of the invention provide conditional expression of a polynucleotide-of-interest, e.g., expression is controlled by subjecting a cell, tissue, organism, etc., to a treatment or condition that causes the polynucleotide to be expressed or that causes an increase or decrease in expression of the polynucleotide encoded by the polynucleotide-of-interest.

Illustrative examples of inducible promoters/systems include, but are not limited to, steroid-inducible promoters such as promoters for genes encoding glucocorticoid or estrogen receptors (inducible by treatment with the corresponding hormone), metallothionine promoter (inducible by treatment with various heavy metals), MX-1 promoter (inducible by interferon), the "GeneSwitch" mifepristone-regulatable system (Sirin et al., (2003) Gene, 323:67), the cumate inducible gene switch (WO 2002/088346), tetracycline-dependent regulatory systems, etc.

Conditional expression can also be achieved by using a site specific DNA recombinase. According to certain embodiments of the invention the vector comprises at least one (typically two) site(s) for recombination mediated by a site specific recombinase. As used herein, the terms "recombinase" or "site specific recombinase" include excisive or integrative proteins, enzymes, co-factors or associated proteins that are involved in recombination reactions involving one or more recombination sites (e.g., two, three, four, five, seven, ten, twelve, fifteen, twenty, thirty, fifty, etc.), which may be wild-type proteins (see Landy, (1993) Current Opinion in Biotechnology 3:699-707), or mutants, derivatives (e.g., fusion proteins containing the recombination protein sequences or fragments thereof), fragments, and variants thereof. Illustrative examples of recombinases suitable for use in particular embodiments of the present invention include, but are not limited to: Cre, Int, IHF, Xis, Flp, Fis, Hin, Gin, OC31, Cin, Tn3 resolvase, TndX, XerC, XerD, TnpX, Hjc, Gin, SpCCEl, and ParA.

The vectors may comprise one or more recombination sites for any of a wide variety of site specific recombinases. It is to be understood that the target site for a site specific recombinase is in addition to any site(s) required for integration of a vector, e.g., a retroviral vector or lentiviral vector. As used herein, the terms "recombination sequence," "recombination site," or "site specific recombination site" refer to a particular nucleic acid sequence to which a recombinase recognizes and binds.

For example, one recombination site for Cre recombinase is loxP which is a 34 base pair sequence comprising two 13 base pair inverted repeats (serving as the recombinase binding sites) flanking an 8 base pair core sequence (see FIG. 1 of Sauer, B., (1994) Current Opinion in Biotechnology 5:521-527). Other exemplary loxP sites include, but are not limited to: lox51 1 (Hoess et al, 1996; Bethke and Sauer, 1997), lox5171 (Lee and Saito, 1998), lox2272 (Lee and Saito, 1998), m2 (Langer et al, 2002), lox71 (Albert et al, 1995), and lox66 (Albert et al, 1995).

Suitable recognition sites for the FLP recombinase include, but are not limited to: FRT (McLeod, et al, 1996), F1, F2, F3 (Schlake and Bode, 1994), F4, F5 (Schlake and Bode, 1994), FRT(LE) (Senecoff et al, 1988), FRT(RE) (Senecoff et al, 1988).

Other examples of recognition sequences are the attB, attP, attL, and attR sequences, which are recognized by the recombinase enzyme λ Integrase, e.g., phi-c3 1. The (pC 3 1 SSR mediates recombination only between the heterotypic sites attB (34 bp in length) and attP (39 bp in length) (Groth et al, 2000). attB and attP, named for the attachment sites for the phage integrase on the bacterial and phage genomes, respectively, both contain imperfect inverted repeats that are likely bound by cpC31 homodimers (Groth et al, 2000). The product sites, attL and attR, are effectively inert to further cpC31-mediated recombination (Belteki et al, 2003), making the reaction irreversible. For catalyzing insertions, it has been found that attB-bearing DNA inserts into a genomic attP site more readily than an attP site into a genomic attB site (Thyagarajan et al, 2001; Belteki et al, 2003). Thus, typical strategies position by homologous recombination an attP-bearing "docking site" into a defined locus, which is then partnered with an attB-bearing incoming sequence for insertion.

As used herein, an "internal ribosome entry site" or "IRES" refers to an element that promotes direct internal ribosome entry to the initiation codon, such as ATG, of a cistron (a protein encoding region), thereby leading to the cap-independent translation of the gene. See, e.g., Jackson et al, (1990) Trends Biochem Sci 15(12):477-83) and Jackson and Kaminski. (1995) RNA 1(10):985-1000. In particular embodiments, the vectors contemplated by the invention, include one or more polynucleotides-of-interest that encode one or more polypeptides. In particular embodiments, to achieve efficient translation of each of the plurality of polypeptides, the polynucleotide sequences can be separated by one or more IRES sequences or polynucleotide sequences encoding self-cleaving polypeptides.

As used herein, the term "Kozak sequence" refers to a short nucleotide sequence that greatly facilitates the initial binding of mRNA to the small subunit of the ribosome and increases translation. The consensus Kozak sequence is (GCC)RCCATGG, where R is a purine (A or G) (Kozak, (1986) Cell 44(2):283-92, and Kozak, (1987) Nucleic Acids Res. 15(20):8125-48). In particular embodiments, the vectors contemplated by the invention, comprise polynucleotides that have a consensus Kozak sequence and that encode a desired polypeptide.

In certain embodiments, vectors comprise a selection gene, also termed a selectable marker. Typical selection genes encode proteins that (a) confer resistance to antibiotics or other toxins, e.g., ampicillin, neomycin, hygromycin, methotrexate, Zeocin, Blastocidin, or tetracycline, (b) complement auxotrophic deficiencies, or (c) supply critical nutrients not available from complex media, e.g., the gene encoding D-alanine racemase for Bacilli. Any number of selection systems may be used to recover transformed cell lines. These include, but are not limited to, the herpes simplex virus thymidine kinase (Wigler et al, (1977) Cell 11:223-232) and adenine phosphoribosyltransferase (Lowy et al, (1990) Cell 22:817-823) genes which can be employed in tk– or aprt– cells, respectively.

In various embodiments, vectors of the invention are used to increase, establish and/or maintain the expression of one or more polypeptides, e.g., globins. The terms "polypeptide" and "protein" are used interchangeably herein to refer to a polymer of amino acid residues and to variants and synthetic analogues of the same. Thus, these terms apply to amino acid polymers in which one or more amino acid residues are synthetic non-naturally occurring amino acids, such as a chemical analogue of a corresponding naturally occurring amino acid, as well as to naturally-occurring amino acid polymers. Illustrative examples of globin polypeptides suitable for use in the compositions and methods of particular embodiments of the invention, e.g., SEQ ID NOs: 2-4, 6-9, 11-13, and 15. Also, see, e.g., U.S. Pat. Nos. 6,051,402 and 7,901,671, the full disclosure and claims of which are specifically incorporated herein by reference.

Illustrative examples of ABCD 1 polypeptides suitable for use in the compositions and methods of particular embodiments of the invention, e.g., SEQ ID NO: 18. Also, see, e.g., U.S. Pat. Nos. 5,869,039; and 6,013,769, the full disclosure and claims of which are specifically incorporated herein by reference.

Particular embodiments of the invention also include polypeptide "variants." The recitation polypeptide "variant" refers to polypeptides that are distinguished from a reference polypeptide by the addition, deletion, truncations, and/or substitution of at least one amino acid residue, and that retain a biological activity. In certain embodiments, a polypeptide variant is distinguished from a reference polypeptide by one or more substitutions, which may be conservative or non-conservative, as known in the art.

In certain embodiments, a variant polypeptide includes an amino acid sequence having at least about 50%, 55%, 60%, 65%, 70%, 75%, 80%, 85%, 90%, 91%, 92%, 93%, 94%, 95%, 96%, 97%, 98%, 99% or more sequence identity or similarity to a corresponding sequence of a reference polypeptide. In certain embodiments, amino acid additions or deletions occur at the C-terminal end and/or the N-terminal end of the reference polypeptide.

As noted above, polypeptides of the invention may be altered in various ways including amino acid substitutions, deletions, truncations, and insertions. Methods for such manipulations are generally known in the art. For example, amino acid sequence variants of a reference polypeptide can be prepared by mutations in the DNA. Methods for mutagenesis and nucleotide sequence alterations are well known in the art. See, for example, Kunkel (1985) Proc. Natl. Acad. Sci. USA. 82: 488-492, Kunkel et al, (1987) Methods in Enzymol, 154: 367-382, U.S. Pat. No. 4,873,192, Watson, J. D. et al, (1987) Molecular Biology of the Gene, Fourth Edition, Benjamin/Cummings, Menlo Park, Calif., and the references cited therein. Guidance as to appropriate amino acid substitutions that do not affect biological activity of the protein of interest may be found in the model of Dayhoff et al., (1978) Atlas of Protein Sequence and Structure (Natl. Biomed. Res. Found., Washington, D.C.).

A "host cell" includes cells transfected, infected, or transduced in vivo, ex vivo, or in vitro with a recombinant vector or a polynucleotide of the invention. Host cells may include packaging cells, producer cells, and cells infected with viral vectors. In particular embodiments, host cells infected with viral vector of the invention are administered to a subject in need of therapy. In certain embodiments, the term "target cell" is used interchangeably with host cell and refers to transfected, infected, or transduced cells of a desired cell type. In preferred embodiments, the target cell is a stem cell or progenitor cell. In certain preferred embodiments, the target cell is a somatic cell, e.g., adult stem cell, progenitor cell, or differentiated cell. In particular preferred embodiments, the target cell is a hematopoietic cell, e.g., a hematopoietic stem or progenitor cell. Further therapeutic target cells are discussed, infra.

The term "stem cell" refers to a cell which is an undifferentiated cell capable of (1) long term self-renewal, or the ability to generate at least one identical copy of the original cell, (2) differentiation at the single cell level into multiple, and in some instance only one, specialized cell type and (3) of in vivo functional regeneration of tissues. Stem cells are subclassified according to their developmental potential as totipotent, pluripotent, multipotent and oligo/unipotent. "Self-renewal" refers a cell with a unique capacity to produce unaltered daughter cells and to generate specialized cell types (potency). Self-renewal can be achieved in two ways. Asymmetric cell division produces one daughter cell that is identical to the parental cell and one daughter cell that is different from the parental cell and is a progenitor or differentiated cell. Asymmetric cell division does not increase the number of cells. Symmetric cell division produces two identical daughter cells. "Proliferation" or "expansion" of cells refers to symmetrically dividing cells.

As used herein, the term "totipotent" means the ability of a cell to form all cell lineages of an organism. For example, in mammals, only the zygote and the first cleavage stage blastomeres are totipotent. As used herein, the term "pluripotent" means the ability of a cell to form all lineages of the body or soma (i.e., the embryo proper). For example, embryonic stem cells are a type of pluripotent stem cells that are able to form cells from each of the three germs layers, the ectoderm, the mesoderm, and the endoderm. As used herein, the term "multipotent" refers to the ability of an adult stem cell to form multiple cell types of one lineage. For example, hematopoietic stem cells are capable of forming all cells of the blood cell lineage, e.g., lymphoid and myeloid cells. As used herein, the term "oligopotent" refers to the ability of an adult stem cell to differentiate into only a few different cell types. For example, lymphoid or myeloid stem cells are capable of forming cells of either the lymphoid or myeloid lineages, respectively. As used herein, the term "unipotent" means the ability of a cell to form a single cell type. For example, spermatogonial stem cells are only capable of forming sperm cells.

As used herein, the term "progenitor" or "progenitor cells" refers to cells have the capacity to self-renew and to differentiate into more mature cells. Many progenitor cells differentiate along a single lineage, but may have quite extensive proliferative capacity.

Hematopoietic stem cells (HSCs) give rise to committed hematopoietic progenitor cells (HPCs) that are capable of generating the entire repertoire of mature blood cells over the lifetime of an organism. The term "hematopoietic stem cell" or "HSC" refers to multipotent stem cells that give rise to the all the blood cell types of an organism, including myeloid (e.g., monocytes and macrophages, neutrophils, basophils, eosinophils, erythrocytes, megakaryocytes/platelets, dendritic cells), and lymphoid lineages (e.g., T-cells, B-cells, NK-cells), and others known in the art (See Fei, R., et al, U.S. Pat. No. 5,635,387; McGlave, et al, U.S. Pat. No. 5,460,964; Simmons, P., et al, U.S. Pat. No. 5,677,136; Tsukamoto, et al, U.S. Pat. No. 5,750,397; Schwartz, et al, U.S. Pat. No. 5,759,793; DiGuisto, et al, U.S. Pat. No. 5,681,599; Tsukamoto, et al, U.S. Pat. No. 5,716,827). When transplanted into lethally irradiated animals or humans, hematopoietic stem and progenitor cells can repopulate the erythroid, neutrophil-macrophage, megakaryocyte and lymphoid hematopoietic cell pool.

Large scale viral particle production is often necessary to achieve a reasonable viral titer. Viral particles are produced by transfecting a transfer vector into a packaging cell line that comprises viral structural and/or accessory genes, e.g., gag, pol, env, tat, rev, vif, vpr, vpu, vpx, or nef genes or other retroviral genes.

As used herein, the term "packaging vector" refers to an expression vector or viral vector that lacks a packaging signal and comprises a polynucleotide encoding one, two, three, four or more viral structural and/or accessory genes. Typically, the packaging vectors are included in a packaging cell, and are introduced into the cell via transfection, transduction or infection. Methods for transfection, transduction or infection are well known by those of skill in the art. A retroviral/lentiviral transfer vector of the present invention can be introduced into a packaging cell line, via transfection, transduction or infection, to generate a producer cell or cell line. The packaging vectors of the present invention can be introduced into human cells or cell lines by standard methods including, e.g., calcium phosphate transfection, lipofection or electroporation. In some embodiments, the packaging vectors are introduced into the cells together with a dominant selectable marker, such as neomycin, hygromycin, puromycin, blastocidin, zeocin, thymidine kinase, DHFR, Gln synthetase or ADA, followed by selection in the presence of the appropriate drug and isolation of clones. A selectable marker gene can be linked physically to genes encoding by the packaging vector, e.g., by IRES or self cleaving viral peptides.

Viral envelope proteins (env) determine the range of host cells which can ultimately be infected and transformed by recombinant retroviruses generated from the cell lines. In the case of lentiviruses, such as HIV-1, HIV-2, SIV, FIV and EIV, the env proteins include gp41 and gp120. Preferably, the viral env proteins expressed by packaging cells of the invention are encoded on a separate vector from the viral gag and pol genes, as has been previously described.

Illustrative examples of retroviral-derived env genes which can be employed in the invention include, but are not limited to: MLV envelopes, 10A1 envelope, BAEV, FeLV-B, RD1 14, SSAV, Ebola, Sendai, FPV (Fowl plague virus), and influenza virus envelopes. Similarly, genes encoding envelopes from RNA viruses (e.g., RNA virus families of Picornaviridae, Calciviridae, Astroviridae, Togaviridae, Flaviviridae, Coronaviridae, Paramyxoviridae, Rhabdoviridae, Filoviridae, Orthomyxoviridae, Bunyaviridae, Arenaviridae, Reoviridae, Bimaviridae, Retroviridae) as well as from the DNA viruses (families of Hepadnaviridae, Circoviridae, Parvoviridae, Papovaviridae, Adenoviridae, Herpesviridae, Poxyiridae, and Iridoviridae) may be utilized. Representative examples include, FeLV, VEE, HFVW, WDSV, SFV, Rabies, ALV, BIV, BLV, EBV, CAEV, SNV, ChTLV, STLV, MPMV, SMRV, RAV, FuSV, MH2, AEV, AMV, CT10, and EIAV.

In other embodiments, envelope proteins for pseudotyping a virus of present invention include, but are not limited to any of the following virus: Influenza A such as H1N1, H1N2, H3N2 and H5N1 (bird flu), Influenza B, Influenza C virus, Hepatitis A virus, Hepatitis B virus, Hepatitis C virus, Hepatitis D virus, Hepatitis E virus, Rotavirus, any virus of the Norwalk virus group, enteric adenoviruses, parvovirus, Dengue fever virus, Monkey pox, Mononegavirales, Lyssavirus such as rabies virus, Lagos bat virus, Mokola virus, Duvenhage virus, European bat virus 1 & 2 and Australian bat virus, Ephemerovirus, Vesiculovirus, Vesicular Stomatitis Virus (VSV), Herpesviruses such as Herpes simplex virus types 1 and 2, varicella zoster, cytomegalovirus, Epstein-Bar virus (EBV), human herpesviruses (HHV), human herpesvirus type 6 and 8, Human immunodeficiency virus (HIV), papilloma virus, murine gammaherpesvirus, Arenaviruses such as Argentine hemorrhagic fever virus, Bolivian hemorrhagic fever virus, Sabia-associated hemorrhagic fever virus, Venezuelan hemorrhagic fever virus, Lassa fever virus, Machupo virus, Lymphocytic choriomeningitis virus (LCMV), Bunyaviridiae such as Crimean-Congo hemorrhagic fever virus, Hantavirus, hemorrhagic fever with renal syndrome causing virus, Rift Valley fever virus, Filoviridae (filovirus) including Ebola hemorrhagic fever and Marburg hemorrhagic fever, Flaviviridae including Kaysanur Forest disease virus, Omsk hemorrhagic fever virus, Tick-borne encephalitis causing virus and Paramyxoviridae such as Hendra virus and Nipah virus, variola major and variola minor (smallpox), alphaviruses such as Venezuelan equine encephalitis virus, eastern equine encephalitis virus, western equine encephalitis virus, SARS-associated coronavirus (SARS-CoV), West Nile virus, any encephaliltis causing virus.

In one embodiment, the invention provides packaging cells which produce recombinant retrovirus, e.g., lentivirus, pseudotyped with the VSV-G glycoprotein.

The terms "pseudotype" or "pseudotyping" as used herein, refer to a virus whose viral envelope proteins have been substituted with those of another virus possessing preferable characteristics. For example, HIV can be pseudotyped with vesicular stomatitis virus G-protein (VSV-G) envelope proteins, which allows HIV to infect a wider range of cells because HIV envelope proteins (encoded by the env gene) normally target the virus to CD4+ presenting cells. In a preferred embodiment of the invention, lentiviral envelope proteins are pseudotyped with VSV-G. In one embodiment, the invention provides packaging cells which produce recombinant retrovirus, e.g., lentivirus, pseudotyped with the VSV-G envelope glycoprotein.

As used herein, the term "packaging cell lines" is used in reference to cell lines that do not contain a packaging signal, but do stably or transiently express viral structural proteins and replication enzymes (e.g., gag, pol and env) which are necessary for the correct packaging of viral particles. Any suitable cell line can be employed to prepare packaging cells of the invention. Generally, the cells are mammalian cells. In a particular embodiment, the cells used to produce the packaging cell line are human cells. Suitable cell lines which can be used include, for example, CHO cells, BHK cells, MDCK cells, C3H 10T1/2 cells, FLY cells, Psi-2 cells, BOSC 23 cells, PA317 cells, WEHI cells, COS cells, BSC 1 cells, BSC 40 cells, BMT 10 cells, VERO cells, W138 cells, MRCS cells, A549 cells, HT1080 cells, 293 cells, 293T cells, B-50 cells, 3T3 cells, NIH3T3 cells, HepG2 cells, Saos-2 cells, Huh7 cells, HeLa cells, W163 cells, 211 cells, and 211A cells. In preferred embodiments, the packaging cells are 293 cells, 293T cells, or A549 cells. In another preferred embodiment, the cells are A549 cells.

As used herein, the term "producer cell line" refers to a cell line which is capable of producing recombinant retroviral particles, comprising a packaging cell line and a transfer vector construct comprising a packaging signal. The production of infectious viral particles and viral stock solutions may be carried out using conventional techniques. Methods of preparing viral stock solutions are known in the art and are illustrated by, e.g., Y. Soneoka et al. (1995) *Nucl. Acids Res.* 23:628-633, and N. R. Landau et al. (1992) *J. Virol.* 66:5 110-5 113. Infectious virus particles may be collected from the packaging cells using conventional techniques. For example, the infectious particles can be collected by cell lysis, or collection of the supernatant of the cell culture, as is known in the art. Optionally, the collected virus particles may be purified if desired. Suitable purification techniques are well known to those skilled in the art.

By "enhance" or "promote," or "increase" or "expand" refers generally to the ability of the compositions and/or methods of the invention to elicit, cause, or produce higher numbers of transduced cells compared to the number of cells transduced by either vehicle or a control molecule/composition. In one embodiment, a hematopoietic stem cell transduced with compositions and methods of the present invention comprises an increase in the number of transduced cells compared to existing transduction compositions and methods. Increases in cell transduction, can be ascertained using methods known in the art, such as reporter assays, RT-PCR, and cell surface protein expression, among others. An "increased" or "enhanced" amount of transduction is typically a "statistically significant" amount, and may include an increase that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the number of cells transduced by vehicle, a control composition, or other transduction method.

By "decrease" or "lower," or "lessen," or "reduce," or "abate" refers generally to compositions or methods that result in comparably fewer transduced cells compared to cells transduced with compositions and/or methods according to the present invention. A "decrease" or "reduced" amount of transduced cells is typically a "statistically significant" amount, and may include a decrease that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the number of transduced cells (reference response) produced by compositions and/or methods according to the present invention.

By "maintain," or "preserve," or "maintenance," or "no change," or "no substantial change," or "no substantial decrease" refers generally to a physiological response that is comparable to a response caused by either vehicle, a control molecule/composition, or the response in a particular cell lineage. A comparable response is one that is not significantly different or measurable different from the reference response.

The articles "a," "an," and "the" are used herein to refer to one or to more than one (i.e. to at least one) of the grammatical object of the article. By way of example, "an element" means one element or more than one element.

The use of the alternative (e.g., "or") should be understood to mean either one, both, or any combination thereof of the alternatives. As used herein, the terms "include" and "comprise" are used synonymously.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2%> or 1%) to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length ±15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of is meant including, and limited to, whatever follows the phrase "consisting of." Thus, the phrase "consisting of indicates that the listed elements are required or mandatory, and that no other elements may be present. By "consisting essentially of is meant including any elements listed after the phrase, and limited to other elements that do not interfere with or contribute to the activity or action specified in the disclosure for the listed elements. Thus, the phrase "consisting essentially of indicates that the listed elements are required or mandatory, but that no other elements are optional and may or may not be present depending upon whether or not they affect the activity or action of the listed elements Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

In the following description, certain specific details are set forth in order to provide a thorough understanding of various embodiments of the invention. However, one skilled in the art will understand that the invention may be practiced without these details. In addition, it should be understood that the individual vectors, or groups of vectors, derived from the various combinations of the structures and substituents described herein, are disclosed by the present application to the same extent as if each vector or group of vectors was set forth individually. Thus, selection of particular vector structures or particular substituents is within the scope of the present disclosure.

C. Viral Vectors

Retroviral and lentiviral vectors have been tested and found to be suitable delivery vehicles for the stable introduction of genes of interest, e.g., encoding therapeutic polypeptides, into the genome of a broad range of target cells. The present invention contemplates, in part, improved delivery of gene therapy vectors to a population of cells that are administered to a subject to provide gene therapy.

The present invention further provides transfer vectors, which may be used to practice methods of the present invention. While the skilled artisan will appreciate that such transfer vectors may be produced using a variety of different viral vectors, in particular embodiments, the transfer vector is a retroviral vector or a lentiviral vector, in part since lentiviral vectors are capable of providing efficient delivery, integration and long term expression of transgenes into non-dividing cells both in vitro and in vivo. A variety of lentiviral vectors are known in the art, see Naldini et al, (1996a, 1996b, and 1998); Zufferey et al, (1997); Dull et al, 1998, U.S. Pat. Nos. 6,013,516; and 5,994,136, any of which may be adapted to produce a transfer vector of the present invention.

In general, these vectors are plasmid-based or virus-based, and are configured to carry the essential sequences for transfer of a nucleic acid encoding a therapeutic polypeptide into a host cell.

In illustrative embodiments, the retroviral vector is a lentiviral vector. Thus, the vectors may be derived from human immunodeficiency-1 (HIV-1), human immunodeficiency-2 (HIV-2), simian immunodeficiency virus (SIV), feline immunodeficiency virus (FIV), bovine immunodeficiency virus (BIV), Jembrana Disease Virus (JDV), equine infectious anemia virus (EIAV), caprine arthritis encephalitis virus (CAEV) and the like. HIV based vector backbones (i.e., HIV cis-acting sequence elements and HIV gag, pol and rev genes) are generally be preferred in connection with most aspects of the present invention in that HIV-based constructs are the most efficient at transduction of human cells.

Although particular illustrative embodiments include more detailed description of vectors, compositions and methods used to correct hematopoietic disorders, e.g., hemoglobinopathies, the invention should not be considered to be limited by this disclosure. One having skill in the art would readily appreciate that the principles illustrated herein can be applied to gene therapy in other systems, e.g., nervous system, including the eye, central nervous system, and peripheral nervous system; the circulatory system; the muscular system; the skeletal system; organs, including the skin, heart, lungs, pancreas, liver, kidney, intestine, and the like.

In one embodiment, the present invention provides vectors, e.g., lentiviral vectors, that comprise an expression control sequence that directs expression of polynucleotide-of-interest, e.g., a globin gene, in a particular cell type or cell lineage. The use of a cell type or cell lineage expression control sequence offers safety advantages in restricting polynucleotide expression to a desired stage of cell differentiation in a single lineage; and thus, vectors of the invention alleviate concerns dealing with ectopic expression of polypeptides in undesired cells types.

In one non-limiting example, the expression control sequence may be a ubiquitous expression control sequence as disclosed elsewhere herein.

In another non-limiting example, the expression control sequence may be a stem cell specific expression control sequence that directs stem cell specific expression of the polynucleotide-of-interest in an embryonic stem cell, a neural stem cell, a mesenchymal stem cell, a liver stem cell, a pancreatic stem cell, a cardiac stem cell, a kidney stem cell, or a hematopoietic stem cell.

In yet another non-limiting example, the expression control sequence may a cell type or cell lineage specific expression control sequence that directs expression of the polynucleotide-of-interest in a hematopoietic stem cell, a hematopoietic progenitor cell, a myeloid cell, a lymphoid cell, a thrombopoietic lineage, a mast cell, an erythropoietic lineage cell, a granulopoietic lineage cell, and a monocytopoietic lineage cell.

In particular embodiments, a vector of the invention may be used to express a polynucleotide, e.g., gene-of-interest in one or more or all hematopoietic cells including, but not limited to hematopoietic stem cells, hematopoietic progenitor cells, myeloid progenitors, lymphoid progenitors, thrombopoietic progenitors, erythroid progenitors, granulopoietic progenitors, monocytopoietic progenitors, megakaryoblasts, promegakaryocytes, megakaryocytes, thrombocytes/platelets, proerythroblasts, basophilic erythroblasts, polychromatic erythroblasts, orthochromatic erythroblasts, polychromatic erythrocytes, erythrocytes (RBCs), basophilic promyelocytes, basophilic myelocytes, basophilic metamyelocytes, basophils, neutrophilic promyelocytes, neutrophilic myelocytes, neutrophilic metamyelocytes, neutrophils, eosinophilic promyelocytes, eosinophilic myelocytes, macrophages, dendritic cells, lymphoblasts, prolymphocytes, natural killer (NK)-cells, small lymphocytes, T-lymphocytes, B-lymphocytes, plasma cells, and lymphoid dendritic cells.

In preferred embodiments, a vector of the invention may be used to express a polynucleotide, e.g., gene-of-interest in one or more erythroid cells, e.g., proerythroblast, basophilic erythroblast, polychromatic erythroblast, orthochromatic erythroblast, polychromatic erythrocyte, and erythrocyte (RBC).

In one embodiment, the vector comprises a hematopoietic cell promoter, enhancer, or promoter/enhancer operably linked to a gene of interest, e.g., globin.

Suitable cell type or cell lineage specific expression control sequences include, but are not limited to hematopoietic cell expression control sequences, such as, for example, a hematopoietic stem cell promoter, and a hematopoietic progenitor cell promoter. In embodiments where expression of the gene of interest is desired in one or more erythroid cells, a suitable hematopoietic cell expression control sequence can include, but is not limited to, an erythroid cell specific promoter and optionally an erythroid cell specific enhancer, a human β-globin promoter, a human β-globin LCR, or a human a-globin HS40 enhancer and an ankyrin-1 promoter.

In one embodiment, suitable cell type or cell lineage specific expression control sequences include, but are not limited to a promoter active in a microglial cell. In certain embodiments, the promoter comprises a MND promoter or transcriptionally active fragment thereof, operably linked to a gene of interest, e.g., ABCD1.

The use of a cell type or cell lineage expression control sequence offers safety advantages in restricting polynucleotide expression to this a desired stage of cell differentiation in a single lineage; and thus, vectors of the invention alleviate concerns dealing with ectopic expression of polypeptides in undesired cells types. In one embodiment, the invention provides, a vector comprising one or more LTRs, and an expression control sequence operably linked to a gene of interest. In related embodiment, the expression control sequence is an erythroid cell specific expression control sequence is selected from the group consisting of: a human β-globin promoter; a human β-globin LCR; and a human a-globin HS40 enhancer and an ankyrin-1 promoter.

In various embodiments, the design of the vector will be made with the goal of treating, preventing, or ameliorating a particular hematopoietic disease, disorder, or condition. For example, the present invention contemplates vectors for gene therapy of hemoglobinopathies that comprise a gene of interest selected from the group consisting of: human a-globin, human β-globin, human δ-globin, and human γ-globin, or biologically active variants or fragments thereof. In one embodiment, the globin gene is selected from the group consisting of a wild type human β-globin gene, a deleted human β-globin gene comprising one or more deletions of intron sequences, and a mutated human β-globin gene encoding at least one antisickling amino acid residue.

In a particular embodiment, wherein the condition being treated is a sickle cell hemoglobinopathy, the gene of interest can be an antisickling protein. As used herein, "antisickling protein" refers to a polypeptide that prevents or reverses the pathological events leading to sickling of erythrocytes in sickle cell conditions. In one embodiment of the invention, the transduced cells of the invention are used to deliver antisickling proteins to a subject with a hemoglobinopathic condition. Antisickling proteins also include mutated β-globin genes comprising antisickling amino acid residues.

In a preferred embodiment, one such globin variant is the human βA-globin gene encoding a threonine to glutamine mutation at codon 87 (βA-T87Q) or a human βA-globin gene (the mature form of the globin polypeptide has been processed by cleavage of the N-terminal methionine, codon 87 of the mature globin polypeptide is threonine; codon 88 of the full-length, non-cleaved globin polypeptide is threonine). Other antisickling amino acid residues are known in the art and may be useful in the present invention. For example, see U.S. Pat. Nos. 6,051,402; 5,861,488; 6,670,323; 5,864,029; 5,877,288; and Levasseur et al., Blood 102:4312-4319 (2003), which are herein incorporated by reference.

In certain embodiments, a vector that comprising an erythroid specific expression control sequence is used to treat, prevent, or ameliorate of a vast number of disorders extending well beyond the hemoglobinopathies. Red blood cell precursors are a useful cell population in which to express polypeptides that can be secreted into the circulation and thus delivered systemically. An example of such in vivo protein delivery is human Factor IX, a clotting factor that is missing in patients with Hemophilia B, see, e.g., A. H. Chang, et al., Molecular Therapy (2008), which is herein incorporated by reference.

In one embodiment, cells transduced with vectors of the invention can be used as "factories" for protein secretion, in vitro, ex vivo, or in vivo. For example, a vector comprising an erythroid cell specific expression control sequence can be used for large-scale in vitro production of proteins from erythroid cells differentiated from HSCs or from embryonic stem cells.

Polynucleotides-of-interest that could be expressed in this way include, but are not limited to: adenosine deaminase, the enzymes affected in lysosomal storage diseases, apolipoprotein E, brain derived neurotropihic factor (BDNF), bone morphogenetic protein 2 (BMP-2), bone morphogenetic protein 6 (BMP-6), bone morphogenetic protein 7 (BMP-7), cardiotrophin 1 (CT-1), CD22, CD40, ciliary neurotrophic factor (CNTF), CCL1-CCL28, CXCL1-CXCL17, CXCL1, CXCL2, CX3CL1, vascular endothelial cell growth factor (VEGF), dopamine, erythropoietin, Factor IX, Factor VIII, epidermal growth factor (EGF), estrogen, FAS-ligand, fibroblast growth factor 1 (FGF-1), fibroblast growth factor 2 (FGF-2), fibroblast growth factor 4 (FGF-4), fibroblast growth factor 5 (FGF-5), fibroblast growth factor 6 (FGF-6), fibroblast growth factor 1 (FGF-7), fibroblast growth factor 1 (FGF-10), Flt-3, granulocyte colony-stimulating factor (G-CSF), granulocyte macrophage stimulating factor (GM-CSF), growth hormone, hepatocyte growth factor (HGF), interferon alpha (IFN-α), interferon beta (IFN-b), interferon gamma (IFNg), insulin, glucagon, insulin-like growth factor 1(IGF-1), insulin-like growth factor 2 (IGF-2), interleukin 1 (IL-1), interleukin 2 (IL-2), interleukin 3 (IL-3), interleukin 4 (IL-4), interleukin 5 (IL-5), interleukin 6 (IL-6), interleukin 7 (IL-7), interleukin 8 (IL-8), interleukin 9 (IL-9), interleukin 10 (IL-10), interleukin 11 (IL-11), interleukin 12 (IL-12), interleukin 13 (IL-13), interleukin 15 (IL-15), interleukin 17 (IL-17), interleukin 19 (IL-19), macrophage colony-stimulating factor (M-CSF), monocyte chemotactic protein 1 (MCP-1), macrophage inflammatory protein 3a (MIP-3a), macrophage inflammatory protein 3b (MIP-3b), nerve growth factor (NGF), neurotrophin 3 (NT-3), neurotrophin 4 (NT-4), parathyroid hormone, platelet derived growth factor AA (PDGF-AA), platelet derived growth factor AB (PDGF-AB), platelet derived growth factor BB (PDGF-BB), platelet derived growth factor CC (PDGF-CC), platelet derived growth factor DD (PDGF-DD), RANTES, stem cell factor (SCF), stromal cell derived factor 1 (SDF-1), testosterone, transforming growth factor alpha (TGF-a), transforming growth factor beta (TGF-b), tumor necrosis factor alpha (TNF-α), Wnt1, Wnt2, Wnt2b/13, Wnt3, Wnt3a, Wnt4, Wnt5a, Wnt5b, Wnt6, Wnt7a, Wnt7b, Wnt7c, Wnt8, Wnt8a, Wnt8b, Wnt8c, Wnt10a, Wnt10b, Wnt11, Wnt14, Wnt15, or Wnt16, Sonic hedgehog, Desert hedgehog, and Indian hedgehog.

In one embodiment, a vector of the invention comprises at least one modified or unmodified retroviral LTR, e.g., lentiviral LTR, a β-globin promoter and a β-globin locus control region (LCR) operably linked to a polynucleotide of interest, e.g., encoding a globin polypeptide. Suitable modifications of the LTRs include, but are not limited to: replacement of the 5' LTR is with a heterologous promoter, e.g., cytomegalovirus (CMV) promoter, a Rous Sarcoma Virus (RSV) promoter, a thymidine kinase promoter, or an Simian Virus 40 (SV40) promoter; and one or more modifications, additions, and/or deletions of a 3' LTR as discussed elsewhere herein.

In a particular embodiment, erythroid specific expression of a polynucleotide is achieved using a human β-globin promoter, a β-globin LCR that comprises one or more of DNAase I hypersensitive sites 2, 3 and 4 from the human β-globin LCR, and/or a human β-globin 3' enhancer element.

In various embodiments, a vector of the invention comprises one or more elements selected from the group consisting of: a Psi packaging sequence (Ψ+), a central polypurine tract/DNA flap (cPPT/FLAP), a retroviral export element, a posttranscriptional regulatory element, one or more insulator elements, a polyadenylation sequence, a selectable marker, and a cell suicide gene, as discussed elsewhere herein.

In various embodiments, the vectors of the invention comprise a promoter operably in hematopoietic cell operably linked to a gene encoding a polypeptide that provides therapy for hemoglobinopathies. The vectors may have one or more LTRs, wherein either LTR comprises one or more modifications, such as one or more nucleotide substitutions, additions, or deletions. The vectors may further comprise one of more accessory elements to increase transduction efficiency/e.g., a cPPT/FLAP), viral packaging (e.g., a Psi (Ψ) packaging signal, RRE), and/or other elements that increase therapeutic gene expression/e.g., poly (A) sequences).

In one embodiment, a vector comprises a left (5') retroviral LTR, a Psi packaging sequence (Ψ+) central polypurine tract/DNA flap (cPPT/FLAP), a retroviral export element, a β-globin promoter, a β-globin locus control region (LCR), and optionally a 3' β-globin enhancer operably linked to a polynucleotide of interest, and a right (3') retroviral LTR that comprises one or more insulator elements, or a polyadenylation sequence.

In particular embodiment, a vector of the invention is a lentiviral vector that comprises a left (5') HIV-1 LTR, a Psi packaging sequence (Ψ+) an HIV-1 central polypurine tract/DNA flap (cPPT/FLAP), a rev response element (RRE), a β-globin promoter, a β-globin locus control region (LCR), and optionally a 3' β-globin enhancer operably linked to a polynucleotide of interest, and a right (3') retroviral LTR that comprises one or more insulator elements, and a rabbit β-globin polyA sequence (ˆgpA).

In various embodiments, the vectors of the invention comprise a promoter operably in a microglial cell operably linked to a gene encoding a polypeptide that provides therapy for adrenoleukodystrophies and/or adrenomyeloneuropathies. The vectors may have one or more LTRs, wherein either LTR comprises one or more modifications, such as one or more nucleotide substitutions, additions, or deletions. The vectors may further comprise one of more accessory elements to increase transduction efficiency (e.g., a cPPT/FLAP), viral packaging (e.g., a Psi (ΨP) packaging signal, RRE), and/or other elements that increase therapeutic gene expression (e.g., poly (A) sequences).

In a particular embodiment, the transfer vector of the invention comprises a left (5') retroviral LTR; a central polypurine tract/DNA flap (cPPT/FLAP); a retroviral export element; a promoter active in a microglial cell, operably linked to a polynucleotide encoding an ATP-binding cassette, sub-family D, member 1 (ABCD1) polypeptide; and a right (3') retroviral LTR.

In a certain embodiment, the invention provides a lentiviral vector comprising: a left (5') HIV-1 LTR; a Psi (Ψ) packaging signal; a cPPT/FLAP; an RRE; a MND promoter, operably linked to a polynucleotide encoding a human ABCD1 polypeptide; a right (3') self-inactivating (SIN) HIV-1 LTR; and a rabbit β-globin polyadenylation sequence.

The skilled artisan would appreciate that many other different embodiments can be fashioned from the existing embodiments of the invention, such that the therapeutic transgene or gene of interest is expressed in a target cell type or cell lineage other than the hematopoietic lineage, e.g., the neuronal lineage.

D. Methods of Transduction

The present invention contemplates, in part, methods and compositions that significantly increase the transduction efficiency of target cells. Without wishing to be bound to any particular theory, it is contemplated that the compositions and methods of the present invention may be used to transduce significantly more cells with significantly less virus, thereby minimizing the risk of genomic alteration and/or insertional activation of proto-oncogenes in the genome of the therapeutic cell. Minimizing the risk of insertional activation of proto-oncogenes and other genomic alterations in the therapeutic cell is an important consideration in devising a suitable gene therapy protocol because it minimizes the chance that transduced cells comprising cancer like characteristics will be clonally expanded in vivo and give rise to cancers, tumors or other diseases involving abnormal cell proliferation. Moreover, the art has noted that transduction with large amounts of virus may be generally cytotoxic to the transduced cell. Thus, the compositions and methods of the present invention further enhance the survivability of transduced cells. Accordingly, the present invention provides a safer and more efficient gene therapy.

The delivery of a gene(s) or other polynucleotide sequences using a retroviral or lentiviral vector by means of viral infection rather than by transfection is referred to as "transduction." In one embodiment, retroviral vectors are transduced into a cell through infection and provirus integration. In certain embodiments, a cell, e.g., a target cell, is "transduced" if it comprises a gene or other polynucleotide sequence delivered to the cell by infection using a viral or retroviral vector. In particular embodiments, a transduced cell comprises one or more genes or other polynucleotide sequences delivered by a retroviral or lentiviral vector in its cellular genome.

In particular embodiments, host cells or target cells transduced with a viral vector of the invention express a therapeutic polypeptide and are administered to a subject to treat and/or prevent a disease, disorder, or condition.

The production of infectious viral particles and viral stock solutions may be carried out using conventional techniques. Methods of preparing viral stock solutions are known in the art and are illustrated by, e.g., Y. Soneoka et al. (1995) *Nucl. Acids Res.* 23:628-633, and N. R. Landau et al. (1992) *J. Virol.* 66:51 10-51 13.

In particular embodiments, HIV type 1 (HIV-1) based viral particles may be generated by co-expressing the virion packaging elements and the transfer vector in a producer cell. These cells may be transiently transfected with a number of plasmids. Typically from three to four plasmids are employed, but the number may be greater depending upon the degree to which the lentiviral components are broken up into separate units. For example, one plasmid may encode the core and enzymatic components of the virion, derived from HIV-1. This plasmid is termed the packaging plasmid. Another plasmid typically encodes the envelope protein(s), most commonly the G protein of vesicular stomatitis virus (VSV G) because of its high stability and broad tropism. This plasmid may be termed the envelope expression plasmid. Yet another plasmid encodes the genome to be transferred to the target cell, that is, the vector itself, and is called the transfer vector. The packaging plasmids can be introduced into human cell lines by known techniques, including calcium phosphate transfection, lipofection or electroporation. Recombinant viruses with titers of several millions of transducing units per milliliter (TU/ml) can be generated by this technique and variants thereof. After ultracentrifugation concentrated stocks of about $10^8$ TU/ml, $10^9$ TU/ml, $10^{10}$ TU/ml, $10^{11}$ TU/ml, $10^{12}$ TU/ml, or about $10^{13}$ TU/ml can be obtained.

Infectious virus particles may be collected from the packaging cells using conventional techniques. For example, the infectious particles can be collected by cell lysis, or collection of the supernatant of the cell culture, as is known in the art. Optionally, the collected virus particles may be purified if desired. Suitable purification techniques are well known to those skilled in the art.

Viruses may be used to infect cells in vivo, ex vivo, or in vitro using techniques well known in the art. For example, when cells, for instance $CD34^+$ cells, dendritic cells, peripheral blood cells or stem cells are transduced ex vivo, the vector particles may be incubated with the cells using a dose generally in the order of between 1 to 50 multiplicities of infection (MOI) which also corresponds to $1\times10^5$ to $50\times10^5$ transducing units of the viral vector per $10^5$ cells. This, of course, includes amount of vector corresponding to 1, 2, 3, 4, 5, 6, 7, 8, 9, 10, 15, 20, 25, 30, 35, 40, 45, and 50 MOI.

Viruses may also be delivered to a subject in vivo, by direct injection to the cell, tissue, or organ in need of therapy. Direct injection requires on the order of between 1 to 50 multiplicities of infection (MOI) which also corresponds to $1\times10^5$ to $50\times10^5$ transducing units of the viral vector per $10^5$ cells.

Viruses may also be delivered according to viral titer (TU/mL), which can be measured, for example, by using a commercially available p24 titer assay, which is an ELISA against the p24 viral coat protein. The following formula can be used to calculate the pg/mL of p24: there are approximately 2000 molecules of p24 per physical particle (PP) of lentivirus: $(2\times103)\times(24\times103$ Da of p24 per PP), $48\times106$/ Avogadro=$(48\times106)/(6\times1023)=8\times10^{-17}$ g of p24 per PP, approximately 1 PP per $1\times10^{-16}$ g of p24, $1\times104$ PP per pg of p24. A reasonably well packaged, VSV-G pseudotyped lentiviral vector will have an infectivity index in the range of 1 TU per 1000 physical particles (PP) to 1 TU per 100 PP (or less). Thus, the range is approximately 10 to 100 TU/pg of p24. It is through this conversion that TU/mL is obtained.

Based on previous experience, the amount of lentivirus directly injected is determined by total TU and can vary based on both the volume that could be feasibly injected to the site and the type of tissue to be injected. For example, a brain injection site may only allow for a very small volume of virus to be injected, so a high titer prep would be preferred, a TU of about $1\times10^6$ to $1\times10^7$, about $1\times10^6$ to $1\times10^8$, $1\times10^6$ to $1\times10^9$, about $1\times10^7$ to $1\times10^{10}$, $1\times10^8$ to $1\times10^{11}$, about $1\times10^8$ to $1\times10^{12}$, or about $1\times10^{10}$ to $1\times10^{12}$ or more per injection could be used. However, a systemic delivery could accommodate a much larger TU, a load of $1\times10^8$, $1\times10^9$, $1\times10^{10}$, $1\times10^{11}$, $1\times10^{12}$, $1\times10^{13}$, $1\times10^{14}$, or $1\times10^{15}$, could be delivered.

The present invention contemplates compositions and methods that provide high efficiency transduction of cells in vitro, ex vivo, and in vivo, using lower viral titers than those disclosed above to achieve comparable transduction efficiencies in the absence of the compositions and methods provided herein.

Certain aspects of the present invention arise from the unexpected finding that transduction efficiency is significantly increased by contacting cells, in vitro, ex vivo, or in vivo, with a retrovirus and one or more compounds that stimulate the prostaglandin EP receptor signaling pathway, such as, for example, a small molecule, or those compounds disclosed in WO 2007/1 12084 and WO2010/108028, each of which is herein incorporated by reference in its entirety. As used herein, the terms "stimulate the prostaglandin EP receptor signaling," "activate the prostaglandin EP receptor signaling," or "increase the prostaglandin EP receptor signaling" generally refers to the ability of a compound to increase the cell signaling activity downstream of a prostaglandin EP receptor in the cell contacted with the one or more compounds compared to the cell signaling activity downstream of the prostaglandin EP receptor in the absence of the one or more compounds. Assays that can be used to measure activation or stimulation of the prostaglandin EP receptor signaling pathway are known in the art, and are described in, for example, WO2010/108028, which is herein incorporated by reference in its entirety.

Illustrative examples of compounds that stimulate the prostaglandin EP receptor signaling pathway include, but are not limited to, small molecules, e.g., small organic molecules, prostaglandins, Wnt pathway agonists, cAMP/PBK/AKT pathway agonists, $Ca^{2+}$ second messenger pathway agonists, nitric oxide (NO)/angiotensin signaling agonists, and other compounds known to stimulate the prostaglandin signaling pathway selected from the group consisting of: Mebeverine, Flurandrenolide, Atenolol, Pindolol, Gaboxadol, Kynurenic Acid, Hydralazine, Thiabendazole, Bicuclline, Vesamicol, Peruvoside, Imipramine, Chlorpropamide, 1,5-Pentamethylenetetrazole, 4-Aminopyridine, Diazoxide, Benfotiamine, 12-Methoxydodecenoic acid, N-Formyl-Met-Leu-Phe, Gallamine, IAA 94, Chlorotrianisene, and derivatives of these compounds.

In a preferred embodiment, the compound that stimulates the prostaglandin pathway is a naturally-occurring or synthetic chemical molecule or polypeptide that binds to and/or interacts with an EP receptor, typically to activate or increase one or more of the downstream signaling pathways associated with a prostaglandin EP receptor, as described herein and known in the art.

In one embodiment, the compound that stimulates the prostaglandin pathway is selected from the groups consisting of: $PGA_2$; $PGB_2$; $PGD_2$; PGEi (Alprostadil (Caverject™; Edex™; Muse™; Prostin VR™); $PGE_2$; $PGF_2$; $PGI_2$ (Epoprostenol (Flolan™; Prostacyclin™)); $PGH_2$; $PGJ_2$; and precursors, metabolites, derivatives and analogues thereof.

Additional illustrative compounds that stimulate the prostaglandin pathway include, but are not limited to 15d-$PGJ_2$; delta12-$PGJ_2$; 2-hydroxyheptadecatrienoic acid (HHT); Thromboxane (TXA2 and TXB2); $PGI_2$ analogs, e.g., Iloprost (Ventavis™) and Treprostinil (Remodulin™); $PGF_2$ analogs, e.g., Travoprost (Travatan™), Carboprost tromethamine (Hemabate™), Tafluprost (Zioptanl™), Latanoprost (Xalatan™), Bimatoprost (Lumigan™; Latisse™) Unoprostone isopropyl (Rescula™), Cloprostenol (Ciosin™, Cyclix™, Estrumate™, Lutaprost™, Onsett™, Planate™), Oestrophan, and Superphan; PGEi analogs, e.g., Misoprostol (Cytotec™) and Butaprost; and Corey alcohol-A [[3aa,4a, 5P,6aa]-(-)-[Hexahydro-4-(hydroxymethyl)-2-oxo-2H-cyclopenta/b/furan-5-yl][1,r-bifenyl]-4-carboxylate]; Corey alcohol-B [2H-Cyclopenta[b]furan-2-on,5-(benzoyloxy) hexahydro-4-(hydroxymethyl)[3aR-(3aa,4a,5P,6aa)]]; and Corey diol ((3aR,4S,5R,6aS)-hexahydro-5-hydroxy-4-(hydroxymethyl)-2H-cyclopenta[b]furan-2-one).

In one embodiment, the compound is a prostaglandin EP receptor ligand including, but not limited to, prostaglandin E2(PGE$_2$), as well as "analogs" or "derivatives" thereof. Prostaglandins relate generally to hormone like molecules that are derived from fatty acids containing 20 carbon atoms, including a 5-carbon ring, as described herein and known in the art.

Illustrative examples of PGE$_2$ "analogs" or "derivatives" include, but are not limited to, 16, 16-dimethyl PGE$_2$, 16-16 dimethyl PGE$_2$ p-(p-acetamidobenzamido) phenyl ester, 11-deoxy-16, 16-dimethyl PGE$_2$, 9-deoxy-9-methylene-16, 16-dimethyl PGE$_2$, 9-deoxy-9-methylene PGE$_2$, 9-keto Fluprostenol, 5-trans PGE$_2$, 17-phenyl-omega-trinor PGE$_2$, PGE$_2$ serinol amide, PGE$_2$ methyl ester, 16-phenyl tetranor PGE$_2$, 15(S)-15-methyl PGE$_2$, 15 (R)-15-methyl PGE$_2$, 8-iso-15-keto PGE$_2$, 8-iso PGE$_2$ isopropyl ester, 20-hydroxy PGE$_2$, 11-deoxy PGEi, nocloprost, sulprostone, butaprost, 15-keto PGE$_2$, and 19 (R) hydroxy PGE$_2$.

Also included are prostaglandin analogs or derivatives having a similar structure to PGE$_2$ that are substituted with halogen at the 9-position (see, e.g., WO 2001/12596, herein incorporated by reference in its entirety), as well as 2-decarboxy-2-phosphinico prostaglandin derivatives, such as those described in U.S. Publication No. 2006/0247214, herein incorporated by reference in its entirety).

In some embodiments, the compound is a non-PGE$_2$-based ligand. In certain embodiments, the non-PGE$_2$-based ligand is selected from the group consisting of an EP1 agonist, an EP2 agonist, an EP3 agonist, and an EP4 agonist.

In particular embodiments, the prostaglandin EP receptor is selected from EP1, EP2, EP3, and EP4.

Illustrative examples of non-PGE$_2$-based EP1 agonists include, but are not limited to, ONO-DI-004 and ONO-8713. Illustrative examples of non-PGE2-based EP2 agonist include, but are not limited to, CAY10399, ONO_8815 Ly, ONO-AE1-259, and CP-533,536. Additional examples of non-PGE$_2$-based EP2 agonists include the carbazoles and fluorenes disclosed in WO 2007/071456, herein incorporated by reference for its disclosure of such agents. Illustrative examples of non-PGE$_2$-based EP3 agonist include, but are not limited to, AE5-599, MB28767, GR 63799X, ONO-NT012, and ONO-AE-248. Illustrative examples of non-PGE$_2$-based EP4 agonist include, but are not limited to, ONO-4819, APS-999 Na, AH23848, and ONO-AE 1-329. Additional examples of non-PGE$_2$-based EP4 agonists can be found in WO/2000/038663; U.S. Pat. Nos. 6,747,037; and 6,610,719, each of which are incorporated by reference for their disclosure of such agonists.

In one embodiment, the compound that stimulates the prostaglandin EP receptor signaling pathway is a Wnt agonist. Illustrative examples of Wnt agonists include, but are not limited to Wnt polypeptides and glycogen synthase kinase 3 (GSK3) inhibitors. Illustrative examples of wnt polypeptides suitable for use as compounds that stimulate the prostaglandin EP receptor signaling pathway include, but are not limited to, Wnt1, Wnt2, Wnt2b/13, Wnt3, Wnt3a, Wnt4, Wnt5a, Wnt5b, Wnt6, Wnt7a, Wnt7b, Wnt7c, Wnt8, Wnt8a, Wnt8b, Wnt8c, Wnt10a, Wnt10b, Wnt11, Wnt14, or Wnt15 and biologically active fragments thereof.

GSK3 inhibitors suitable for use as compounds that stimulate the prostaglandin EP receptor signaling pathway bind to and decrease the activity of GSK3a, or GSK3p.

Illustrative examples of GSK3 inhibitors include, but are not limited to, BIO (6-bromoindirubin-3'-oxime), LiCl or other GSK-3 inhibitors, as exemplified in U.S. Pat. Nos. 6,057,117 and 6,608,063; and U.S. applications 2004/0092535 and 2004/0209878; ATP-competitive, selective GSK-3 inhibitors CHIR-91 1 and CHIR-837 (also referred to as CT-99021 and CT-98023 respectively). Chiron Corporation (Emeryville, Calif.).

In another embodiment, the compound that stimulates the prostaglandin EP receptor signaling pathway increases signaling through the cAMP/P13K/AKT second messenger pathway and is selected from the group consisting of dibutyryl cAMP (DBcAMP), phorbol ester, forskolin, sclareline, 8-bromo-cAMP, cholera toxin (CTx), aminophylline, 2,4 dinitrophenol (DNP), norepinephrine, epinephrine, isoproterenol, isobutylmethylxanthine (IBMX), caffeine, theophylline (dimethylxanthine), dopamine, rolipram, iloprost, pituitary adenylate cyclase activating polypeptide (PACAP), and vasoactive intestinal polypeptide (VIP, and derivatives of these agents.

In yet another embodiment, the compound that stimulates the prostaglandin EP receptor signaling pathway increases signaling through the Ca2+ second messenger pathway and is selected from the group consisting of Bapta-AM, Fendiline, Nicardipine and derivatives of these compounds.

In another embodiment, the compound that stimulates the prostaglandin EP receptor signaling pathway increases signaling through the NO/Angiotensin signaling pathway and is selected from the group consisting of L-Arg, Sodium Nitroprusside, Sodium Vanadate, Bradykinin, and derivatives thereof.

In one embodiment, the present invention provides a method of improving the efficiency of transduction comprising culturing a population of cells with a retrovirus and one or more compounds that increases the prostaglandin EP receptor signaling selected from the group consisting of: a prostaglandin, PGE2; PGD2; PGI2; Linoleic Acid; 13(s)-HODE; LY171883; Mead Acid; Eicosatrienoic Acid; Epoxyeicosatrienoic Acid; ONO-259; Cay 1039; a PGE2 receptor agonist; 16,16-dimethyl PGE2; 19(R)-hydroxy PGE2; 16,16-dimethyl PGE2 p-(p-acetamidobenzamido) phenyl ester; 11-deoxy-16,16-dimethyl PGE2; 9-deoxy-9-methylene-16,16-dimethyl PGE2; 9-deoxy-9-methylene PGE2; Butaprost; Sulprostone; PGE2 serinol amide; PGE2 methyl ester; 16-phenyl tetranor PGE2; 15(S)-15-methyl PGE2; 15(R)-15-methyl PGE2; BIO; 8-bromo-cAMP; Forskolin; Bapta-AM; Fendiline; Nicardipine; Nifedipine; Pimozide; Strophanthidin; Lanatoside; L-Arg; Sodium Nitroprusside; Sodium Vanadate; Bradykinin; Mebeverine; Flurandrenolide; Atenolol; Pindolol; Gaboxadol; Kynurenic Acid; Hydralazine; Thiabendazole; Bicuclline; Vesamicol; Peruvoside; Imipramine; Chlorpropamide; 1,5-Pentamethylenetetrazole; 4-Aminopyridine; Diazoxide; Benfotiamine; 12-Methoxydodecenoic acid; N-Formyl-Met-Leu-Phe; Gallamine; IAA 94; and Chlorotrianisene.

In a particular embodiment, the present invention provides a method of improving the efficiency of transduction comprising culturing a population of cells with a retrovirus and one or more compounds that are ligands of a prostaglandin EP receptor selected from the group consisting of: 16,16-dimethyl PGE2, 16-16 dimethyl PGE2 p-(p-acetamidobenzamido) phenyl ester, 11-deoxy-16,16-dimethyl PGE2, 9-deoxy-9-methylene-16, 16-dimethyl PGE2, 9-deoxy-9-methylene PGE2, 9-keto Fluprostenol, 5-trans PGE2, 17-phenyl-omega-trinor PGE2, PGE2 serinol amide, PGE2 methyl ester, 16-phenyl tetranor PGE2, 15(S)-15-methyl PGE2, 15 (R)-15-methyl PGE2, 8-iso-15-keto PGE2, 8-iso PGE2 isopropyl ester, 20-hydroxy PGE2, 11-deoxy PGEi, nocloprost, sulprostone, butaprost, 15-keto PGE2, and 19(R) hydroxy PGE2.

The present invention also contemplates that the transduction efficiency of cells can be increased by culturing cells in the presence of a retrovirus, a compound that stimulates a prostaglandin EP receptor pathway, e.g., PGE2, and one or more histone deacetylase (HDAC) inhibitors.

Illustrative examples of HDAC inhibitors suitable for use in the compositions and methods of the present invention include, but are not limited to: HDAC inhibitors include, but are not limited to, TSA (trichostatin A) (see, e.g., Adcock, (2007) *British Journal of Pharmacology* 150:829-831), VPA (valproic acid) (see, e.g., Munster, et al, (2007) *Journal of Clinical Oncology* 25: 18S: 1065), sodium butyrate (NaBu) (see, e.g., Han, et al., (2007) *Immunology Letters* 108: 143-150), SAHA (suberoylanilide hydroxamic acid or vorinostat) (see, e.g., Kelly, et al, (2005) *Nature Clinical Practice Oncology* 2: 150-157), sodium phenylbutyrate (see, e.g., Gore, et al, (2006) *Cancer Research* 66:6361-6369), depsipeptide (FR901228, FK228) (see, e.g., Zhu, et al, (2003) *Current Medicinal Chemistry* 3(3): 187-199), trapoxin (TPX) (see, e.g., Furumai, et al, (2001) *PNAS* 98(1): 87-92), cyclic hydroxamic acid-containing peptide 1 (CHAP1) (see, Furumai supra), MS-275 (see, e.g., Carninci, et al., WO2008/126932, incorporated herein by reference)), LBH589 (see, e.g., Goh, et al., WO2008/108741 incorporated herein by reference) and PXD-101 (see, Goh, supra).

The present invention contemplates that cells may be cultured in the presence of a retrovirus may be exposed to (contacted with) a compound that stimulates the prostaglandin EP receptor signaling pathway and/or an HDAC inhibitor for a duration of about 10 minutes to about 72 hours, about 30 minutes to about 72 hours, about 30 minutes to about 48 hours, about 30 minutes to about 24 hours, about 30 minutes to about 12 hours, about 30 minutes to about 8 hours, about 30 minutes to about 6 hours, about 30 minutes to about 4 hours, about 30 minutes to about 2 hours, about 1 hour to about 2 hours, or any intervening period of time.

In one embodiment, the cells cultured with a retrovirus are exposed to (contacted with) a compound that stimulates the prostaglandin EP receptor signaling pathway and/or an HDAC inhibitor for about 30 minutes, about 1 hour, about 2 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 48 hours, or about 72 hours, or any intervening duration of time.

The present invention contemplates that the cells may be cultured with one or more compounds that stimulate the prostaglandin EP receptor signaling pathway and/or one or more HDAC inhibitors prior to culture with a retrovirus, during culture with a retrovirus, or after culture with a retrovirus, or any combination thereof for any of the foregoing periods of time disclosed herein.

The present invention further contemplates that cells may be cultured with one or more compounds that stimulate the prostaglandin EP receptor signaling pathway and a retrovirus prior to culture with one or more HDAC inhibitors, during culture with one or more HDAC inhibitors, or after culture with one or more HDAC inhibitors, or any combination thereof for any of the foregoing periods of time disclosed herein.

The present invention also contemplates that cells may be cultured with a retrovirus prior to culture with one or more compounds that stimulate the prostaglandin EP receptor signaling pathway and/or one or more HDAC inhibitors, during culture with one or more compounds that stimulate the prostaglandin EP receptor signaling pathway and/or one or more HDAC inhibitors, or after culture one or more compounds that stimulate the prostaglandin EP receptor signaling pathway and/or one or more HDAC inhibitors, or any combination thereof for any of the foregoing periods of time disclosed herein.

Furthermore, one having ordinary skill in the art would appreciate that the present inventive methods for increasing transducing include culturing cells with retrovirus, one or more compounds that stimulate the prostaglandin EP receptor signaling pathway and/or one or more HDAC inhibitors, during the first 6 hours of transduction, the first 12 hours of transduction, the first 24 hours of transduction, the first 48 hours of transduction, or the first 72 hours of the transduction, or any intervening duration of transduction.

In addition, the present invention contemplates that cells may be transduced 1, 2, 3 or more times in the presence of a retrovirus and one or more compounds that stimulate the prostaglandin EP receptor signaling pathway and/or one or more HDAC inhibitors. In another embodiment, the present invention contemplates that cells may be transduced 1, 2, 3 or more times in the presence of a retrovirus and exposed to (contacted with) one or more compounds that stimulate the prostaglandin EP receptor signaling pathway and/or one or more HDAC inhibitors only once or twice In a particular embodiment, the invention contemplates that cells can be cultured in the retrovirus, one or more compounds that stimulate the prostaglandin EP receptor signaling pathway and/or one or more HDAC inhibitors, wherein the cells are exposed to or contacted with the foregoing for the same or different lengths of time, as disclosed elsewhere herein.

The present invention also contemplates that the compositions and methods of the invention can increase the transduction of virtually any cell type to at least about 30%, at least about 40%, at least about 50%>, at least about 60%>, at least about 65%, at least about 70%>, at least about 75%, at least about 80%>, at least about 85%, at least about 90%>, at least about 91%>, at least about 92%, at least about 93%>, at least about 94%>, at least about 95%, at least about 96%>, at least about 97%, at least about 98%, at least about 99%, or at least about 100%.

In particular embodiments, increase in transduction efficiency represents at least 2-fold, at least 5-fold, at least 10-fold, at least 25-fold, at least 50-fold, or at least 100-fold, or more fold enrichment of transduced cells compared to cells transduced with vector alone.

Prior to, during, and/or following transduction, the cells may be cultured in media suitable for the maintenance, growth, or proliferation of the cells. Suitable culture media and conditions are well known in the art. Such media include, but are not limited to, Dulbecco's Modified Eagle's Medium® (DMEM), DMEM F12 Medium®, Eagle's Minimum Essential Medium®, F-12K Medium®, Iscove's Modified Dulbecco's Medium®, RPMI-1640 Medium®, and serum-free medium for culture and expansion of hematopoietic cells SFEM®. Many media are also available as low-glucose formulations, with or without sodium pyruvate.

Additional supplements also can be used advantageously to supply the cells with the necessary trace elements for optimal growth and expansion. Such supplements include insulin, transferrin, sodium selenium and combinations thereof. These components can be included in a salt solution such as, but not limited to, Hanks' Balanced Salt Solution®

(HBSS), Earle's Salt Solution®, antioxidant supplements, MCDB-201® supplements, phosphate buffered saline (PBS), ascorbic acid and ascorbic acid-2-phosphate, as well as additional amino acids. Many cell culture media already contain amino acids, however, some require supplementation prior to culturing cells. Such amino acids include, but are not limited to, L-alanine, L-arginine, L-aspartic acid, L-asparagine, L-cysteine, L-cystine, L-glutamic acid, L-glutamine, L-glycine, L-histidine, L-isoleucine, L-leucine, L-lysine, L-methionine, L-phenylalanine, L-proline, L-serine, L-threonine, L-tryptophan, L-tyrosine, and L-valine. It is well within the skill of one in the art to determine the proper concentrations of these supplements.

Hormones also can be advantageously used in the cell cultures of the present invention and include, but are not limited to, D-aldosterone, diethylstilbestrol (DES), dexamethasone, β-estradiol, hydrocortisone, insulin, prolactin, progesterone, somatostatin/human growth hormone (HGH), thyrotropin, thyroxine and L-thyronine.

Lipids and lipid carriers also can be used to supplement cell culture media, depending on the type of cell and the fate of the differentiated cell. Such lipids and carriers can include, but are not limited to, cyclodextrin (α, β, γ), cholesterol, linoleic acid conjugated to albumin, linoleic acid and oleic acid conjugated to albumin, unconjugated linoleic acid, linoleic-oleic-arachidonic acid conjugated to albumin and oleic acid unconjugated and conjugated to albumin, among others.

Cells may also be cultured in low-serum or serum-free culture medium. Serum-free medium used to culture cells is described in, for example, U.S. Pat. No. 7,015,037. Many cells have been grown in serum-free or low-serum medium.

Following transduction, the transduced cells may be cultured under conditions suitable for their maintenance, growth or proliferation. In particular embodiments, the transduced cells are cultured for about 1, 2, 3, 4, 5, 6, 7, 8, 9, 10, 11, 12, 13 or 14 days before transplantation.

Prior to, during and/or following transduction, the cells may be cultured under conditions that promote the expansion of stem cells or progenitor cells. Any method known in the art may be used. In certain embodiments, prior to, during or following transduction, the cells are cultured in the presence of one or more growth factors that promote the expansion of stem cells or progenitor cells. Examples of growth factors that promote the expansion of stem cells or progenitor cells include, but are not limited to, fetal liver tyrosine kinase (Flt3) ligand, stem cell factor, and interleukins 6 and 11, which have been demonstrated to promote self-renewal of murine hematopoietic stem cells. Others include Sonic hedgehog, which induces the proliferation of primitive hematopoietic progenitors by activation of bone morphogenetic protein 4, Wnt3a, which stimulates self-renewal of HSCs, brain derived neurotrophic factor (BDNF), epidermal growth factor (EGF), fibroblast growth factor (FGF), ciliary neurotrophic factor (CNF), transforming growth factor-3 (TGF-β), a fibroblast growth factor (FGF, e.g., basic FGF, acidic FGF, FGF-17, FGF-4, FGF-5, FGF-6, FGF-8b, FGF-8c, FGF-9), granulocyte colony stimulating factor (GCSF), a platelet derived growth factor (PDGF, e.g., PDGFAA, PDGFAB, PDGFBB), granulocyte macrophage colony stimulating factor (GMCSF), stem cell factor (SCF), stromal cell derived factor (SCDF), insulin like growth factor (IGF), thrombopoietin (TPO) or interleukin-3 (IL-3). In particular embodiments, before, during or following transduction, the cells are cultured in the presence of one or more growth factors that promote expansion of stem cells or progenitor cells.

While the description and examples provided herein focus on the transduction and selection of multipotent cells, including hematopoietic stem cells in particular, the methods and compositions of the present invention may also be used to transduce and select other cell types, including other types of pluripotent or multipotent stem cells and fragile cells previously not amenable to selection of transduced cells for therapeutic uses.

Cell used according to the methods of the present invention may be obtained from any animal, preferably a mammal, e.g., a non-human primate or human, and more preferably a human, and they may be transplanted into any animal, preferably a mammal, and more preferably a human Cells suitable for transduction and administration in the gene therapy methods of the invention include, but are not limited to stem cells, progenitor cells, and differentiated cells.

Illustrative examples of stem cells suitable for transduction with the compositions and methods of the present invention include, but are not limited to embryonic stem cells, induced pluripotent stem cells, mesodermal stem cells, endodermal stem cells, and ectodermal stem cells.

In particular embodiments, the population or source of cells transduced using the compositions and methods contemplated herein comprises mesenchymal stem and/or progenitor cells, mesodermal stem and/or progenitor cells, endodermal stem and/or progenitor cells, or ectodermal stem and/or progenitor cells. In certain embodiments, the population or source of cells used in the methods contemplated herein comprises bone marrow stem cells, umbilical cord blood stem and/or progenitor cells, bone stem and/or progenitor cells, muscle stem and/or progenitor cells, hematopoietic stem and/or progenitor cells, fat stem and/or progenitor cells, cartilage stem and/or progenitor cells, neural stem and/or progenitor cells, skin stem and/or progenitor cells, liver stem and/or progenitor cells, pancreas stem and/or progenitor cells, kidney stem and/or progenitor cells, gastric stem and/or progenitor cells, and intestinal stem and/or progenitor cells.

In certain embodiments the population or source of cells transduced using the composition and methods of the present invention include, but are not limited to, osteoblasts, chondrocytes, adipocytes, skeletal muscle, cardiac muscle, neurons, glial cells (astrocytes, oligodendrocytes, Schwann cells), retinal cells (rod cells, cone cells), corneal cells, skin cells, monocytes and macrophages, neutrophils, basophils, eosinophils, erythrocytes, megakaryocytes/platelets, dendritic cells, T-cells, B-cells, NK-cells, gastric cells, intestinal cells, smooth muscle cells, vascular cells, bladder cells, pancreatic islet cells (pancreatic alpha cells, pancreatic beta cells, pancreatic delta cells), hepatocytes, renal cells, adrenal cells, and lung cells.

In various embodiments, the use of stem cells is preferred because they have the ability to differentiate into the appropriate cell types when administered to a particular biological niche, in vivo.

In preferred embodiments, the compositions and methods of the present invention are used to increase the transduction of hematopoietic stem or progenitor cells.

The present invention also contemplates isolation and transduction of a population of cells. As used herein, the term "population of cells" refers to a plurality of cells that may be made up of any number and/or combination of homogenous or heterogeneous cell types, as described elsewhere herein. For example, for transduction of hematopoietic stem or progenitor cells, a population of cells may be isolated or obtained from umbilical cord blood, placental blood, bone marrow, or peripheral blood. A population of cells may comprise about 10%, about 20%>, about 30%, about 40%, about 50%, about 60%, about 70%, about 80%, about 90%, or about 100% of the target cell type to be transduced. In certain embodiments, hematopoietic stem or progenitor cells may be isolated or purified from a population of heterogenous cells using methods known in the art. In particular embodiments, hematopoietic stem or progenitor cells are purified after transduction of a population of cells, and in other embodiments, hematopoietic stem or progenitor cells are isolated prior to transduction.

Cells of the invention may also be cryopreserved prior to transduction or after transduction sing methods known in the art. Once established in culture, cells can be used fresh or frozen and stored as frozen stocks, using, for example, DMEM with 40% FCS and 10% DMSO. Other methods for preparing frozen stocks for cultured cells also are available to those skilled in the art.

In particular embodiments, a population of cells comprising stem or progenitor cells is contacted with a retrovirus, e.g., lentivirus, and one or more compounds that increase prostaglandin signaling, e.g., a prostaglandin EP receptor ligand such as PGE2 or an analog or derivative thereof. In certain embodiments, the population of cells is further contacted with one or more HDAC inhibitors. In various embodiments, the population of cells is contacted ex vivo, or in vivo.

In certain preferred embodiments, the stem or progenitor cells are hematopoietic stem or progenitor cells.

E. Cell Culture Compositions

The present invention further contemplates cell-based compositions comprising a culture of cells in culture medium comprising a retrovirus and one or more compounds that increase prostaglandin signaling. As discussed herein throughout, in particular embodiments, the present compositions and methods are useful for ex vivo and in vivo cell-based gene therapies. In some embodiments, the cell culture medium is a pharmaceutically acceptable cell culture medium.

A therapeutic culture, cell culture, culture system, or cell culture compositions comprising a cell-based composition of the present invention can be administered separately by enteral or parenteral administration methods or in combination with other suitable compounds to effect the desired treatment goals, e.g., one or more growth factors.

In one illustrative embodiment, a therapeutic culture, cell culture, culture system, or cell culture composition comprising a transduced cell of the present invention is administered systemically by direct injection into a tissue.

F. Compositions and Formulations

The formulations and compositions of the invention may comprise a combination of any number of transduced or non-transduced cells or a combination thereof, viral vectors, polypeptides, polynucleotides, and one or more compounds, e.g., compounds that increase prostaglandin signaling and/or HDAC inhibitors, as described herein, formulated in pharmaceutically-acceptable or physiologically-acceptable solutions/e.g., culture medium) for administration to a cell, tissue, organ, or an animal, either alone, or in combination with one or more other modalities of therapy.

Particular ex vivo and in vitro formulations and compositions of the invention may comprise a combination of transduced or non-transduced cells or a combination thereof, viral vectors, and one or more compounds, e.g., compounds that increase prostaglandin signaling and/or HDAC inhibitors, as described herein, formulated in pharmaceutically-acceptable or physiologically-acceptable solutions (e.g., culture medium) for administration to a cell, tissue, organ, or an animal, either alone, or in combination with one or more other modalities of therapy.

Particular in vivo formulations and compositions of the invention may comprise a combination of viral vectors, and one or more compounds, e.g., compounds that increase prostaglandin signaling and/or HDAC inhibitors, as described herein, formulated in pharmaceutically-acceptable or physiologically-acceptable solutions/e.g., culture medium) for administration and transduction of a cell or tissue in an animal, either alone, or in combination with one or more other modalities of therapy.

In certain embodiments, the present invention provides compositions comprising a therapeutically-effective amount of transduced cells, as described herein, formulated together with one or more pharmaceutically acceptable carriers (additives) and/or diluents (e.g., pharmaceutically acceptable cell culture medium).

In certain other embodiments, the present invention provides compositions comprising a retroviral vector and one or more compounds that increase prostaglandin EP receptor signaling, as described herein, formulated together with one or more pharmaceutically acceptable carriers (additives) and/or diluents (e.g., pharmaceutically acceptable cell culture medium).

In particular embodiments, the present invention provides compositions comprising a population of cells comprising stem or progenitor cells, a retroviral vector and one or more compounds that increase prostaglandin EP receptor signaling, as described herein, formulated together with one or more pharmaceutically acceptable carriers (additives) and/or diluents (e.g., pharmaceutically acceptable cell culture medium). In a related embodiment, the population of cells comprises hematopoietic stem and progenitor cells.

The present invention further includes pharmaceutical compositions comprising transduced cells produced according to methods described herein and a pharmaceutically acceptable carrier. In other embodiments, the present invention provides pharmaceutical compositions comprising a retroviral vector and one or more compounds, e.g., compounds that increase prostaglandin signaling and/or HDAC inhibitors, as described herein.

The phrase "pharmaceutically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

As used herein "pharmaceutically acceptable carrier" includes any and all solvents, dispersion media, coatings, antibacterial and antifungal agents, isotonic and absorption delaying agents, and the like that are physiologically compatible, including pharmaceutically acceptable cell culture media. In one embodiment, a composition comprising a carrier is suitable for parenteral administration, e.g., intravascular (intravenous or intraarterial), intraperitoneal or intramuscular administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the transduced cells, use thereof in the pharmaceutical compositions of the invention is contemplated.

The compositions of the invention may comprise one or more polypeptides, polynucleotides, vectors comprising same, compounds that increase prostaglandin EP receptor signaling, HDAC inhibitors, and transduced cells, etc., as described herein, formulated in pharmaceutically-acceptable or physiologically-acceptable solutions for administration to a cell or an animal, either alone, or in combination with one or more other modalities of therapy. It will also be understood that, if desired, the compositions of the invention may be administered in combination with other agents as well, such as, e.g., cytokines, growth factors, hormones, small molecules or various pharmaceutically-active agents. There is virtually no limit to other components that may also be included in the compositions, provided that the additional agents do not adversely affect the ability of the composition to deliver the intended gene therapy.

In the pharmaceutical compositions of the invention, formulation of pharmaceutically-acceptable excipients and carrier solutions is well-known to those of skill in the art, as is the development of suitable dosing and treatment regimens for using the particular compositions described herein in a variety of treatment regimens, including e.g., oral, parenteral, intravenous, intranasal, and intramuscular administration and formulation.

In certain circumstances it will be desirable to deliver the compositions disclosed herein parenterally, intravenously, intramuscularly, or even intraperitoneally as described, for example, in U.S. Pat. Nos. 5,543,158; 5,641,515 and 5,399, 363 (each specifically incorporated herein by reference in its entirety). Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form should be sterile and should be fluid to the extent that easy syringability exists. It should be stable under the conditions of manufacture and storage and should be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion (see, e.g., *Remington: The Science and Practice of Pharmacy,* 20th Edition. Baltimore, Md.: Lippincott Williams & Wilkins, 2005). Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by FDA Office of Biologies standards.

Sterile injectable solutions can be prepared by incorporating the active compounds in the required amount in the appropriate solvent with the various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

In certain embodiments, the compositions may be delivered by intranasal sprays, inhalation, and/or other aerosol delivery vehicles. Methods for delivering genes, polynucleotides, and peptide compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroethylene support matrix is described in U.S. Pat. No. 5,780,045 (specifically incorporated herein by reference in its entirety).

In certain embodiments, the delivery may occur by use of liposomes, nanocapsules, microparticles, microspheres, lipid particles, vesicles, optionally mixing with CPP polypeptides, and the like, for the introduction of the compositions of the present invention into suitable host cells. In particular, the compositions of the present invention may be formulated for delivery either encapsulated in a lipid particle, a liposome, a vesicle, a nanosphere, a nanoparticle or the like. The formulation and use of such delivery vehicles can be carried out using known and conventional techniques. The formulations and compositions of the invention may comprise one or more repressors and/or activators comprised of a combination of any number of polypeptides, polynucleotides, and small molecules, as described herein, formulated in pharmaceutically-acceptable or physiologically-acceptable solutions (e.g., culture medium) for administration to a cell or an animal, either alone, or in combination with one or more other modalities of therapy. It will also be understood that, if desired, the compositions of the invention may be administered in combination with other agents as well, such as, e.g., cells, other proteins or polypeptides or various pharmaceutically-active agents.

In certain embodiments, the present invention provides formulations or compositions suitable for the delivery of viral vector systems (i.e., viral-mediated transduction) including, but not limited to, retroviral/e.g., lentiviral) vectors.

Exemplary formulations for ex vivo delivery may also include the use of various transfection agents known in the art, such as calcium phosphate, electroporation, heat shock and various liposome formulations (i.e., lipid-mediated transfection). Liposomes, as described in greater detail below, are lipid bilayers entrapping a fraction of aqueous fluid. DNA spontaneously associates to the external surface of cationic liposomes (by virtue of its charge) and these liposomes will interact with the cell membrane.

In certain aspects, the present invention provides pharmaceutically acceptable compositions which comprise a therapeutically-effective amount of one or more polynucleotides or polypeptides, as described herein, formulated together with one or more pharmaceutically acceptable carriers (additives) and/or diluents (e.g., pharmaceutically acceptable cell culture medium).

Particular embodiments of the invention may comprise other formulations, such as those that are well known in the pharmaceutical art, and are described, for example, in *Remington: The Science and Practice of Pharmacy,* 20th Edition. Baltimore, Md.: Lippincott Williams & Wilkins, 2005.

In certain embodiments, compositions of the present invention comprise an effective amount of a composition and optionally comprise one or more adjunctive therapies. In certain embodiments of the present invention, compositions comprising a cell-based composition and optionally comprising one or more adjunctive therapies can further comprise sterile saline, Ringer's solution, Hanks Balanced Salt Solution (HBSS), or Isolyte S, pH 7.4, serum free cellular media, or another pharmaceutically acceptable medium (e.g., cell culture medium), as discussed elsewhere herein.

In particular embodiments, a composition comprises a population of cells is treated (e.g., contacted) with one or more compounds that increase prostaglandin EP receptor signaling and/or one or more HDAC inhibitors, each independently at a final concentration of about 1 µM to about 100 µM. In certain embodiments, a population of cells is treated with one or more compounds that increase prostaglandin EP receptor signaling and/or one or more HDAC inhibitors, each independently at a final concentration of about $1 \times 10^{-14}$ M to about $1 \times 10^{-3}$ M, about $1 \times 10^{-13}$ M to about $1 \times 10^{-4}$ M, about $1 \times 10^{-12}$ M to about $1 \times 10^{-5}$ M, about $1 \times 10^{-11}$ M to about $1 \times 10^{-4}$ M, about $1 \times 10^{-11}$ M to about $1 \times 10^{-5}$ M, about $1 \times 10^{-10}$ M to about $1 \times 10^{-4}$ M, about $1 \times 10^{-10}$ M to about $1 \times 10^{-5}$ M, about $1 \times 10^{-9}$ M to about $1 \times 10^{-4}$ M, about $1 \times 10^{-9}$ M to about $1 \times 10^{-5}$ M, about $1 \times 10^{-8}$ M to about $1 \times 10^{-4}$ M, about $1 \times 10^{-7}$ M to about $1 \times 10^{-4}$ M, about $1 \times 10^{-6}$ M to about $1 \times 10^{-4}$ M, or any intervening ranges of final concentrations.

In another particular embodiment, a population of cells is contacted with one or more compounds that increase prostaglandin EP receptor signaling and/or one or more HDAC inhibitors, each independently at a final concentration of about $1 \times 10^{-14}$ M, about $1 \times 10^{-13}$ M, about $1 \times 10^{-12}$ M, about $1 \times 10^{-10}$ M, about $1 \times 10^{-9}$ M, about $1 \times 10^{-8}$ M, about $1 \times 10^{-7}$ M to about $1 \times 10^{-6}$ M, about $1 \times 10^{-5}$ M, about $1 \times 10^{-4}$ M, about $1 \times 10^{-3}$ M, or any intervening final concentration. In compositions comprising one or more one or more compounds that increase prostaglandin EP receptor signaling and/or one or more HDAC inhibitors, the compounds can be at different concentrations from each other or at the same concentration.

One of ordinary skill in the art would be able to use routine methods in order to determine the appropriate route of administration and the correct dosage of an effective amount of a composition comprising transduced cells and/or one or more compounds that increase prostaglandin EP receptor signaling and/or one or more HDAC inhibitors for methods of the present invention. It would also be known to those having ordinary skill in the art to recognize that in certain therapies, multiple administrations of pharmaceutical compositions of the invention will be required to effect therapy.

For example a composition may be administered 1, 2, 3, 4, 5, 6, 7, 8, 9, or 10 or more times over a span of 1 week, 2 weeks, 3 weeks, 1 month, 2 months, 3 months, 4 months, 5 months, 6 months, 1 year, 2 years, 5, years, 10 years, or more.

Moreover, multiple administrations of the same or different compositions of the present invention may be administered, multiples times, for extended periods of time, as noted above.

Further, administration of the transduced cells and/or one or more compounds that increase prostaglandin EP receptor signaling and/or one or more HDAC inhibitors can be by the same route or by different routes as discussed elsewhere herein. Administration of the transduced cells and/or one or more compounds that increase prostaglandin EP receptor signaling and/or one or more HDAC inhibitors can also be performed at different sites using the same or different administration route of administration. Further, administration of the transduced cells and/or one or more compounds that increase prostaglandin EP receptor signaling and/or one or more HDAC inhibitors can be made at the same site by the same route, at the same time, or at different times.

G. Gene Therapy Methods

The transduced cells and corresponding retroviral vectors provide improved methods of gene therapy. As used herein, the term "gene therapy" refers to the introduction of a gene into a cell's genome. In various embodiments, a viral vector of the invention comprises a hematopoietic expression control sequence that expresses a therapeutic transgene encoding a polypeptide that provides curative, preventative, or ameliorative benefits to a subject diagnosed with or that is suspected of having monogenic disease, disorder, or condition or a disease, disorder, or condition that is amenable to hematopoietic stem cell therapy.

In one preferred embodiment, the invention provides transduced cells with the potential to develop into brain microglial cells. In particular embodiments, hematopoietic stem cells are transduced with a vector of the invention and administered to an individual in need of therapy for an adrenoleukodystrophy or adrenomyeloneuropathy. Hematopoietic stem cells are the origin of brain microglial cells and thus, are preferred.

In particular embodiments, transduced hematopoietic stem or progenitor cells comprise viral vectors having a hematopoietic expression control sequence that expresses a therapeutic transgene encoding a polypeptide that provides curative, preventative, or ameliorative benefits to a subject diagnosed with or that is suspected of having monogenic disease, disorder, or condition or a disease, disorder, or condition of the hematopoietic system.

A composition comprising a virus, e.g., lentivirus, and/or one or more compounds that increase prostaglandin EP receptor signaling and/or one or more HDAC inhibitors can infect and transduce cells at increased efficiencies in vivo, ex vivo, or in vitro, compared to cells transduced with vector alone. In ex vivo and in vitro embodiments, the transduced cells can then be administered to a subject in need of therapy. The present invention contemplates that the vector, viral particles, and transduced cells of the invention are be used to treat, prevent, and/or ameliorate a monogenic disease, disorder, or condition or a disease, disorder, or condition of the hematopoietic system in a subject, e.g., a hemoglobinopathy.

As used herein, "hematopoiesis," refers to the formation and development of blood cells from progenitor cells as well as formation of progenitor cells from stem cells. Blood cells include but are not limited to erythrocytes or red blood cells (RBCs), reticulocytes, monocytes, neutrophils, megakaryocytes, eosinophils, basophils, B-cells, macrophages, granulocytes, mast cells, thrombocytes, and leukocytes.

As used herein, the term "hemoglobinopathy" or "hemoglobinopathic condition" includes any disorder involving the presence of an abnormal hemoglobin molecule in the blood. Examples of hemoglobinopathies included, but are not limited to, hemoglobin C disease, hemoglobin sickle cell disease (SCD), sickle cell anemia, and thalassemias. Also included are hemoglobinopathies in which a combination of abnormal hemoglobins are present in the blood (e.g., sickle cell/Hb-C disease).

The term "sickle cell anemia" or "sickle cell disease" is defined herein to include any symptomatic anemic condition which results from sickling of red blood cells. Manifestations of sickle cell disease include: anemia; pain; and/or organ dysfunction, such as renal failure, retinopathy, acute-chest syndrome, ischemia, priapism and stroke. As used herein the term "sickle cell disease" refers to a variety of clinical problems attendant upon sickle cell anemia, especially in those subjects who are homozygotes for the sickle cell substitution in HbS. Among the constitutional manifestations referred to herein by use of the term of sickle cell disease are delay of growth and development, an increased tendency to develop serious infections, particularly due to pneumococcus, marked impairment of splenic function, preventing effective clearance of circulating bacteria, with recurrent infarcts and eventual destruction of splenic tissue. Also included in the term "sickle cell disease" are acute episodes of musculoskeletal pain, which affect primarily the lumbar spine, abdomen, and femoral shaft, and which are similar in mechanism and in severity to the bends. In adults, such attacks commonly manifest as mild or moderate bouts of short duration every few weeks or months interspersed with agonizing attacks lasting 5 to 7 days that strike on average about once a year. Among events known to trigger such crises are acidosis, hypoxia and dehydration, all of which potentiate intracellular polymerization of HbS (J. H. Jandl, *Blood: Textbook of Hematology*, 2nd Ed., Little, Brown and Company, Boston, 1996, pages 544-545). As used herein, the term "thalassemia" encompasses hereditary anemias that occur due to mutations affecting the synthesis of hemoglobin. Thus, the term includes any symptomatic anemia resulting from thalassemic conditions such as severe or β-thalassemia, thalassemia major, thalassemia intermedia, a thalassemias such as hemoglobin H disease.

As used herein, "thalassemia" refers to a hereditary disorder characterized by defective production of hemoglobin. Examples of thalassemias include a and β thalassemia. β-thalassemias are caused by a mutation in the beta globin chain, and can occur in a major or minor form. In the major form of β-thalassemia, children are normal at birth, but develop anemia during the first year of life. The minor form of β-thalassemia produces small red blood cells. Thalassemia minor occurs if you receive the defective gene from only one parent. Persons with this form of the disorder are carriers of the disease and usually do not have symptoms.

a-thalassemia typically results from deletions involving the HBA1 and HBA2 genes. Both of these genes encode a-globin, which is a component (subunit) of hemoglobin. There are two copies of the HBA1 gene and two copies of the HBA2 gene in each cellular genome. As a result, there are four alleles that produce a-globin. The different types of a-thalassemia result from the loss of some or all of these alleles. Hb Bart syndrome, the most severe form of α-thalassemia, results from the loss of all four α-globin alleles. HbH disease is caused by a loss of three of the four α-globin alleles. In these two conditions, a shortage of α-globin prevents cells from making normal hemoglobin. Instead, cells produce abnormal forms of hemoglobin called hemoglobin Bart (Hb Bart) or hemoglobin H (HbH). These abnormal hemoglobin molecules cannot effectively carry oxygen to the body's tissues. The substitution of Hb Bart or HbH for normal hemoglobin causes anemia and the other serious health problems associated with a-thalassemia.

In a preferred embodiment, gene therapy methods of the invention are used to treat, prevent, or ameliorate a hemoglobinopathy is selected from the group consisting of: hemoglobin C disease, hemoglobin sickle cell disease (SCD), sickle cell anemia, hereditary anemia, thalassemia, β-thalassemia, thalassemia major, thalassemia intermedia, α-thalassemia, and hemoglobin H disease.

In various embodiments, the retroviral vectors are administered by direct injection to a cell, tissue, or organ of a subject in need of gene therapy, in vivo. In various other embodiments, cells are transduced in vitro or ex vivo with vectors of the invention, and optionally expanded ex vivo. The transduced cells are then administered to a subject in need of gene therapy.

Cells suitable for transduction and administration in the gene therapy methods of the invention include, but are not limited to stem cells, progenitor cells, and differentiated cells as described elsewhere herein. In certain embodiments, the transduced cells are embryonic stem cells, induced pluripotent stem cells, bone marrow stem cells, umbilical cord stem cells, placental stem cells, mesenchymal stem cells, neural stem cells, liver stem cells, pancreatic stem cells, cardiac stem cells, kidney stem cells, hematopoietic stem cells as described elsewhere herein.

In preferred embodiments, the transduced cells are hematopoietic stem and/or progenitor cells isolated from bone marrow, umbilical cord blood, or peripheral circulation. In particular preferred embodiments, the transduced cells are hematopoietic stem cells isolated from bone marrow, umbilical cord blood, or peripheral circulation.

HSCs may be identified according to certain phenotypic or genotypic markers. For example, HSCs may be identified by their small size, lack of lineage (lin) markers, low staining (side population) with vital dyes such as rhodamine 123 (rhodamineDULL, also called rholo) or Hoechst 33342, and presence of various antigenic markers on their surface, many of which belong to the cluster of differentiation series (e.g., CD34, CD38, CD90, CD133, CD105, CD45, Terl 19, and c-kit, the receptor for stem cell factor). HSCs are mainly negative for the markers that are typically used to detect lineage commitment, and, thus, are often referred to as Lin(−) cells.

In one embodiment, human HSCs may be characterized as CD34+, CD59+, Thy1/CD90+, CD38lo/−, C-kit/CD117+, and Lin(−). However, not all stem cells are covered by these combinations, as certain HSCs are CD34−/CD38−. Also some studies suggest that earliest stem cells may lack c-kit on the cell surface. For human HSCs, CD 133 may represent an early marker, as both CD34+ and CD34− HSCs have been shown to be CD133+. It is known in the art that CD34+ and Lin(−) cells also include hematopoietic progenitor cells.

In another embodiment, the hematopoietic hierarchy is determined by a SLAM code. The SLAM (Signaling lymphocyte activation molecule) family is a group of >10 molecules whose genes are located mostly tandemly in a single locus on chromosome 1 (mouse), all belonging to a subset of immunoglobulin gene superfamily, and originally thought to be involved in T-cell stimulation. This family includes CD48, CD 150, CD244, etc., CD 150 being the founding member, and, thus, also called slamF1, i.e., SLAM family member 1. The signature SLAM code for the hematopoietic hierarchy is hematopoietic stem cells (HSC)—CD150+CD48−CD244−; multipotent progenitor cells (MPPs)—CD150−CD48−CD244+; lineage-restricted progenitor cells (LRPs)—CD150−CD48+CD244+; common myeloid progenitor (CMP)—lin−SCA-1−c-kit+CD34+ CD16/32mid; granulocyte-macrophage progenitor (GMP)—lin−SCA-1−c-kit+CD34+CD16/32hi; and megakaryocyte-erythroid progenitor (MEP)—lin−SCA-1−c-kit+ CD34−CD16/32low.

In mice, Irving Weissman's group at Stanford University was the first to isolate mouse hematopoietic stem cells in 1988 and was also the first to work out the markers to distinguish the mouse hematopoietic hierarchy. The markers for the hematopoietic hierarchy is long-term hematopoietic stem cells (LT-HSC)—CD34−, SCA-1+, Thy1.1+/lo, C-kit+, lin−, CD135−, Slamfl/CD150+; short-term hematopoietic stem cells (ST-HSC)—CD34+, SCA-1+, Thy1.1+/lo, C-kit+, lin−, CD 135−, Slamfl/CD150+, Mac-1 (CD11b)lo; early multipotent progenitors—(Early MPP)—CD34+, SCA-1+, Thy1.1−, C-kit+, lin−, CD135+, Slamfl/CD150−, Mac-1 (CD11b)lo, CD4lo; and late multipotent progenitors (Late MPP)—CD34+, SCA-1+, Thy1.1−, C-kit+, lin−, CD135high, Slamfl/CD150−, Mac-1 (CD11b)lo, CD4lo.

In one embodiment, the hematopoietic cells are CD105+ Sca1+ cells.

Cells of the invention can be autologous/autogeneic ("self") or non-autologous ("non-self," e.g., allogeneic, syngeneic or xenogeneic). "Autologous," as used herein, refers to cells from the same subject. "Allogeneic," as used herein, refers to cells of the same species that differ genetically to the cell in comparison. "Syngeneic," as used herein, refers to cells of a different subject that are genetically identical to the cell in comparison. "Xenogeneic," as used herein, refers to cells of a different species to the cell in comparison. In preferred embodiments, the cells of the invention are allogeneic.

A "subject," as used herein, includes any animal that exhibits a symptom of a monogenic disease, disorder, or condition that can be treated with the gene therapy vectors, cell-based therapeutics, and methods disclosed elsewhere herein. In preferred embodiments, a subject includes any animal that exhibits symptoms of a disease, disorder, or condition of the hematopoietic system, e.g., a hemoglobinopathy, that can be treated with the gene therapy vectors, cell-based therapeutics, and methods disclosed elsewhere herein. Suitable subjects (e.g., patients) include laboratory animals (such as mouse, rat, rabbit, or guinea pig), farm animals, and domestic animals or pets (such as a cat or dog). Non-human primates and, preferably, human patients, are included. Typical subjects include animals that exhibit aberrant amounts (lower or higher amounts than a "normal" or "healthy" subject) of one or more physiological activities that can be modulated by gene therapy.

As used herein "treatment" or "treating," includes any beneficial or desirable effect on the symptoms or pathology of a disease or pathological condition, and may include even minimal reductions in one or more measurable markers of the disease or condition being treated. Treatment can involve optionally either the reduction or amelioration of symptoms of the disease or condition, or the delaying of the progression of the disease or condition. "Treatment" does not necessarily indicate complete eradication or cure of the disease or condition, or associated symptoms thereof.

As used herein, "prevent," and similar words such as "prevented," "preventing" etc., indicate an approach for preventing, inhibiting, or reducing the likelihood of the occurrence or recurrence of, a disease or condition. It also refers to delaying the onset or recurrence of a disease or condition or delaying the occurrence or recurrence of the symptoms of a disease or condition. As used herein, "prevention" and similar words also includes reducing the intensity, effect, symptoms and/or burden of a disease or condition prior to onset or recurrence of the disease or condition.

As used herein, the term "amount" refers to "an amount effective" or "an effective amount" of a virus or transduced therapeutic cell to achieve a beneficial or desired prophylactic or therapeutic result, including clinical results.

A "prophylactically effective amount" refers to an amount of a virus or transduced therapeutic cell effective to achieve the desired prophylactic result. Typically but not necessarily, since a prophylactic dose is used in subjects prior to or at an earlier stage of disease, the prophylactically effective amount is less than the therapeutically effective amount.

A "therapeutically effective amount" of a virus or transduced therapeutic cell may vary according to factors such as the disease state, age, sex, and weight of the individual, and the ability of the stem and progenitor cells to elicit a desired response in the individual. A therapeutically effective amount is also one in which any toxic or detrimental effects of the virus or transduced therapeutic cells are outweighed by the therapeutically beneficial effects. The term "therapeutically effective amount" includes an amount that is effective to "treat" a subject (e.g., a patient).

Without wishing to be bound to any particular theory, an important advantage provided by the vectors, compositions, and methods of the present invention is the high efficacy of gene therapy that can be achieved by administering populations of cells comprising high percentages of transduced cells compared to existing methods.

The transduced cells may be administered as part of a bone marrow or cord blood transplant in an individual that has or has not undergone bone marrow ablative therapy. In one embodiment, transduced cells of the invention are administered in a bone marrow transplant to an individual that has undergone chemoablative or radioablative bone marrow therapy.

In one embodiment, a dose of transduced cells is delivered to a subject intravenously. In preferred embodiments, transduced hematopoietic stem cells are intravenously administered to a subject.

In one illustrative embodiment, the effective amount of transduced cells provided to a subject is less than $1 \times 10^{12}$ cells per 100 kg, less than $1 \times 10^{11}$ cells per 100 kg, less than $1 \times 10^{10}$ cells per 100 kg, less than $1 \times 10^{9}$ cells per 100 kg, less than $1 \times 10^{8}$ cells per 100 kg, less than $1 \times 10^{7}$ cells per 100 kg, less than $5 \times 10^{6}$ cells per 100 kg, less than $4 \times 10^{6}$ cells per 100 kg, less than $3 \times 10^{6}$ cells per 100 kg, less than $2 \times 10^{6}$ cells per 100 kg, less than $1 \times 10^{6}$ cells per 100 kg, less than $5 \times 10^{5}$ cells per 100 kg, less than $4 \times 10^{5}$ cells per 100 kg, less than $3 \times 10^{5}$ cells per 100 kg, less than $2 \times 10^{5}$ cells per 100 kg, less than $1 \times 10^{5}$ cells per 100 kg, less than $5 \times 10^{4}$ cells per 100 kg, or less than $1 \times 10^{4}$ cells per 100 kg of the subject's bodyweight.

In another illustrative embodiment, the effective amount of transduced cells provided to a subject is about $1 \times 10^{12}$ cells per 100 kg, about $1 \times 10^{11}$ cells per 100 kg, about $1 \times 10^{10}$ cells per 100 kg, about $1 \times 10^{9}$ cells per 100 kg, about $1 \times 10^{8}$ cells per 100 kg, about $1 \times 10^{7}$ cells per 100 kg, about $5 \times 10^{6}$ cells per 100 kg, about $4 \times 10^{6}$ cells per 100 kg, about $3 \times 10^{6}$ cells per 100 kg, about $2 \times 10^{6}$ cells per 100 kg, about $1 \times 10^{6}$ cells per 100 kg, about $5 \times 10^{5}$ cells per 100 kg, about $4 \times 10^{5}$ cells per 100 kg, about $3 \times 10^{5}$ cells per 100 kg, about $2 \times 10^{5}$ cells per 100 kg, about $1 \times 10^{5}$ cells per 100 kg, about $5 \times 10^{4}$ cells per 100 kg, or about $1 \times 10^{4}$ cells per 100 kg.

In another illustrative embodiment, the effective amount of transduced cells provided to a subject is from about $1 \times 10^{1}$ cells per 100 kg to about $1 \times 10^{12}$ cells per 100 kg, from about $1 \times 10^{2}$ cells per 100 kg to about $1 \times 10^{11}$ cells per 100 kg, from about $1 \times 10^{3}$ cells per 100 kg to about $1 \times 10^{10}$ cells per 100 kg, from about $1 \times 10^{4}$ cells per 100 kg to about $1 \times 10^{9}$ cells per 100 kg, from about $1 \times 10^{5}$ cells per 100 kg to about $1 \times 10^{8}$ cells per 100 kg, from about $1 \times 10^{6}$ cells per 100 kg to about $1 \times 10^{7}$ cells per 100 kg, or any intervening ranges of cells per 100 kg.

In various embodiments, the methods of the invention provide more robust and safer gene therapy than existing methods and comprise administering a population or dose of cells comprising about 5% transduced cells, about 10% transduced cells, about 15% transduced cells, about 20%> transduced cells, about 25% transduced cells, about 30%> transduced cells, about 35% transduced cells, about 40%> transduced cells, about 45% transduced cells, about 50% transduced cells, about 55% transduced cells, about 60% transduced cells, about 65% transduced cells, about 70% transduced cells, about 75% transduced cells, about 80% transduced cells, about 85% transduced cells, about 90% transduced cells, about 95% transduced cells, about 98% transduced cells, or about 100% transduced cells, to a subject.

In various embodiments, the vectors, compositions, and methods of the present invention offer improved methods of gene therapy using ex vivo gene therapy and autologous transplantation. In one preferred embodiment, the invention provides transduced cells, such as a stem cell, e.g., hematopoietic stem cell. In particular embodiments, hematopoietic stem cells are transduced with a vector of the invention and administered to an individual in need of therapy for a hemoglobinopathy.

In particular embodiments, hematopoietic stem cells are transduced with a vector of the invention and administered to an individual in need of therapy for an adrenoleukodystrophy or an adrenomyeloneuropathy.

In one preferred embodiment, the invention provides improved viral vector systems optimized to express high levels of one or more therapeutic proteins in erythroid cells or erythroid precursor cells. Retroviral vectors, including lentiviral vectors, of the invention further comprise a polynucleotide-of-interest, including, for example, a globin gene or a gene which encodes an antisickling protein. In one embodiment, the globin gene expressed in the retroviral vector of the invention is β-globin, δ-globin, or γ-globin. In another embodiment, the human β-globin gene is the wild type human β-globin gene or human $β^{-A}$-globin gene. In another embodiment, the human β-globin gene comprises one or more deletions of intron sequences or is a mutated human β-globin gene encoding at least one antisickling amino acid residue. Antisickling amino acids can be derived from human δ-globin or human γ-globin. In another embodiment, the mutated human β-globin gene encodes a threonine to glutamine mutation at codon 87 ($β^{-A-T87([<]BEGINITALm)}$).

Retroviral vectors, including lentiviral vectors, of the invention can be used in gene therapy, including for the treatment of hemoglobinopathies. In particular embodiments, the invention provides methods for using the foregoing vectors to achieve stable, high levels of gene expression in erythroid cells, e.g., in order to treat erythroid-specific diseases. In a particular embodiment, the gene therapy vectors are used to treat hemoglobinopathies, including, for example, sickle cell disease (SCD). In another preferred embodiment, the gene therapy vectors are used for treatment of thalassemias, including, but not limited to, β-thalassemia.

In another preferred embodiment, hematopoietic stem cells are transduced with vectors of the invention comprising an ABCD1 gene for treatment of adrenoleukodystropies and/or adrenomyeloneuropathies.

The present invention now will be described more fully by the following examples. This invention may, however, be embodied in many different forms and should not be construed as limited to the embodiments set forth herein; rather, these embodiments are provided so that this disclosure will be thorough and complete, and will fully convey the scope of the invention to those skilled in the art.

EXAMPLES

Example 1

Prestimulation of Cells for Transduction

One vial of CD34+ cells (AUCells) were thawed by incubating at 37° C. for 1-2 minutes and contents were transferred to 10 mL Stem Cell Growth Media (hereafter referred to as SCGM) in a 15-mL conical tube. Cells were spun for 5 minutes at 1500 RPM in a standard tabletop centrifuge, resuspended in 10 mL SCGM and counted on a hemacytometer. A volume correlating with an appropriate number of cells was transferred to a fresh 15-mL conical tube, and again spun for 5 minutes at 1500 RPM. Cells were resuspended to the desired cell concentration in SCGM+1× cytokines (100 ng/niL SCF, 100 ng/niL TPO, 100 ng/niL FltL, and 30 ng/niL IL-3), and plated on a sterile non-adherent surface at 37° C. in a standard humidified tissue culture incubator (5% $CO_2$).

A screen for compounds that increase viral transduction efficiency of CD34+ cells was conducted using varying concentrations of soluble compounds from a number of classes (Table 1). The results of the screen are shown in FIG. 1.

TABLE 1

| Concentration | Wnt3 | FGF1 | IGF-II | SHH | Stemregenin-1 | dmPGE2 |
|---|---|---|---|---|---|---|
| High | 100 ng/mL | 100 ng/mL | 200 ng/mL | 100 ng/mL | 1000 nM | 100 uM |
| Medium | 10 ng/mL | 10 ng/mL | 20 ng/mL | 10 ng/mL | 100 nM | 10 uM |
| Low | 1 ng/mL | 1 ng/mL | 2 ng/mL | 1 ng/mL | 10 nM | 1 uM |

| Concentration | SC514 | Omuralide | Epoxomicin | AMD3100 | B18R | TrichostatinA |
|---|---|---|---|---|---|---|
| High | 10 um | 1000 nm | 10 uM | 100 ng/mL | 200 ng/mL | 3000 nM |
| Medium | 1 um | 100 nm | 1 uM | 10 ng/mL | 20 ng/mL | 300 nM |
| Low | 0.1 um | 10 nm | 0.1 uM | 1 ng/mL | 2 ng/mL | 30 nM |

Example 2

Transduction

Pre-stimulated cells (Example 1) were counted after 18-24 hours of culture. The cells were collected and spun for 5 minutes at 1500 RPM. $1.2 \times 10^6$ pre-stimulated CD34 cells were resuspended in 60 uL 10× cytokines (1000 ng/mL SCF, 1000 ng/mL TPO, 1000 ng/mL FltL, and 300 ng/mL IL-3), 7.8 uL protamine sulfate, 111 uL viral supernatant, and 361.2 uL SCGM. 90 uL cell/virus suspension (about 200,000 cells) was added to each well of a standard non-adherent 96-well plate. dmPGE2 was added during this viral transduction step at a final concentration of 100 uM, 50 uM, 25 uM, 12.5 uM, 1 uM, or 0 uM. The viral stock had a titer of $2.7 \times 10^8$ TU/mL, and the multiplicity of infection (MOI) was about 25.

Cells were incubated at 37° C. in a standard humidified tissue culture incubator (5% $CO_2$).

Example 3

DMPGE 2 Stimulation of Cells

Aliquots of 10 mM dmPGE2 in DMSO were prepared from 1 mg previously processed dmPGE2 (Cayman Chemicals). Briefly, air was pipetted into the vial of dmPGE2 until methyl acetate was evaporated. 263 uL DMSO was added to the PGE2 remaining in the vial, and aliquots of 25 uL were added to 1.5 mL Eppendorf tubes and stored at −80° C. 10× working stock solutions were prepared by serial dilution of dmPGE2 in SCGM, and were then added to cells at appropriate working concentrations, according to Table 2. Cells were then incubated at 37° C. in a standard humidified tissue culture incubator (5% $CO_2$).

TABLE 2

Serial Dilutions of dmPGE2 and Addition of dmPGE2 to Cells

|  | Stock A | Stock B | Stock C | Stock D | Stock E |
|---|---|---|---|---|---|
| Frozen Stock dmPGE2 | 20 | 0 | 0 | 0 | 0 |
| Volume SCGM | 180 | 100 | 100 | 100 | 92.5 |
| Volume of Stock A | 0 | 100 | 0 | 0 | 0 |
| Volume of Stock B | 0 | 0 | 100 | 0 | 0 |
| Volume of Stock C | 0 | 0 | 0 | 100 | 0 |
| Volume of Stock D | 0 | 0 | 0 | 0 | 8 |
| Concentration of dmPGE2 | 1 mM | 500 uM | 250 uM | 125 uM | 10 uM |
| For Final Concentration of: | 100 uM | 50 uM | 25 uM | 12.5 uM | 1 uM |
| Add 10 uL of: | Stock A | Stock B | Stock C | Stock D | Stock E |

Example 4

Validation Assays

Cell Preparation for Validation Assays

After 24 hours of culture with virus and dmPGE2, cells were washed prior to subsequent functional validation assays. Washing was performed by transferring cells to a 96-well U-bottom plate and spinning for 5 minutes at 1500 RPM in a standard tabletop centrifuge. Media was aspirated and cells were resuspended in 200 uL SCGM. Cells were spun again for 5 minutes at 1500 RPM and media was aspirated. Cells were again resuspended in 200 uL SCGM then spun for 5 minutes at 1500 RPM, and again the media was aspirated. Particular functional validation assays are described below.

7-Day Liquid Culture

Washed cells were resuspended in 200 uL SCGM+1× cytokines (as described in Example 1) and transferred to a standard 12-well non-adherent tissue culture plate containing an additional 800 uL SCGM+1× cytokines. Cells were maintained for an additional 6 days in a standard humidified tissue culture incubator (5% CO2) and then subjected Vector Copy Number analysis (Example 5) and FACS analysis. For FACS analysis, cells were assayed for the presence of a virally-encoded transgene, green fluorescent protein (GFP).

The frequency of the virally-labeled cells within the pool of cultured cells was quantified as the frequency of GFP+ cells within the population. The mean fluorescence intensity of labeled cells was quantified. Results for the 7-Day Liquid Culture Assay with varying concentrations of dmPGE2 are shown in Table 3.

Assessment of Colony Forming Unit Activity in Methylcellulose

Washed cells were resuspended in 200 uL SCGM and then transferred to 3 mL aliquots of cytokine-supplemented methylcellulose (for example, Methocult M4434 Classic). 15 mL was then transferred to parallel 35-mm tissue culture dishes using a blunt 16-gauge needle. Dishes were maintained in a standard humidified tissue culture incubator for 14-16 days and colonies were scored for size, morphology, and cellular composition. Individual colonies were then picked for subsequent Vector Copy Number analysis (Example 5) or the contents of an entire 35-mm dish were pooled and then subject to Vector Copy Number analysis (Example 5).

Long Term Culture-Initiating Cells (LTC-IQ

Cells were resuspended in 200 uL SCGM, counted, and then transferred to pre-plated MS-5 stromal layer at various dilutions (2000; 1000; 500; 250; 125; 62; 31; 16 cells per well in 200 µL of StemSpan SFEM (StemCell Technologies, cat #09650), supplemented with Pen-Strep 100 U/mL-100 µg/mL) and 24 replicates per dilution. At weekly intervals 100 µL was replaced by 100 µL of fresh media. At 5 weeks, the cultures were harvested. 100 µL were discarded, cells were flushed with the 100 µL remaining and the well was rinsed with 50 µL of fresh media, and the whole contents were seeded in Methocult™ H4434; 150 µL of cell suspension were homogenized with 600 µL of Methocult H4434 and plated in one well of a 12 well-plate for 14 days. Colonies were then counted. The number of wells containing at least one colony (>40 cells) and the total number of wells analyzed for each dilution were used to calculate the frequency of LTC-ICs and the 95% confidence interval using the L-calc software (Stem Cell Technologies). 100 colonies from each treatment group were picked into 100 different wells and individually scored for the presence of the vector. 100 colonies from each treatment group were pooled, genomic DNA was extracted and the mean Vector Copy Number was assessed by qPCR (Example 5).

Transplantation into NOD/SCID Gamma (NSG) Mice

To determine whether dmPGE2 promotes viral transduction of human long-term hematopoietic stem cells with minimal residual toxicity, transduced cells were washed and resuspended in phosphate-buffered saline (PBS) and transplanted into the tail vein of irradiated adult NSG mice. Mice were housed in a pathogen-free environment per standard IACUC animal care guidelines. At staged timepoints, human donor-derived contribution to peripheral blood was quantified by collecting from the mouse via standard protocols. Briefly, red blood cells were pelleted with 2% Dextran and then the supernatant was further cleared through treatment with red cell lysis buffer. Mononuclear cells were then stained with fluorophore-conjugated antibodies as described by Majeti, et al., *Cell Stem Cell* 2007, and analyzed by flow cytometry on an LSR-II (Becton Dickinson).

Integration Site Analysis

To determine whether dmPGE2 changes the integration site preference of lentiviral vector, bone marrow samples from mice transplanted with dmPGE2-treated and mock-treated virally transduced human hematopoietic stem and progenitor cells were subjected to linear amplification-mediated PCR (Cartier, (2009) *Science* 326(5954):818-23).

In brief, 1-1000 ng of DNA served as template for linear PCR using retroviral LTR-specific biotinylated primers. Linear PCR products were separated with paramagnetic beads. Further second strand DNA synthesis, restriction digest (Tsp509I, NlaIII or HpyCH4IV) and ligation of a linker cassette were accomplished on semisolid phase, followed by two additional exponential PCR steps. The resulting LAM-PCR amplicons were further prepared for 454 pyrosequencing (GS Fix; Roche Diagnostics) by performing an additional exponential PCR to add the GS Fix specific amplification and sequencing primers A and B to both ends of the LAM-PCR amplicons. Primer design was done as suggested by the manufacturer. A recognition sequence of 6 bases was incorporated to primer A to simultaneously analyze different samples in a single sequencing run. 40 ng of purified LAM-PCR products were used. PCR conditions were as follows: initial denaturation for 120 s at 95° C.; 12 cycles at 95° C., for 45 s, 60° C. for 45 s and 72° C. for 60 s; final elongation 300 s at 72° C. LAM-PCR amplicon sequences were trimmed and aligned using BLAST.

Example 5

Vector Copy Number Analysis

Briefly, total genomic DNA was isolated from cells through standard protocols (for example, through DNEasy columns from Qiagen). Genomic DNA was subjected to quantitative real-time polymerase chain reaction (qRT-PCR) with TaqMan probes for viral LTR and human beta-actin. The Ct values for viral signal and beta-actin signal were normalized to a standardized control, and the number of viral copies per copy of beta actin were calculated. A linear relationship between the vector copy number and the mean fluorescence intensity (Example 4) was observed when a viral construct that encodes GFP was used. Results for the Vector Copy Number (VCN) Analysis with varying concentrations of dmPGE2 are shown in Tables 3A-C.

Tables 3A-C indicate the dose-response of dmPGE2 in promoting viral transduction of CD34+ cells for three separate experiments. CD34+ cells were thawed and pre-stimulated with SCF, TPO, FltL, and IL3, then transduced (A) with GFP+ lentivirus at a multiplicity of infection of 25, (B) with GFP+ lentivirus at a multiplicity of infection of 5, or (C) transduced with an ALD (ABCD1)-expressing lentivirus at a multiplicity of infection of 25. Cells were exposed to dmPGE2 during the viral transduction step (24-48 hours of culture). Cells were then washed and analyzed by flow cytometry and PCR after approximately 1 week in culture. The percentage of cells positive for GFP (A, B) or ALD (C) via FACS staining is indicated, along with the mean fluorescent intensity (MFI) and vector copy number (VCN) (A, B).

TABLE 3A

| GFP MOI 25 | | | |
|---|---|---|---|
| Conc dmPGE2 | % Positive (GFP) | MFI | VCN |
| 100 uM | 81.53 | 1,513,504.00 | 3.55 |
| 50 uM | 67.62 | 977,806.75 | 2.2 |
| 25 uM | 59.99 | 845,691,00 | 1.7 |
| 12.5 uM | 54.71 | 759,442.75 | 1.5 |
| 0 uM | 30.07 | 583,079.25 | 0.535 |
| No Virus | 0.02 | 290,577.50 | N.D. |

TABLE 3B

| GFP MOI 5 | | | |
|---|---|---|---|
| Conc dmPGE2 | % Positive (GFP) | MFI | VCN |
| 100 uM | 42.97 | 732,716.25 | 0.83 |
| 50 uM | 36.80 | 656,703.50 | 0.715 |
| 25 uM | 18.69 | 562,428.00 | 0.21 |
| 12.5 uM | 17.84 | 530,218.50 | 0.18 |
| 0 uM | 9.05 | 477,691.00 | 0.025 |
| No Virus | 0.02 | 290,577.50 | N.D. |

TABLE 3C

| ABCD1 MOI 25 | |
|---|---|
| Conc dmPGE2 | % Positive |
| 100 uM | 72.26 |
| 50 uM | 56.10 |
| 25 uM | 43.76 |
| 12.5 uM | 45.36 |
| 1 uM | 34.13 |
| 0 uM | 21.44 |

Example 6

Time-Course and Dose-Response of DMPGE 2 in Promoting Viral Transduction of CD34+ Cells MCD-34+ cells were thawed and pre-stimulated with SCF, TPO, FltL and IL3, then transduced with GFP+ lentivirus at a multiplicity of infection of 25. Cells were exposed to dmPGE2 during the viral transduction step (24-25 hours of culture; 24-26 hours of culture; 24-28 hours of culture; or 24-48 hours of culture) and then washed and analyzed by flow cytometry after approximately 1 week in culture. Alternatively, cells were exposed to dmPGE2 during the pre-stimulation step (22-24 hours of culture; 23-24 hours of culture). The percentage of cells positive for GFP is indicated in Table 4.

TABLE 4

| Conc dmPGE2 | Virus and PGE2 | | | | Pre-Stim w/PGE2 | |
|---|---|---|---|---|---|---|
| | Plus 1 Hr | Plus 2 Hr | Plus 4 Hr | 24 Hr | Minus 2 Hr | Minus 1 Hr |
| 100 uM | 2.48 | 4.02 | 21.57 | 76.44 | 34.85 | 25.14 |
| 50 uM | 1.85 | 4.23 | 27.45 | 54.63 | 31.85 | 22.98 |
| 25 uM | 1.76 | 4.76 | 27.46 | 50.69 | 31.90 | 24.05 |
| 12.5 uM | 1.97 | 5.32 | 28.08 | 47.42 | 30.64 | 22.13 |
| 1 uM | 2.94 | 7.17 | 21.10 | 32.03 | 25.74 | 22.29 |
| 0 uM | 3.14 | 7.05 | 13.61 | 20.79 | 20.69 | 21.31 |

Example 7

Correction of Beta-Thalassemia or Sickle Cell Disease after Transduction of HSC with Lentiviral Vectors in the Presence of DMPGE 2

Mobilized peripheral blood is to be collected by apheresis from patients with informed consent and in accordance with approved institutional review board (IRB) protocols A Ficoll gradient will be used to remove erythrocytes, and CD34-enriched cells obtained following CD34+ selection using the Miltenyi CliniMACS system (Miltenyi Biotec). Cells are to be pre-stimulated with human SCF, FltL, TPO, and IL3 at a concentration of approximately 4E6 cells/mL for 18-24 hours. Cells are then transduced with Lentiglobin GTP, harboring a human β-globinA-T87Q gene, at a multiplicity of infection of 25 for 18-24 hours in the presence of SCF, FltL, TPO, IL3, protamine sulfate, and dmPGE2.

Following transduction, a portion of cells are removed for release testing, and the remainder cryopreserved and stored at −80° C. As part of release testing, transduced cells for an individual are then subjected to 7-Day culture and VCN analysis (Example 1) to verify 0.5 to 3 copies per cell average, as well as >50% transduction efficiency. Upon successful release testing, patients will undergo treatment with busulfan and cyclophosphamide.

The dose of autologous CD34+ cells is then administered intravenously to the subject in a single intravenous dose of >3×10$^6$ CD34+ cells/kg. Patients are followed daily in the transplant unit for adverse events and laboratory parameters to monitor bone marrow engraftment.

Once engraftment occurs and patients are stable, they are discharged from the hospital and followed monthly for 6 months and at least every 3 months for a total of 24 months. Evaluations will include routine hematology and chemistry safety laboratory assessment and special hematologic testing, bone marrow examination, collection of adverse events and concomitant medications, and evaluation of specific disease-specific hematologic and clinical parameters.

The primary endpoints are safety and tolerability of the Lentiglobin-transduced cell infusion and time to engraftment of the autologous, manipulated CD34+ cells. Additional endpoints include biological and biochemical measures of the presence of the transduced gene and gene product in hematopoietic and blood cells, transfusion requirements, and the number of hospitalizations and clinical events occurring at various time periods during the course of the 2-year follow-up period. All patients will be followed at least yearly for a total of 15 years post-transplant for serious adverse events, RCL testing, and banking of blood cells for insertional mutagenesis testing in the event that a malignancy develops.

Example 8

Correction of Adrenoleukodystrophy after Transduction of HSC with Lentiviral Vectors in the Presence of DMPGE 2

Mobilized peripheral blood is to be collected by apheresis from patients with informed consent and in accordance with approved institutional review board (IRB) protocols. A Ficoll gradient will be used to remove erythrocytes, and CD34-enriched cells obtained following CD34+ selection using the Miltenyi CliniMACS system (Miltenyi Biotec). Cells are to be pre-stimulated with human SCF, FltL, TPO, and IL3 at a concentration of approximately 4E6 cells/mL for 18-24 hours. Cells are then transduced with Lenti-D GTP, harboring a human ABCD1 gene, at a multiplicity of infection of 25 for 18-24 hours in the presence of SCF, FltL, TPO, IL3, protamine sulfate, and dmPGE2.

Following transduction, a portion of cells are removed for release testing, and the remainder cryopreserved and stored at −80° C. As part of release testing, transduced cells for an individual are then subjected to 7-Day culture and VCN analysis (Example 1) to verify 0.5 to 3 copies per cell average, as well as >50% transduction efficiency. Upon successful release testing, patients will undergo treatment with busulfan and cyclophosphamide.

The dose of autologous CD34+ cells is then administered intravenously to the subject in a single intravenous dose of >3×10⁶ CD34+ cells/kg. Patients are followed daily in the transplant unit for adverse events and laboratory parameters to monitor bone marrow engraftment.

Once engraftment occurs and patients are stable, they are discharged from the hospital and followed monthly for 6 months and at least every 3 months for a total of 24 months. Evaluations will include routine hematology and chemistry safety laboratory assessment and special hematologic testing, bone marrow examination, collection of adverse events and concomitant medications, and evaluation of specific disease-specific hematologic and clinical parameters.

The primary endpoints are safety and tolerability of the Lenti-D-transduced cell infusion and time to engraftment of the autologous, manipulated CD34+ cells. Additional endpoints include biological and biochemical measures of the presence of the transduced gene and gene product in hematopoietic and blood cells, brain MRI and cognitive studies, and the number of hospitalizations and clinical events occurring at various time periods during the course of the 2-year follow-up period. All patients will be followed at least yearly for a total of 15 years post-transplant for serious adverse events, RCL testing, and banking of blood cells for insertional mutagenesis testing in the event that a malignancy develops.

As one skilled in the art will readily recognize having read the present disclosure, numerous modifications can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A method for increasing the lentiviral vector transduction efficiency of CD34+ hematopoietic stem or progenitor cells comprising:
   contacting the CD34+ hematopoietic stem or progenitor cells with a culture medium comprising a lentiviral vector and prostaglandin $E_2$ ($PGE_2$), 16,16-dimethyl $PGE_2$, or an analogue thereof, ex vivo
   wherein the lentiviral vector transduction efficiency is increased in the CD34+ hematopoietic stem or progenitor cells contacted with the culture medium compared to the lentiviral vector transduction efficiency of CD34+ hematopoietic stem or progenitor cells contacted with a culture medium comprising the lentiviral vector in the absence of $PGE_2$, 16,16-dimethyl $PGE_2$, or an analogue thereof.

2. The method of claim 1, wherein the CD34+ hematopoietic stem or progenitor cells are CD34+ hematopoietic stem cells.

3. The method of claim 1, wherein the CD34+ hematopoietic stem or progenitor cells are CD34+ hematopoietic progenitor cells.

4. The method of claim 1, wherein
   a) at least 50% of the CD34+ hematopoietic stem or progenitor cells are transduced;
   b) at least 75% of the CD34+ hematopoietic stem or progenitor cells are transduced; or
   c) at least 90% of the CD34+ hematopoietic stem or progenitor cells are transduced.

5. The method of claim 1, wherein the medium further comprises a histone deacetylase (HDAC) inhibitor.

6. The method of claim 5, wherein the HDAC inhibitor is selected from the group consisting of: Trichostatin A (TSA), valproic acid (VPA), sodium butyrate, suberoylanilide hydroxamic acid (SAHA), sodium phenylbutyrate, depsipeptide, trapoxin (TPX), cyclic hydroxamic acid-containing peptide 1 (CHAP1), MS-275, LBH589, and PXD-101.

7. The method of claim 1, wherein the lentiviral vector is derived from a Human immunodeficiency virus (HIV) virus.

8. The method of claim 1, wherein the lentiviral vector is pseudotyped with a vesicular stomatitis virus G-protein (VSV-G) envelope protein.

9. The method of claim 1, wherein the CD34+ hematopoietic stem or progenitor cells are contacted with the culture medium comprising the lentiviral vector and $PGE_2$, 16,16-dimethyl $PGE_2$, or an analogue thereof for at least twenty-four hours.

10. The method of claim 1, wherein the lentiviral vector comprises:
   a) a left (5') lentiviral long terminal repeat (LTR) comprising a heterologous promoter;
   b) an expression control sequence operably linked to a gene of interest; and
   c) a right (3') lentiviral SIN LTR.

11. The method of claim 1, wherein the lentiviral vector comprises:
   a) a left (5') HIV-1 LTR comprising a CMV promoter;
   b) a Psi packaging sequence (Ψ+);
   c) an HIV-1 central polypurine tract/DNA flap (cPPT/FLAP);
   d) a rev response element (RRE);
   e) a β-globin promoter and a β-globin locus control region (LCR) operably linked to a gene of interest; and
   f) a right (3') lentiviral SIN LTR that comprises
      i) one or more insulator elements, or
      ii) a rabbit β-globin polyA (rβgpA) sequence.

12. The method of claim 1, wherein the lentiviral vector comprises:
   a) a left (5') HIV-1 LTR comprising a CMV promoter;
   b) a Psi (Ψ+) packaging signal;
   c) a cPPT/FLAP;
   d) an RRE;
   e) a myeloproliferative sarcoma virus enhancer, negative control region deleted, d1587rev primer-binding site substituted (MND) promoter, operably linked to a polynucleotide encoding a human ATP-binding cassette, sub-family D, member 1 (ABCD1) polypeptide;
   f) a right (3') HIV-1 SIN LTR; and
   g) a rβgpA sequence.

13. A method for increasing the lentiviral transduction efficiency of CD34+ hematopoietic stem or progenitor cells comprising:
   contacting the CD34+ hematopoietic stem or progenitor cells with a culture medium comprising a lentiviral vector and $PGE_2$, ex vivo
   wherein the lentiviral transduction efficiency is increased in the CD34+ hematopoietic stem or progenitor cells contacted with the culture medium compared to the lentiviral transduction efficiency of CD34+ hematopoietic stem or progenitor cells contacted with a culture medium comprising the lentiviral vector in the absence of $PGE_2$.

14. The method of claim 13, wherein
   a) at least 50% of the CD34+ hematopoietic stem or progenitor cells are transduced;
   b) at least 75% of the CD34+ hematopoietic stem or progenitor cells are transduced; or
   c) at least 90% of the CD34+ hematopoietic stem or progenitor cells are transduced.

15. The method of claim 13, wherein the lentiviral vector is derived from an HIV virus.

16. The method of claim 13, wherein the lentiviral vector is pseudotyped with a VSV-G envelope protein.

17. The method of claim 13, wherein the CD34+ hematopoietic stem or progenitor cells are contacted with the culture medium comprising the lentiviral vector and PGE2 for at least twenty-four hours.

18. The method of claim 13, wherein the lentiviral vector comprises:
   a) a left (5') lentiviral LTR comprising a heterologous promoter;
   b) an expression control sequence operably linked to a gene of interest; and
   c) a right (3') lentiviral SIN LTR.

19. The method of claim 13, wherein the lentiviral vector comprises:
   a) a left (5') HIV-1 LTR comprising a CMV promoter;
   b) a Psi packaging sequence (Ψ+);
   c) an HIV-1 cPPT/FLAP;
   d) an RRE;

e) a β-globin promoter and a β-globin LCR operably linked to a gene of interest; and
f) a right (3') lentiviral SIN LTR that comprises
   i) one or more insulator elements, or
   ii) a rβgpA sequence.

20. The method of claim 13, wherein the lentiviral vector comprises:
   a) a left (5') HIV-1 LTR comprising a CMV promoter;
   b) a Psi (Ψ+) packaging signal;
   c) a cPPT/FLAP;
   d) an RRE;
   e) an MND promoter, operably linked to a polynucleotide encoding a human ABCD1 polypeptide;
   f) a right (3') HIV-1 SIN LTR; and
   g) a rβgpA sequence.

21. A method for increasing the lentiviral transduction efficiency of CD34+ hematopoietic stem or progenitor cells comprising:
   contacting the CD34+ hematopoietic stem or progenitor cells with a culture medium comprising a lentiviral vector and 16,16-dimethyl $PGE_2$, ex vivo
   wherein the lentiviral transduction efficiency is increased in the CD34+ hematopoietic stem or progenitor cells contacted with the culture medium compared to the lentiviral transduction efficiency of CD34+ hematopoietic stem or progenitor cells contacted with a culture medium comprising the lentiviral vector in the absence of 16,16-dimethyl $PGE_2$.

22. The method of claim 21, wherein
   a) at least 50% of the CD34+ hematopoietic stem or progenitor cells are transduced;
   b) at least 75% of the CD34+ hematopoietic stem or progenitor cells are transduced; or
   c) at least 90% of the CD34+ hematopoietic stem or progenitor cells are transduced.

23. The method of claim 21, wherein the lentiviral vector is derived from an HIV-1 virus.

24. The method of claim 21, wherein the lentiviral vector is pseudotyped with a VSV-G envelope protein.

25. The method of claim 21, wherein the CD34+ hematopoietic stem or progenitor cells are contacted with the culture medium comprising the lentiviral vector and 16,16-dimethyl $PGE_2$ for at least twenty-four hours.

26. The method of claim 21, wherein the lentiviral vector comprises:
   a) a left (5') lentiviral LTR comprising a heterologous promoter;
   b) an expression control sequence operably linked to a gene of interest; and
   c) a right (3') lentiviral SIN LTR.

27. The method of claim 21, wherein the lentiviral vector comprises:
   a) a left (5') HIV-1 LTR comprising a CMV promoter;
   b) a Psi packaging sequence (Ψ+);
   c) an HIV-1 cPPT/FLAP;
   d) an RRE;
   e) a β-globin promoter and a β-globin LCR operably linked to a gene of interest; and
   f) a right (3') lentiviral SIN LTR that comprises
      i) one or more insulator elements, or
      ii) a rβgpA sequence.

28. The method of claim 21, wherein the lentiviral vector comprises:
   a) a left (5') HIV-1 LTR comprising a CMV promoter;
   b) a Psi (Ψ+) packaging signal;
   c) a cPPT/FLAP;
   d) an RRE;
   e) an MND promoter, operably linked to a polynucleotide encoding a human ABCD1 polypeptide;
   f) a right (3') HIV-1 SIN LTR; and
   g) a rβgpA sequence.

* * * * *

SEQUENCE LISTING

<160> NUMBER OF SEQ ID NOS: 18

<210> SEQ ID NO 1
<211> LENGTH: 576
<212> TYPE: DNA
<213> ORGANISM: Homo sapiens

<400> SEQUENCE: 1

```
actcttctgg tccccacaga ctcagagaga acccaccatg gtgctgtctc ctgccgacaa    60
gaccaacgtc aaggccgcct ggggtaaggt cggcgcgcac gctggcgagt atggtgcgga   120
ggccctggag aggatgttcc tgtccttccc caccaccaag acctacttcc cgcacttcga   180
cctgagccac ggctctgccc aggttaaggg ccacggcaag aaggtggccg acgcgctgac   240
caacgccgtg gcgcacgtgg acgacatgcc caacgcgctg tccgccctga gcgacctgca   300
cgcgcacaag cttcgggtgg acccggtcaa cttcaagctc ctaagccact gcctgctggt   360
gaccctggcc gcccacctcc ccgccgagtt caccccctgcg gtgcacgcct ccctggacaa   420
gttcctggct tctgtgagca ccgtgctgac ctccaaatac cgttaagctg agcctcggt    480 ggccatgctt cttgcccctt gggcctcccc ccagcccctc ctccccttcc tgcacccgta   540
cccccgtggt ctttgaataa agtctgagtg ggcggc                              576
```

<210> SEQ ID NO 2
<211> LENGTH: 142
<212> TYPE: PRT
<213> ORGANISM: Homo sapiens

<400> SEQUENCE: 2

```
Met Val Leu Ser Pro Ala Asp Lys Thr Asn Val Lys Ala Ala Trp Gly
1               5                   10                  15

Lys Val Gly Ala His Ala Gly Glu Tyr Gly Ala Glu Ala Leu Glu Arg
            20                  25                  30

Met Phe Leu Ser Phe Pro Thr Thr Lys Thr Tyr Phe Pro His Phe Asp
        35                  40                  45

Leu Ser His Gly Ser Ala Gln Val Lys Gly His Gly Lys Lys Val Ala
    50                  55                  60

Asp Ala Leu Thr Asn Ala Val Ala His Val Asp Asp Met Pro Asn Ala
65                  70                  75                  80

Leu Ser Ala Leu Ser Asp Leu His Ala His Lys Leu Arg Val Asp Pro
                85                  90                  95
```

```
Val Asn Phe Lys Leu Leu Ser His Cys Leu Leu Val Thr Leu Ala Ala
            100                 105                 110

His Leu Pro Ala Glu Phe Thr Pro Ala Val His Ala Ser Leu Asp Lys
        115                 120                 125

Phe Leu Ala Ser Val Ser Thr Val Leu Thr Ser Lys Tyr Arg
        130                 135                 140
```

<210> SEQ ID NO 3
<211> LENGTH: 142
<212> TYPE: PRT
<213> ORGANISM: Mus musculus

<400> SEQUENCE: 3

```
Met Val Leu Ser Gly Glu Asp Lys Ser Asn Ile Lys Ala Ala Trp Gly
1               5                   10                  15

Lys Ile Gly Gly His Gly Ala Glu Tyr Gly Ala Glu Ala Leu Glu Arg
            20                  25                  30

Met Phe Ala Ser Phe Pro Thr Thr Lys Thr Tyr Phe Pro His Phe Asp
        35                  40                  45

Val Ser His Gly Ser Ala Gln Val Lys Gly His Gly Lys Lys Val Ala
    50                  55                  60

Asp Ala Leu Ala Asn Ala Ala Gly His Leu Asp Asp Leu Pro Gly Ala
65                  70                  75                  80

Leu Ser Ala Leu Ser Asp Leu His Ala His Lys Leu Arg Val Asp Pro
                85                  90                  95

Val Asn Phe Lys Leu Leu Ser His Cys Leu Leu Val Thr Leu Ala Ser
            100                 105                 110

His His Pro Ala Asp Phe Thr Pro Ala Val His Ala Ser Leu Asp Lys
        115                 120                 125

Phe Leu Ala Ser Val Ser Thr Val Leu Thr Ser Lys Tyr Arg
        130                 135                 140
```

<210> SEQ ID NO 4
<211> LENGTH: 142
<212> TYPE: PRT
<213> ORGANISM: Rattus norvegicus

<400> SEQUENCE: 4

```
Met Val Leu Ser Ala Asp Asp Lys Thr Asn Ile Lys Asn Cys Trp Gly
1               5                   10                  15

Lys Ile Gly Gly His Gly Gly Glu Tyr Gly Glu Glu Ala Leu Gln Arg
            20                  25                  30

Met Phe Ala Ala Phe Pro Thr Thr Lys Thr Tyr Phe Ser His Ile Asp
        35                  40                  45

Val Ser Pro Gly Ser Ala Gln Val Lys Ala His Gly Lys Lys Val Ala
    50                  55                  60

Asp Ala Leu Ala Lys Ala Ala Asp His Val Glu Asp Leu Pro Gly Ala
65                  70                  75                  80

Leu Ser Thr Leu Ser Asp Leu His Ala His Lys Leu Arg Val Asp Pro
                85                  90                  95

Val Asn Phe Lys Phe Leu Ser His Cys Leu Leu Val Thr Leu Ala Cys
            100                 105                 110

His His Pro Gly Asp Phe Thr Pro Ala Met His Ala Ser Leu Asp Lys
        115                 120                 125

Phe Leu Ala Ser Val Ser Thr Val Leu Thr Ser Lys Tyr Arg
        130                 135                 140
```

<210> SEQ ID NO 5
<211> LENGTH: 626
<212> TYPE: DNA
<213> ORGANISM: Homo sapiens

<400> SEQUENCE: 5

```
acatttgctt ctgacacaac tgtgttcact agcaacctca aacagacacc atggtgcatc      60
tgactcctga ggagaagtct gccgttactg ccctgtgggg caaggtgaac gtggatgaag     120
ttggtggtga ggccctgggc aggctgctgg tggtctaccc ttggacccag aggttctttg     180
agtcctttgg ggatctgtcc actcctgatg ctgttatggg caaccctaag gtgaaggctc     240
atggcaagaa agtgctcggt gcctttagtg atggcctggc tcacctggac aacctcaagg     300
gcacctttgc cacactgagt gagctgcact gtgacaagct gcacgtggat cctgagaact     360
tcaggctcct gggcaacgtg ctggtctgtg tgctggccca tcactttggc aaagaattca     420
ccccaccagt gcaggctgcc tatcagaaag tggtggctgg tgtggctaat gccctggccc     480
acaagtatca ctaagctcgc tttcttgctg tccaatttct attaaaggtt cctttgttcc     540
ctaagtccaa ctactaaact gggggatatt atgaagggcc ttgagcatct ggattctgcc     600
taataaaaaa catttatttt cattgc                                          626
```

<210> SEQ ID NO 6
<211> LENGTH: 147
<212> TYPE: PRT
<213> ORGANISM: Homo sapiens

<400> SEQUENCE: 6

```
Met Val His Leu Thr Pro Glu Glu Lys Ser Ala Val Thr Ala Leu Trp
1               5                   10                  15

Gly Lys Val Asn Val Asp Glu Val Gly Gly Glu Ala Leu Gly Arg Leu
            20                  25                  30

Leu Val Val Tyr Pro Trp Thr Gln Arg Phe Phe Glu Ser Phe Gly Asp
        35                  40                  45

Leu Ser Thr Pro Asp Ala Val Met Gly Asn Pro Lys Val Lys Ala His
    50                  55                  60

Gly Lys Lys Val Leu Gly Ala Phe Ser Asp Gly Leu Ala His Leu Asp
65                  70                  75                  80

Asn Leu Lys Gly Thr Phe Ala Thr Leu Ser Glu Leu His Cys Asp Lys
                85                  90                  95

Leu His Val Asp Pro Glu Asn Phe Arg Leu Leu Gly Asn Val Leu Val
            100                 105                 110

Cys Val Leu Ala His His Phe Gly Lys Glu Phe Thr Pro Pro Val Gln
        115                 120                 125

Ala Ala Tyr Gln Lys Val Val Ala Gly Val Ala Asn Ala Leu Ala His
    130                 135                 140

Lys Tyr His
145
```

<210> SEQ ID NO 7
<211> LENGTH: 147
<212> TYPE: PRT
<213> ORGANISM: Homo sapiens

<400> SEQUENCE: 7

```
Met Val His Leu Thr Pro Glu Glu Lys Ser Ala Val Thr Ala Leu Trp
1               5                   10                  15
```

```
Gly Lys Val Asn Val Asp Glu Val Gly Glu Ala Leu Gly Arg Leu
            20                  25                  30

Leu Val Val Tyr Pro Trp Thr Gln Arg Phe Phe Glu Ser Phe Gly Asp
        35                  40                  45

Leu Ser Thr Pro Asp Ala Val Met Gly Asn Pro Lys Val Lys Ala His
 50                  55                  60

Gly Lys Lys Val Leu Gly Ala Phe Ser Asp Gly Leu Ala His Leu Asp
65                  70                  75                  80

Asn Leu Lys Gly Thr Phe Ala Gln Leu Ser Glu Leu His Cys Asp Lys
                85                  90                  95

Leu His Val Asp Pro Glu Asn Phe Arg Leu Leu Gly Asn Val Leu Val
               100                 105                 110

Cys Val Leu Ala His His Phe Gly Lys Glu Phe Thr Pro Pro Val Gln
           115                 120                 125

Ala Ala Tyr Gln Lys Val Val Ala Gly Val Ala Asn Ala Leu Ala His
       130                 135                 140

Lys Tyr His
145

<210> SEQ ID NO 8
<211> LENGTH: 147
<212> TYPE: PRT
<213> ORGANISM: Mus musculus

<400> SEQUENCE: 8

Met Val His Leu Thr Asp Ala Glu Lys Ala Ala Val Ser Gly Leu Trp
1               5                   10                  15

Gly Lys Val Asn Ala Asp Glu Val Gly Gly Glu Ala Leu Gly Arg Leu
            20                  25                  30

Leu Val Val Tyr Pro Trp Thr Gln Arg Tyr Phe Asp Ser Phe Gly Asp
        35                  40                  45

Leu Ser Ser Ala Ser Ala Ile Met Gly Asn Ala Lys Val Lys Ala His
 50                  55                  60

Gly Lys Lys Val Ile Thr Ala Phe Asn Asp Gly Leu Asn His Leu Asp
65                  70                  75                  80

Ser Leu Lys Gly Thr Phe Ala Ser Leu Ser Glu Leu His Cys Asp Lys
                85                  90                  95

Leu His Val Asp Pro Glu Asn Phe Arg Leu Leu Gly Asn Met Ile Val
               100                 105                 110

Ile Val Leu Gly His His Leu Gly Lys Asp Phe Thr Pro Ala Ala Gln
           115                 120                 125

Ala Ala Phe Gln Lys Val Val Ala Gly Val Ala Ala Ala Leu Ala His
       130                 135                 140

Lys Tyr His
145

<210> SEQ ID NO 9
<211> LENGTH: 147
<212> TYPE: PRT
<213> ORGANISM: Rattus norvegicus

<400> SEQUENCE: 9

Met Val His Leu Thr Asp Ala Glu Lys Ala Ala Val Asn Gly Leu Trp
1               5                   10                  15

Gly Lys Val Asn Pro Asp Asp Val Gly Gly Glu Ala Leu Gly Arg Leu
            20                  25                  30
```

```
Leu Val Val Tyr Pro Trp Thr Gln Arg Tyr Phe Asp Ser Phe Gly Asp
            35                  40                  45

Leu Ser Ser Ala Ser Ala Ile Met Gly Asn Pro Lys Val Lys Ala His
 50                  55                  60

Gly Lys Lys Val Ile Asn Ala Phe Asn Asp Gly Leu Lys His Leu Asp
 65                  70                  75                  80

Asn Leu Lys Gly Thr Phe Ala His Leu Ser Glu Leu His Cys Asp Lys
                 85                  90                  95

Leu His Val Asp Pro Glu Asn Phe Arg Leu Leu Gly Asn Met Ile Val
            100                 105                 110

Ile Val Leu Gly His His Leu Gly Lys Glu Phe Thr Pro Cys Ala Gln
         115                 120                 125

Ala Ala Phe Gln Lys Val Val Ala Gly Val Ala Ser Ala Leu Ala His
         130                 135                 140

Lys Tyr His
145

<210> SEQ ID NO 10
<211> LENGTH: 583
<212> TYPE: DNA
<213> ORGANISM: Homo sapiens

<400> SEQUENCE: 10
acactcgctt ctggaacgtc tgaggttatc aataagctcc tagtccagac gccatgggtc      60
atttcacaga ggaggacaag gctactatca caagcctgtg gggcaaggtg aatgtggaag     120
atgctggagg agaaaccctg ggaaggctcc tggttgtcta cccatggacc cagaggttct     180
ttgacagctt tggcaacctg tcctctgcct ctgccatcat gggcaacccc aaagtcaagg     240
cacatggcaa gaaggtgctg acttccttgg gagatgccat aaagcacctg gatgatctca     300
agggcacctt tgcccagctg agtgaactgc actgtgacaa gctgcatgtg gatcctgaga     360
acttcaagct cctgggaaat gtgctggtga ccgttttggc aatccatttc ggcaaagaat     420
tcacccctga ggtgcaggct tcctggcaga gatggtgac tggagtggcc agtgccctgt      480
cctccagata ccactgagct cactgcccat gatgcagagc tttcaaggat aggctttatt     540
ctgcaagcaa tcaaataata aatctattct gctaagagat cac                       583

<210> SEQ ID NO 11
<211> LENGTH: 147
<212> TYPE: PRT
<213> ORGANISM: Homo sapiens

<400> SEQUENCE: 11

Met Gly His Phe Thr Glu Glu Asp Lys Ala Thr Ile Thr Ser Leu Trp
  1               5                  10                  15

Gly Lys Val Asn Val Glu Asp Ala Gly Gly Glu Thr Leu Gly Arg Leu
                 20                  25                  30

Leu Val Val Tyr Pro Trp Thr Gln Arg Phe Phe Asp Ser Phe Gly Asn
            35                  40                  45

Leu Ser Ser Ala Ser Ala Ile Met Gly Asn Pro Lys Val Lys Ala His
 50                  55                  60

Gly Lys Lys Val Leu Thr Ser Leu Gly Asp Ala Ile Lys His Leu Asp
 65                  70                  75                  80

Asp Leu Lys Gly Thr Phe Ala Gln Leu Ser Glu Leu His Cys Asp Lys
                 85                  90                  95

Leu His Val Asp Pro Glu Asn Phe Lys Leu Leu Gly Asn Val Leu Val
```

```
            100                 105                 110
Thr Val Leu Ala Ile His Phe Gly Lys Glu Phe Thr Pro Glu Val Gln
        115                 120                 125

Ala Ser Trp Gln Lys Met Val Thr Gly Val Ala Ser Ala Leu Ser Ser
    130                 135                 140

Arg Tyr His
145

<210> SEQ ID NO 12
<211> LENGTH: 147
<212> TYPE: PRT
<213> ORGANISM: Mus musculus

<400> SEQUENCE: 12

Met Val His Phe Thr Ala Glu Glu Lys Ala Ala Ile Thr Ser Ile Trp
1               5                   10                  15

Asp Lys Val Asp Leu Glu Lys Val Gly Gly Glu Thr Leu Gly Arg Leu
            20                  25                  30

Leu Ile Val Tyr Pro Trp Thr Gln Arg Phe Phe Asp Lys Phe Gly Asn
        35                  40                  45

Leu Ser Ser Ala Leu Ala Ile Met Gly Asn Pro Arg Ile Arg Ala His
    50                  55                  60

Gly Lys Lys Val Leu Thr Ser Leu Gly Leu Gly Val Lys Asn Met Asp
65                  70                  75                  80

Asn Leu Lys Glu Thr Phe Ala His Leu Ser Glu Leu His Cys Asp Lys
                85                  90                  95

Leu His Val Asp Pro Glu Asn Phe Lys Leu Leu Gly Asn Met Leu Val
            100                 105                 110

Ile Val Leu Ser Thr His Phe Ala Lys Glu Phe Thr Pro Glu Val Gln
        115                 120                 125

Ala Ala Trp Gln Lys Leu Val Ile Gly Val Ala Asn Ala Leu Ser His
    130                 135                 140

Lys Tyr His
145

<210> SEQ ID NO 13
<211> LENGTH: 147
<212> TYPE: PRT
<213> ORGANISM: Rattus norvegicus

<400> SEQUENCE: 13

Met Val His Phe Thr Ala Glu Glu Lys Ala Ala Ile Ile Ser Ile Trp
1               5                   10                  15

Glu Lys Val Asp Leu Glu Lys Ile Gly Gly Glu Thr Leu Gly Arg Leu
            20                  25                  30

Leu Ile Val Tyr Pro Trp Thr Gln Arg Phe Phe Asp Lys Phe Gly Asn
        35                  40                  45

Leu Ser Ser Ala Leu Ala Ile Met Gly Asn Pro Arg Ile Arg Ala His
    50                  55                  60

Gly Lys Lys Val Leu Thr Ser Leu Gly Ser Ala Val Glu Asn Met Asp
65                  70                  75                  80

Asn Leu Lys Glu Thr Phe Ala His Leu Ser Glu Leu His Cys Asp Lys
                85                  90                  95

Leu His Val Asp Pro Gln Asn Phe Lys Leu Leu Gly Asn Met Leu Val
            100                 105                 110

Ile Val Leu Ser Thr His Phe Ala Lys Glu Phe Thr Pro Glu Val Gln
```

```
                    115                 120                 125
Ala Ala Trp Gln Lys Leu Val Met Gly Val Ala Asn Ala Leu Ser His
    130                 135                 140

Lys Tyr His
145

<210> SEQ ID NO 14
<211> LENGTH: 774
<212> TYPE: DNA
<213> ORGANISM: Homo sapiens

<400> SEQUENCE: 14
agggcaagtt aagggaatag tggaatgaag gttcattttt cattctcaca aactaatgaa      60
accctgctta tcttaaacca acctgctcac tggagcaggg aggacaggac cagcataaaa     120
ggcagggcag agtcgactgt tgcttacact ttcttctgac ataacagtgt tcactagcaa     180
cctcaaacag acaccatggt gcatctgact cctgaggaga agactgctgt caatgccctg     240
tggggcaaag tgaacgtgga tgcagttggt ggtgaggccc tgggcagatt actggtggtc     300 taccccttgga cccagaggtt ctttgagtcc tttgggatc tgtcctctcc tgatgctgtt     360
atgggcaacc ctaaggtgaa ggctcatggc aagaaggtgc taggtgcctt tagtgatggc     420
ctggctcacc tggacaacct caagggcact ttttctcagc tgagtgagct gcactgtgac     480
aagctgcacg tggatcctga aacttcagg ctcttgggca atgtgctggt gtgtgtgctg     540
gcccgcaact ttggcaagga attcacccca caaatgcagg ctgcctatca gaaggtggtg     600
gctggtgtgg ctaatgccct ggctcacaag taccattgag atcctggact gtttcctgat     660
aaccataaga agaccctatt tccctagatt ctattttctg aacttgggaa cacaatgcct     720
acttcaaggg tatggcttct gcctaataaa gaatgttcag ctcaacttcc tgat           774

<210> SEQ ID NO 15
<211> LENGTH: 147
<212> TYPE: PRT
<213> ORGANISM: Homo sapiens

<400> SEQUENCE: 15

Met Val His Leu Thr Pro Glu Glu Lys Thr Ala Val Asn Ala Leu Trp
1               5                   10                  15

Gly Lys Val Asn Val Asp Ala Val Gly Gly Glu Ala Leu Gly Arg Leu
                20                  25                  30

Leu Val Val Tyr Pro Trp Thr Gln Arg Phe Phe Glu Ser Phe Gly Asp
            35                  40                  45

Leu Ser Ser Pro Asp Ala Val Met Gly Asn Pro Lys Val Lys Ala His
    50                  55                  60

Gly Lys Lys Val Leu Gly Ala Phe Ser Asp Gly Leu Ala His Leu Asp
65                  70                  75                  80

Asn Leu Lys Gly Thr Phe Ser Gln Leu Ser Glu Leu His Cys Asp Lys
                85                  90                  95

Leu His Val Asp Pro Glu Asn Phe Arg Leu Leu Gly Asn Val Leu Val
            100                 105                 110

Cys Val Leu Ala Arg Asn Phe Gly Lys Glu Phe Thr Pro Gln Met Gln
        115                 120                 125

Ala Ala Tyr Gln Lys Val Val Ala Gly Val Ala Asn Ala Leu Ala His
    130                 135                 140

Lys Tyr His
145
```

<210> SEQ ID NO 16
<211> LENGTH: 2297
<212> TYPE: DNA
<213> ORGANISM: Homo sapiens

<400> SEQUENCE: 16

```
ccagccccag tccctacgcg gcagccagcc caggtgacat gccggtgctc tccaggcccc      60
ggccctggcg ggggaacacg ctgaagcgca cggccgtgct cctggccctc gcggcctatg     120
gagcccacaa agtctacccc ttggtgcgcc agtgcctggc ccggccagg ggtcttcagg      180
cgcccgccgg ggagcccacg caggaggcct ccggggtcgc ggcggccaaa gctggcatga     240
accgggtatt cctgcagcgg ctcctgtggc tcctgcggct gctgttcccc cgggtcctgt     300
gccgggagac ggggctgctg gccctgcact cggccgcctt ggtgagccgc accttcctgt     360
cggtgtatgt ggcccgcctg gacggaaggc tggcccgctg catcgtccgc aaggacccgc     420
gggcttttgg ctggcagctg ctgcagtggc tcctcatcgc cctccctgct accttcgtca     480
acagtgccat ccgttacctg gagggccaac tggccctgtc gttccgcagc cgtctggtgg     540
cccacgccta ccgcctctac ttctcccagc agacctacta ccgggtcagc aacatggacg     600
gcggcttcg caaccctgac cagtctctga cggaggacgt ggtggccttt gcggcctctg     660
tggcccacct ctactccaac ctgaccaagc cactcctgga cgtggctgtg acttcctaca     720
ccctgcttcg ggcggcccgc tcccgtggag ccggcacagc ctggccctcg ccatcgccg      780
gcctcgtggt gttcctcacg gccaacgtgc tgcgggcctt ctcgcccaag ttcggggagc     840
tggtggcaga ggaggcgcgg cggaagggg agctgcgcta catgcactcg cgtgtggtgg      900
ccaactcgga ggagatcgcc ttctatgggg ccatgaggt ggagctggcc ctgctacagc      960
gctcctacca ggacctggcc tcgcagatca acctcatcct tctggaacgc ctgtggtatg    1020
ttatgctgga gcagttcctc atgaagtatg tgtggagcgc ctcgggcctg ctcatggtgg    1080
ctgtccccat catcactgcc actggctact cagagtcaga tgcagaggcc gtgaagaagg    1140
cagccttgga aaagaaggag gaggagctgg tgagcgagcg cacagaagcc ttcactattg    1200
cccgcaacct cctgacagcg gctgcagatg ccattgagcg gatcatgtcg tcgtacaagg    1260
aggtgacgga gctggctggc tacacagccc gggtgcacga gatgttccag gtatttgaag    1320
atgttcagcg ctgtcacttc aagaggccca gggagctaga ggacgctcag gcggggtctg    1380
ggaccatagg ccggtctggt gtccgtgtgg agggccccct gaagatccga ggccaggtgg    1440
tggatgtgga cagggggatc atctgcgaga acatccccat cgtcacgccc tcaggagagg    1500
tggtggtggc cagcctcaac atcagggtgg aggaaggcat gcatctgctc atcacaggcc    1560
ccaatggctg cggcaagagc tccctgttcc ggatcctggg tggctctgg ccacgtacg     1620
gtggtgtgct ctacaagccc ccaccccagc gcatgttcta catcccgcag aggccctaca    1680
tgtctgtggg ctccctgcgt gaccaggtga tctacccgga ctcagtggag gacatgcaaa    1740
ggaagggcta ctcggagcag gacctggaag ccatcctgga cgtcgtgcac ctgcaccaca    1800
tcctgcagcg ggagggaggt tgggaggcta tgtgtgactg gaaggacgtc ctgtcgggtg    1860
gcgagaagca gagaatcggc atggcccgca tgttctacca caggcccaag tacgccctcc    1920
tggatgaatg caccagcgcc gtgagcatcg acgtggaagg caagatcttc caggcggcca    1980
aggacgcggg cattgccctg ctctccatca cccaccggcc ctccctgtgg aaataccaca    2040
cacacttgct acagttcgat ggggagggcg gctggaagtt cgagaagctg gactcagctg    2100
```

| cccgcctgag | cctgacggag | gagaagcagc | ggctggagca | gcagctggcg | ggcattccca | 2160 |
| agatgcagcg | cgcgcctccag | gagctctgcc | agatcctggg | cgaggccgtg | gccccagcgc | 2220 |
| atgtgccggc | acctagcccg | caaggccctg | gtggcctcca | gggtgcctcc | acctgactcg | 2280 |
| aggggggggcc | cggtacc | | | | | 2297 |

<210> SEQ ID NO 17
<211> LENGTH: 2238
<212> TYPE: DNA
<213> ORGANISM: Homo sapiens

<400> SEQUENCE: 17

| atgccggtgc | tctccaggcc | ccggccctgg | cgggggaaca | cgctgaagcg | cacggccgtg | 60 |
| ctcctggccc | tcgcggccta | tggagcccac | aaagtctacc | ccttggtgcg | ccagtgcctg | 120 |
| gcccggcca | ggggtcttca | ggcgcccgcc | ggggagccca | cgcaggaggc | ctccggggtc | 180 |
| gcggcggcca | aagctggcat | gaaccgggta | ttcctgcagc | ggctcctgtg | gctcctgcgg | 240 |
| ctgctgttcc | ccgggtcct | gtgccgggag | acggggctgc | tggccctgca | ctcggccgcc | 300 |
| ttggtgagcc | gcaccttcct | gtcggtgtat | gtggcccgcc | tggacggaag | gctggcccgc | 360 |
| tgcatcgtcc | gcaaggaccc | gcgggctttt | ggctggcagc | tgctgcagtg | gctcctcatc | 420 |
| gccctccctg | ctaccttcgt | caacagtgcc | atccgttacc | tggagggcca | actggccctg | 480 |
| tcgttccgca | gccgtctggt | ggcccacgcc | taccgcctct | acttctccca | gcagacctac | 540 |
| taccgggtca | gcaacatgga | cgggcggctt | cgcaaccctg | accagtctct | gacggaggac | 600 |
| gtggtggcct | ttgcggcctc | tgtggcccac | ctctactcca | acctgaccaa | gccactcctg | 660 |
| gacgtggctg | tgacttccta | caccctgctt | cgggcggccc | gctcccgtgg | agccggcaca | 720 |
| gcctggccct | cggccatcgc | cggcctcgtg | gtgttcctca | cggccaacgt | gctgcgggcc | 780 |
| ttctcgccca | gttcggggga | gctggtggca | gaggaggcgc | ggcggaaggg | ggagctgcgc | 840 |
| tacatgcact | cgcgtgtggt | ggccaactcg | gaggagatcg | ccttctatgg | gggccatgag | 900 |
| gtggagctgg | ccctgctaca | gcgctcctac | caggacctgg | cctcgcagat | caacctcatc | 960 |
| cttctggaac | gcctgtggta | tgttatgctg | gagcagttcc | tcatgaagta | tgtgtggagc | 1020 |
| gcctcgggcc | tgctcatggt | ggctgtcccc | atcatcactg | ccactggcta | ctcagagtca | 1080 |
| gatgcagagg | ccgtgaagaa | ggcagccttg | gaaaagaagg | aggaggagct | ggtgagcgag | 1140 |
| cgcacagaag | ccttcactat | tgcccgcaac | ctcctgacag | cggctgcaga | tgccattgag | 1200 |
| cggatcatgt | cgtcgtacaa | ggaggtgacg | gagctggctg | gctacacagc | ccgggtgcac | 1260 |
| gagatgttcc | aggtatttga | agatgttcag | cgctgtcact | tcaagaggcc | cagggagcta | 1320 |
| gaggacgctc | aggcggggtc | tgggaccata | ggccggtctg | gtgtccgtgt | ggagggcccc | 1380 |
| ctgaagatcc | gaggccaggt | ggtggatgtg | aacaggggga | tcatctgcga | aacatcccc | 1440 |
| atcgtcacgc | cctcaggaga | ggtggtggtg | gccagcctca | acatcagggt | ggaggaaggc | 1500 |
| atgcatctgc | tcatcacagg | ccccaatggc | tgcggcaaga | gctccctgtt | ccggatcctg | 1560 |
| ggtgggctct | ggcccacgta | cggtggtgtg | ctctacaagc | cccaccccca | gcgcatgttc | 1620 |
| tacatcccgc | agaggcccta | catgtctgtg | ggctccctgc | gtgaccaggt | gatctacccg | 1680 |
| gactcagtgg | aggacatgca | aaggaagggc | tactcggagc | aggacctgga | agccatcctg | 1740 |
| gacgtcgtgc | acctgcacca | catcctgcag | cgggagggag | gttgggaggc | tatgtgtgac | 1800 |
| tggaaggacg | tcctgtcggg | tggcgagaag | cagagaatcg | gcatggcccg | catgttctac | 1860 |
| cacaggccca | gtacgcccct | cctggatgaa | tgcaccagcg | ccgtgagcat | cgacgtggaa | 1920 |

```
ggcaagatct tccaggcggc caaggacgcg ggcattgccc tgctctccat cacccaccgg  1980
ccctccctgt ggaaatacca cacacacttg ctacagttcg atggggaggg cggctggaag  2040
ttcgagaagc tggactcagc tgcccgcctg agcctgacgg aggagaagca gcggctggag  2100
cagcagctgg cgggcattcc caagatgcag cggcgcctcc aggagctctg ccagatcctg  2160
ggcgaggccg tggccccagc gcatgtgccg gcacctagcc cgcaaggccc tggtggcctc  2220
cagggtgcct ccacctga                                                 2238
```

<210> SEQ ID NO 18
<211> LENGTH: 745
<212> TYPE: PRT
<213> ORGANISM: Homo sapiens

<400> SEQUENCE: 18

```
Met Pro Val Leu Ser Arg Pro Arg Pro Trp Arg Gly Asn Thr Leu Lys
1               5                   10                  15

Arg Thr Ala Val Leu Leu Ala Leu Ala Ala Tyr Gly Ala His Lys Val
            20                  25                  30

Tyr Pro Leu Val Arg Gln Cys Leu Ala Pro Ala Arg Gly Leu Gln Ala
        35                  40                  45

Pro Ala Gly Glu Pro Thr Gln Glu Ala Ser Gly Val Ala Ala Ala Lys
    50                  55                  60

Ala Gly Met Asn Arg Val Phe Leu Gln Arg Leu Leu Trp Leu Leu Arg
65                  70                  75                  80

Leu Leu Phe Pro Arg Val Leu Cys Arg Glu Thr Gly Leu Leu Ala Leu
                85                  90                  95

His Ser Ala Ala Leu Val Ser Arg Thr Phe Leu Ser Val Tyr Val Ala
            100                 105                 110

Arg Leu Asp Gly Arg Leu Ala Arg Cys Ile Val Arg Lys Asp Pro Arg
        115                 120                 125

Ala Phe Gly Trp Gln Leu Leu Gln Trp Leu Leu Ile Ala Leu Pro Ala
    130                 135                 140

Thr Phe Val Asn Ser Ala Ile Arg Tyr Leu Glu Gly Gln Leu Ala Leu
145                 150                 155                 160

Ser Phe Arg Ser Arg Leu Val Ala His Ala Tyr Arg Leu Tyr Phe Ser
                165                 170                 175

Gln Gln Thr Tyr Tyr Arg Val Ser Asn Met Asp Gly Arg Leu Arg Asn
            180                 185                 190

Pro Asp Gln Ser Leu Thr Glu Asp Val Val Ala Phe Ala Ala Ser Val
        195                 200                 205

Ala His Leu Tyr Ser Asn Leu Thr Lys Pro Leu Leu Asp Val Ala Val
    210                 215                 220

Thr Ser Tyr Thr Leu Leu Arg Ala Ala Arg Ser Arg Gly Ala Gly Thr
225                 230                 235                 240

Ala Trp Pro Ser Ala Ile Ala Gly Leu Val Val Phe Leu Thr Ala Asn
                245                 250                 255

Val Leu Arg Ala Phe Ser Pro Lys Phe Gly Glu Leu Val Ala Glu Glu
            260                 265                 270

Ala Arg Arg Lys Gly Glu Leu Arg Tyr Met His Ser Arg Val Val Ala
        275                 280                 285

Asn Ser Glu Glu Ile Ala Phe Tyr Gly Gly His Glu Val Glu Leu Ala
    290                 295                 300

Leu Leu Gln Arg Ser Tyr Gln Asp Leu Ala Ser Gln Ile Asn Leu Ile
```

```
            305                 310                 315                 320
Leu Leu Glu Arg Leu Trp Tyr Val Met Leu Glu Gln Phe Leu Met Lys
            325                 330                 335
Tyr Val Trp Ser Ala Ser Gly Leu Leu Met Val Ala Val Pro Ile Ile
            340                 345                 350
Thr Ala Thr Gly Tyr Ser Glu Ser Asp Ala Glu Ala Val Lys Lys Ala
            355                 360                 365
Ala Leu Glu Lys Lys Glu Glu Glu Leu Val Ser Glu Arg Thr Glu Ala
            370                 375                 380
Phe Thr Ile Ala Arg Asn Leu Leu Thr Ala Ala Asp Ala Ile Glu
385                 390                 395                 400
Arg Ile Met Ser Ser Tyr Lys Glu Val Thr Glu Leu Ala Gly Tyr Thr
                405                 410                 415
Ala Arg Val His Glu Met Phe Gln Val Phe Glu Asp Val Gln Arg Cys
            420                 425                 430
His Phe Lys Arg Pro Arg Glu Leu Glu Asp Ala Gln Ala Gly Ser Gly
            435                 440                 445
Thr Ile Gly Arg Ser Gly Val Arg Val Glu Gly Pro Leu Lys Ile Arg
            450                 455                 460
Gly Gln Val Val Asp Val Glu Gln Gly Ile Ile Cys Glu Asn Ile Pro
465                 470                 475                 480
Ile Val Thr Pro Ser Gly Glu Val Val Ala Ser Leu Asn Ile Arg
                485                 490                 495
Val Glu Glu Gly Met His Leu Leu Ile Thr Gly Pro Asn Gly Cys Gly
                500                 505                 510
Lys Ser Ser Leu Phe Arg Ile Leu Gly Gly Leu Trp Pro Thr Tyr Gly
            515                 520                 525
Gly Val Leu Tyr Lys Pro Pro Pro Gln Arg Met Phe Tyr Ile Pro Gln
            530                 535                 540
Arg Pro Tyr Met Ser Val Gly Ser Leu Arg Asp Gln Val Ile Tyr Pro
545                 550                 555                 560
Asp Ser Val Glu Asp Met Gln Arg Lys Gly Tyr Ser Glu Gln Asp Leu
                565                 570                 575
Glu Ala Ile Leu Asp Val Val His Leu His His Ile Leu Gln Arg Glu
            580                 585                 590
Gly Gly Trp Glu Ala Met Cys Asp Trp Lys Asp Val Leu Ser Gly Gly
            595                 600                 605
Glu Lys Gln Arg Ile Gly Met Ala Arg Met Phe Tyr His Arg Pro Lys
            610                 615                 620
Tyr Ala Leu Leu Asp Glu Cys Thr Ser Ala Val Ser Ile Asp Val Glu
625                 630                 635                 640
Gly Lys Ile Phe Gln Ala Ala Lys Asp Ala Gly Ile Ala Leu Leu Ser
                645                 650                 655
Ile Thr His Arg Pro Ser Leu Trp Lys Tyr His Thr His Leu Leu Gln
            660                 665                 670
Phe Asp Gly Glu Gly Gly Trp Lys Phe Glu Lys Leu Asp Ser Ala Ala
            675                 680                 685
Arg Leu Ser Leu Thr Glu Glu Lys Gln Arg Leu Glu Gln Gln Leu Ala
            690                 695                 700
Gly Ile Pro Lys Met Gln Arg Arg Leu Gln Glu Leu Cys Gln Ile Leu
705                 710                 715                 720
Gly Glu Ala Val Ala Pro Ala His Val Pro Ala Pro Ser Pro Gln Gly
                725                 730                 735
```

```
Pro Gly Gly Leu Gln Gly Ala Ser Thr
        740                 745
```